US008198421B2

(12) United States Patent
Samulski

(10) Patent No.: US 8,198,421 B2
(45) Date of Patent: Jun. 12, 2012

(54) MODIFIED FACTOR VIII AND FACTOR IX GENES AND VECTORS FOR GENE THERAPY

(75) Inventor: Richard J. Samulski, Chapel Hill, NC (US)

(73) Assignee: Asklepios Biopharmaceutical, Inc., Chapel Hill, NC (US)

(*) Notice: Subject to any disclaimer, the term of this patent is extended or adjusted under 35 U.S.C. 154(b) by 290 days.

(21) Appl. No.: 12/305,508

(22) PCT Filed: Jun. 19, 2007

(86) PCT No.: PCT/US2007/071553

§ 371 (c)(1), (2), (4) Date: Sep. 23, 2009

(87) PCT Pub. No.: WO2007/149852

PCT Pub. Date: Dec. 27, 2007

(65) Prior Publication Data

US 2010/0284971 A1 Nov. 11, 2010

Related U.S. Application Data

(60) Provisional application No. 60/805,171, filed on Jun. 19, 2006, provisional application No. 60/824,338, filed on Sep. 1, 2006, provisional application No. 60/847,337, filed on Sep. 26, 2006.

(51) Int. Cl.

| | |
|---|---|
| ***C07H 21/02*** | (2006.01) |
| ***A01N 63/00*** | (2006.01) |
| ***C12N 15/63*** | (2006.01) |
| ***A61K 48/00*** | (2006.01) |

(52) U.S. Cl. .................. 536/23.1; 424/93.2; 435/320.1; 514/44 R

(58) Field of Classification Search ................. 536/23.1; 424/93.2; 435/320.1; 514/44 R See application file for complete search history.

(56) References Cited

U.S. PATENT DOCUMENTS

| | | | |
|---|---|---|---|
| 4,501,729 | A | 2/1985 | Boucher et al. |
| 5,478,745 | A | 12/1995 | Samulski et al. |
| 6,204,059 | B1 | 3/2001 | Samulski et al. |
| 6,268,213 | B1 | 7/2001 | Samulski et al. |
| 6,410,300 | B1 | 6/2002 | Samulski et al. |
| 6,489,162 | B1 | 12/2002 | Shenk et al. |
| 6,491,907 | B1 | 12/2002 | Rabinowitz et al. |
| 6,548,286 | B1 | 4/2003 | Samulski et al. |
| 6,627,617 | B1 | 9/2003 | Samulski et al. |
| 6,670,176 | B1 | 12/2003 | Samulski et al. |
| 6,703,237 | B2 | 3/2004 | Samulski et al. |
| 6,924,365 | B1 | 8/2005 | Miller et al. |
| 6,951,753 | B2 | 10/2005 | Shenk et al. |
| 7,172,893 | B2 | 2/2007 | Rabinowitz et al. |
| 7,201,898 | B2 | 4/2007 | Monahan et al. |
| 7,229,823 | B2 | 6/2007 | Samulski et al. |
| 7,465,583 | B2 | 12/2008 | Samulski et al. |
| 2003/0148506 | A1 | 8/2003 | Kotin et al. |
| 2003/0223998 | A1 | 12/2003 | Lamber, Jr. et al. |
| 2004/0029106 | A1 | 2/2004 | Samulski et al. |
| 2004/0180440 | A1 | 9/2004 | Zolotukhin |
| 2004/0197895 | A1 | 10/2004 | Kotin et al. |
| 2005/0106558 | A1 | 5/2005 | Perabo et al. |
| 2008/0269149 | A1 | 10/2008 | Bowles et al. |

OTHER PUBLICATIONS

Manno et al (Nature Medicine, 12 (3): 342-347, 592; 592; 2006).*

Hasbrouck et al (Gene Therapy, 15: 870-875, 2008).*

Warrington et al (Hum Gene, 119: 571-603, 2006).*

Manno et al. 2006. AAV2 Capid-Specific CD8+ T Cells Limit the Duration of Gene Therapy in Humans and Cross React with AAV-8 Capsid. Blood, 108:11, pp. 138A-139A Part 1.

Connelly et al. 1998. Sustained Phenotypic Correction of Murine Hemophilia A by In Vivo Gene Therapy. Blood, 91:9, pp. 3273-3281.

Sarker et al. 2004. Total Correction of Hemophilia A Mice with Canine FVIII Using AAV8 Serotype. Blood, 103:4, pp. 1253-1260.

Xiao et al. 1997. A Novel 165-Base-Pair Terminal Repeat Sequence Is the Sole cis Requirement for the Adeno Associated Virus Life Cycle. Journal of Virology, 71:2, pp. 941-948.

Samulski et al. 1989. Helper-Free Stocks of Recombinant Adeno-Associated Viruses: Normal Integration Does not Require Gene Expression. Journal of Virology, 63:3822-3828.

Kajigaya et al. 1991. Self-assembled B19 parvovirus capsids, produced in a baculovirus system, are antigenically and immunogenically similar to native virions. Prog. Nat'l Acad. Sci. USA 88:4646-50.

Ruffing et al. 1992. Assembly of Virus-like Particles by Recombinant Structural Proteins of Adeno-Associated Virus Type 2 in Insect Cells. Journal of Virology 66:6922-30.

Kimbauer et al. 1996. Virus-like Particles of Bovine Papillomavirus Type 4 in Propyactic and Therapeutic Immunization. Virology. 219:37-44.

Zhao et al. 2000. BPV1 E2 Protein Enhances Packaging of Full-Length Plasmid DNA in BPV1 Pseudovirions. Virology. 272:382-93.

Sharp, P.M. and Li, W.H. 1987. The Codon Adaptation Index—A Measure of Directional Synonymous Codon Usage Bias, and its Potential Applications. Nucleic Acids Research, 15:3.

* cited by examiner

*Primary Examiner* — Peter Paras, Jr.

*Assistant Examiner* — Magdalene Sgagias

(74) *Attorney, Agent, or Firm* — Marianne Fuierer; Andrew Gerschutz; Moore & Van Allen, PLLC

(57) ABSTRACT

The present invention relates to a modified and optimized Factor VIII or Factor IX nucleic acid for inclusion in a chimeric virus vector. Use of such vector can be used for treatment of hemophilia.

16 Claims, 33 Drawing Sheets

In Vitro GFP Transduction 1x10e9vg HPMC

In Vitro GFP Dose Response
Single vs. Double Stranded Genome

Plateau FIX Expression in HPMC and C2C12 Cells 24 hours Post Admin Infection at 1x10e9vg/titer

**APTT *In Vitro* Results**

| | AAV-2 (Control) | BNP2.5-FIX | (ds)BNP2.5-FIX |
|---|---|---|---|
| FIX ng/ml Total | 43.2 | 45.3 | 477.9 |
| FIX % of Normal Plasma | <5% | <5% | 8.8% |
| APTT Timing (seconds) | 150.0 | 146.4 | 65.6 |
| | | | |

APTT HPMC In Vitro Lysate from 1x10e9vg/titer Infection 24 Hours Post Infection hFIX In Vitro Every 24 Hours HPMC Cell Lysate Expression Evaluated with ELISA

FIX In Vivo Data from R333Q Model 6 Weeks Post Injection

FIX In Vivo Data from R333Q Model 6 Weeks Post Injection

C57/Blk6 Portal Vein Administration
1x10*10vg/animal = 4x10*11vg/kg (n=4/cohort)

4x10e11 vg/kg used in the Avigen liver trial was safe, however not therapeutic.

8x10e10vg/kg used in the Avigen liver trial was safe, however not therapeutic.

CTGGCGCGCTCGCTCGCTCACTGAGGCCGCCCGGGCAAAGCCCGGG
CGTCGGGCGACCTTTGGTCGCCCGGCCTCAGTGAGCGAGCGAGCGC
GCAGAGAGGGAGTGGAATTCGAGCtcgagcttgggctgcaggtcgagggcactg
ggaggatgttgagtaagatggaaaactactgatgacccttgcagagacagagtattaggacatg
tttgaacaggggccgggcgatcagcaggtagctctagaggatccccgtctgtctgcacatttcgt
agagcgagtgttccgatactctaatctccctaggcaaggttcatatttgtgtaggttacttattctcct
tttgttgactaagtcaataatcagaatcagcaggtttggagtcagcttggcagggatcagcagcct
gggttggaaggagggggtataaaagccccttcaccaggagaagccgtcacacagatccacaa
gctcctgacaggaagctctaggtgactctcttaaggtagccttgcagaagttggtcgtgaggcactggc
tagccctaaggtaagttggcgccgtttaagggatggttggttggtggggtattaatgtttaattacct
tttttacaggcctgaagatctccaccATGCAGCGCGTGAACATGATCATGGCCGA
GAGCCCTGGCCTGATCACCATCTGCCTGCTGGGCTACCTGCTGAGCG
CCGAGTGCACCGTGTTCCTGGACCACGAGAACGCCAACAAGATCCT
GAACCGGCCCAAGAGATACAACAGCGGCAAGCTGGAGGAGTTCGTG
CAGGGCAACCTGGAGAGGGAGTGCATGGAGGAGAAGTGCAGCTTCG
AGGAGGCCAGGGAAGTGTTCGAGAACACCGAGCGGACCACCGAGTT
CTGGAAGCAGTACGTGGACGGCGACCAGTGCGAGAGCAACCCTTGC
CTGAACGGCGGCAGCTGCAAGGACGACATCAACAGCTACGAGTGCT
GGTGCCCTTTCGGCTTCGAGGGCAAGAACTGCGAGCTGGACGTGAC
CTGCAACATCAAGAACGGCCGCTGCGAGCAGTTCTGCAAGAACAGC
GCCGACAACAAAGTGGTGTGTAGCTGCACCGAGGGCTACAGACTGG
CCGAGAACCAGAAGAGCTGCGAGCCCGCCGTGCCCTTCCCCTGCGG
CAGAGTGAGCGTGTCCCAGACCAGCAAGCTGACCAGAGCCGAGACC
GTGTTCCCCGACGTGGACTACGTGAATAGCACCGAGGCCGAGACCA
TCCTGGACAACATCACCCAGAGCACCCAGTCCTTCAACGACTTCACC
AGAGTTGTGGGCGGCGAGGACGCCAAGCCCGGCCAGTTCCCC

Figure 15 A

TGGCAGGTGGTGCTGAACGGCAAAGTGGATGCCTTCTGCGGCGGCA
GCATCGTGAACGAGAAGTGGATCGTGACAGCCGCCCACTGCGTGGA
GACCGGCGTGAAGATCACCGTGGTGGCCGGCGAACACAATATCGAG
GAGACCGAGCACACCGAGCAGAAGCGGAACGTCATCCGGATTATCC
CCCACCACAACTACAACGCCGCCATCAACAAGTACAACCACGACATC
GCCCTGCTGGAGCTGGACGAGCCTCTGGTGCTGAATAGCTACGTGAC
CCCCATCTGCATCGCCGACAAGGAGTACACCAACATCTTCCTGAAGT
TCGGCAGCGGCTACGTGTCCGGCTGGGGCAGAGTGTTCCACAAGGG
CAGAAGCGCCCTGGTGCTGCAGTACCTGAGAGTGCCCCTGGTGGAC
AGAGCCACCTGCCTGAGGAGCACCAAGTTCACCATCTACAACAACAT
GTTCTGCGCCGGCTTCCACGAGGGCGGCAGAGACAGCTGCCAGGGC
GACAGCGGCGGACCCCACGTGACCGAAGTGGAGGGCACCAGCTTCC
TGACCGGCATCATCAGCTGGGGCGAGGAGTGCGCCATGAAGGGCAA
GTACGGCATCTACACCAAAGTGAGCCGGTACGTGAACTGGATCAAG
GAGAAAACCAAGCTGACCTGATGAgcatgcctagagctcgctgatcagcctcgac
tgtgccttctagttgccagccatctgttgtttgcccctcccccgtgccttccttgaccctggaaggtg
ccactcccactgtcctttcctaataaaatgaggaaattgcatcgcattgtctgagtaggtgtcattct
attctggggggtggggtggggcaggacagcaagggggaggattgggaagacaatagcagg
catgctggggaa*AGCTTCAGCTAGAGCATGGCTACGTAGATAAGTAGCAT*
*GGCGGGTTAATCATTAACTACAAGGAACCCCTAGTGATGGAGTTGGC*
*CACTCCCTCTCTGCGCGCTCGCTCGCTCACTGAGGCCGGGCGACCAA*
*AGGTCGCCCGACGCCCGGGCTTTGCCCGGGCGGCCTCAGTGAGCGA*
*GCGAGCGCGCAG*

Figure 15 B

Codon Quality Distribution
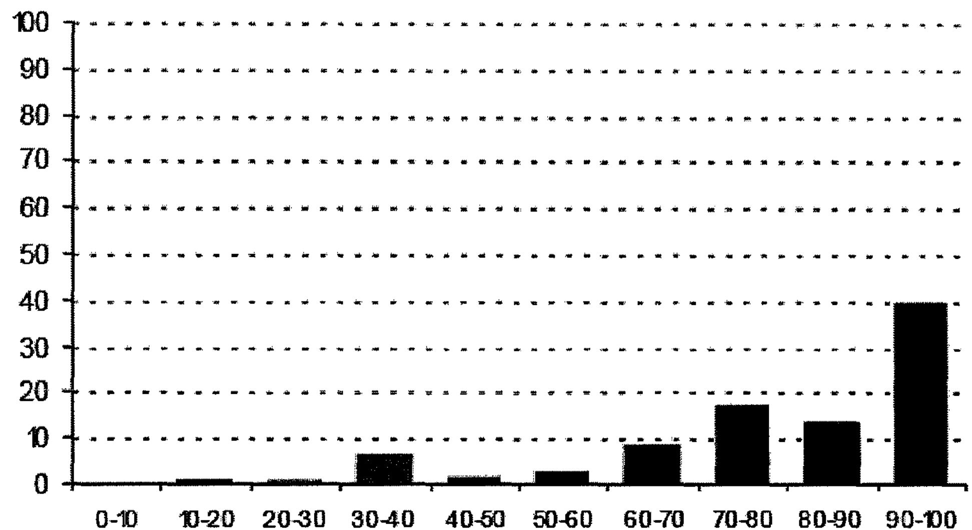
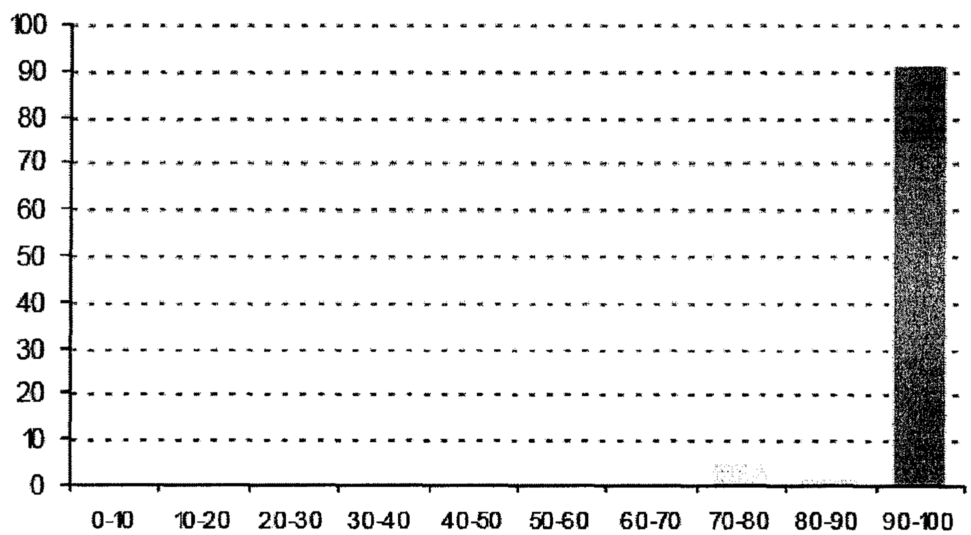
Figure 16

GC content
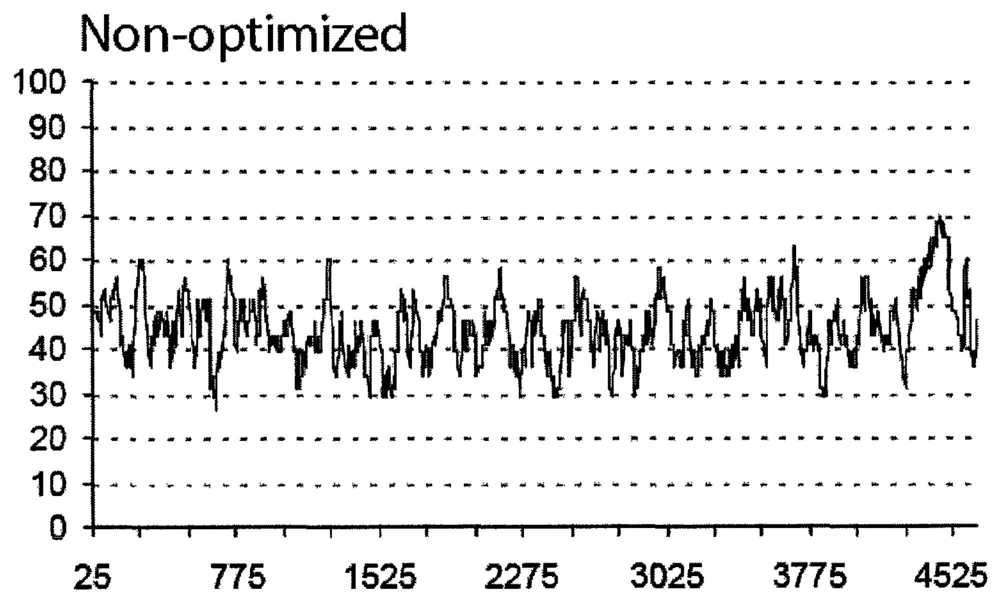
Fig. 3a
Average GC content: 44 %
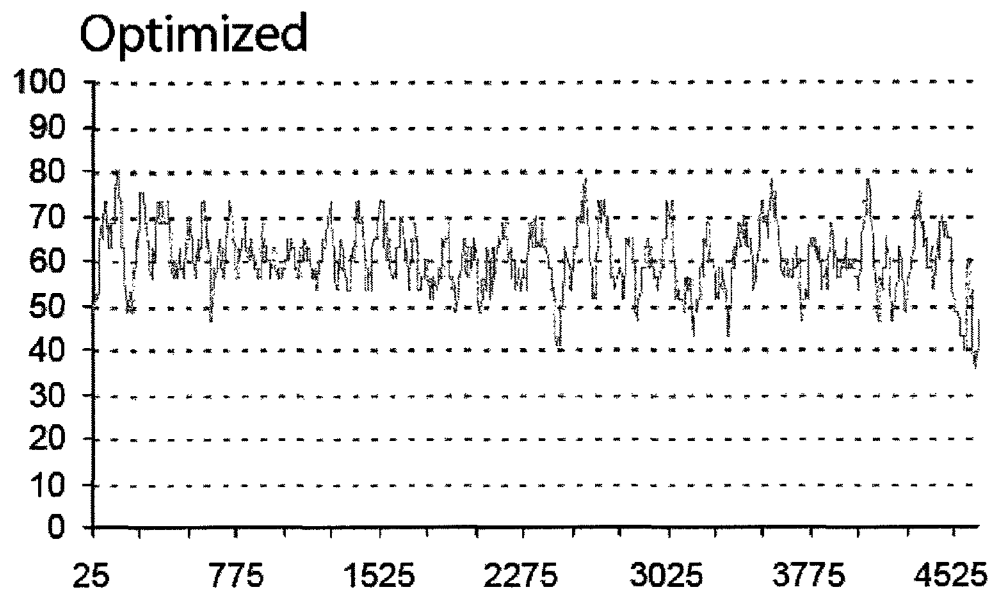
Fig. 3b
Average GC content: 60 %
Figure 18

*<u>ggtaccgccacc</u>*atgcagatcgagctgtccacatgctttttctgtgcctgctgcggttctgcttcagc
gccacccggcggtactacctgggcgccgtggagctgtcctgggactacatgcagagcgacctggg
cgagctgcccgtggacgcccggttcccccccagagtgcccaagagcttccccttcaacaccagcgt
ggtgtacaagaaaaccctgttcgtggagttcaccgtgcacctgttcaacatcgccaagcccaggcc
cccctggatgggcctgctgggccccaccatccaggccgaggtgtacgacaccgtggtgatcaccct
gaagaacatggccagccaccccgtgagcctgcacgccgtgggcgtgagctactggaaggcctcc
gagggcgccgagtacgacgaccagaccagccagcgggagaaagaggacgacaaagtctttcc
tggcggcagccacacctacgtgtggcaggtcctgaaagaaaacggccccatggcctccgacccc
ctgtgcctgacctacagctacctgagccacgtggacctggtgaaggacctgaacagcgggctgatt
ggggccctgctggtctgccgggagggcagcctggccaaagagaaaacccagaccctgcacaag
ttcatcctgctgttcgccgtgttcgacgagggcaagagctggcacagcgagaccaagaacagcctg
atgcaggaccgggacgccgcctctgccagagcctggcccaagatgcacaccgtgaacggctacg
tgaacagaagcctgcccggcctgattggctgccaccggaagagcgtgtactggcacgtgatcggc
atgggcaccacacccgaggtgcacagcatctttctggaagggcacacctttctggtgcggaaccac
cggcaggccagcctggaaatcagccctatcaccttcctgaccgcccagacactgctgatggacctg
ggccagttcctgctgttttgccacatcagctctcaccagcacgacggcatggaagcctacgtgaagg
tggactcctgccccgaggaaccccagctgcggatgaagaacaacgaggaagccgaggactacg
acgacgacctgaccgacagcgagatggacgtggtgcggttcgacgacgacaacagccccagctt
catccagatcagaagcgtggccaagaagcaccccaagacctgggtgcactacatcgccgccga
ggaagaggactgggactacgcccccctggtgctggcccccgacgacagaagctacaagagcca
gtacctgaacaatggcccccagcggatcggccggaagtacaagaaagtgcggttcatggcctaca
ccgacgagaccttcaagacccgggaggccatccagcacgagagcggcatcctgggccccctgct
gtacggcgaagtgggcgacacactgctgatcatcttcaagaaccaggccagccggccctacaac
atctacccccacggcatcaccgacgtgcggcccctgtacagcaggcggctgcccaagggcgtga
agcacctgaaggacttccccatcctgcccggcgagatcttcaagtacaagtggaccgtgaccgtgg

Figure 22 A aggacggccccaccaagagcgaccccagatgcctgacccggtactacagcagcttcgtgaacat
ggaacgggacctggcctccgggctgatcggacctctgctgatctgctacaaagaaagcgtggacc
agcggggcaaccagatcatgagcgacaagcggaacgtgatcctgttcagcgtgttcgatgagaac
cggtcctggtatctgaccgagaacatccagcggtttctgcccaaccctgccggggtgcagctggaa
gatcccgagttccaggccagcaacatcatgcactccatcaatggctacgtgttcgacagcctgcagc
tgtccgtgtgtctgcacgaggtggcctactggtacatcctgagcatcggcgcccagaccgacttcctg
agcgtgttcttcagcggctacaccttcaagcacaagatggtgtacgaggacaccctgaccctgttcc
ctttcagcggcgagaccgtgttcatgagcatggaaaaccccggcctgtggatcctgggctgccaca
acagcgacttccggaaccggggcatgaccgccctgctgaaggtgtccagctgcgacaagaacac
cggcgactactacgaggacagctacgaggatatcagcgcctacctgctgtccaagaacaacgcc
atcgagcccagaagcttcagccagaacagccggcaccccagcacccggcagaagcagttcaac
gccaccccccctgtgctgaagcggcaccagagagagatcacccggaccaccctgcagtccgacc
aggaagagatcgattacgacgacaccatcagcgtggagatgaaaaagaagatttcgacatcta
cgacgaggacgagaaccagagcccccggtccttccagaagaaaacccggcactactttatcgcc
gccgtggagcggctgtgggactacggcatgagcagcagcccccacgtgctgcggaaccgggcc
cagagcggcagcgtgccccagttcaagaaagtggtgttccaggaattcaccgacggcagcttcac
ccagcccctgtaccggggcgagctgaacgagcacctggggctgctggggccctacatcagggcc
gaagtggaggacaacatcatggtgaccttccggaatcaggccagcagaccctactccttctacagc
agcctgatcagctacgaagaggaccagcggcagggcgctgaaccccggaagaacttcgtgaag
cccaatgagaccaagacctacttctggaaagtgcagcaccacatggcccccaccaaggacgagt
tcgactgcaaggcctgggcctacttcagcgacgtggatctggaaaaggacgtgcactctggactga
ttggccctctgctggtgtgccacaccaacaccctgaaccccgcccacggccggcaggtgaccgtgc
aggaattcgccctgttcttcaccatcttcgacgagaccaagtcctggtacttcaccgagaatatggaa
cggaactgcagagccccctgcaacatcagatggaagatcctaccttcaaagagaactaccggttc
cacgccatcaacggctacatcatggacaccctgcctggcctggtgatggcccaggaccagaggat

Figure 22 B ccggtggtatctgctgtccatgggcagcaacgagaatatccacagcatccacttcagcggccacgt
gttcaccgtgaggaagaaagaagagtacaagatggccctgtacaacctgtaccccggcgtgttcg
agaccgtggagatgctgcccagcaaggccggcatctggcgggtggagtgtctgatcggcgagca
cctgcatgccgggatgagcaccctgtttctggtgtacagcaacaagtgccagacccccctgggcat
ggccagcggccacatccgggacttccagatcaccgcctccggccagtacggccagtgggccccc
aagctggcccggctgcactacagcggcagcatcaacgcctggtccaccaaagagcccttcagctg
gatcaaggtggacctgctggcccctatgatcatccacggcattaagacccagggcgccaggcaga
agttcagcagcctgtacatcagccagttcatcatcatgtacagcctggacggcaagaagtggcaga
cctaccggggcaacagcaccggcaccctgatggtgttcttcggcaacgtggacagcagcggcatc
aagcacaacatcttcaacccccccatcatcgcccggtacatccggctgcaccccacccactacag
catcagatccaccctgcggatggaactgatgggctgcgacctgaactcctgcagcatgcctctggg
catggaaagcaaggccatcagcgacgcccagatcacagccagcagctacttcaccaacatgttc
gccacctggtcccccctccaaggccaggctgcacctgcagggccggtccaacgcctggcggcctca
ggtgaacaaccccaaagaatggctgcaggtggactttcagaaaaccatgaaggtgaccggcgtg
accacccagggcgtgaaaagcctgctgaccagcatgtacgtgaaagagtttctgatcagcagcag
ccaggacggccaccagtggaccctgttctttcagaacggcaaggtgaaagtgttccagggcaacc
aggactccttcaccccccgtggtgaactccctggaccccccctgctgacccgctacctgcggatcca
cccccagtcttgggtgcaccagatcgccctgaggatggaagtgctgggatgtgaggcccaggatct
gtactga**CTCGAGGGGTGGCCACTGCAGCACCTGCCACTGCCGTCAC
CTCTCCCTCCTCAGCTCCAGGGCAGTGTCCCTCCCTGGCTTGCCTT
CTACCTTTGTGCTAAATCCTAGCAGACACTGCCTTGAAGCCTCCTG
AATTAACTATCATCAGTCCTGCATTTCTTTGGTGGGGGCCAGGAGG
GTGCATCCAATTTAACTTAACTCTTACCTATTTTCTGCAGGGGATCT
CAGTCGACGAGCTC**

Figure 22 C atgcagatcgagctgagtacctgctttttcctctgcctgctgcggttctgcttcagcgccacccggc
ggtactacctgggcgccgtggagctgagttgggactacatgcagagcgacctgggcgagctg
cccgtggacgcccggttccccccctcgggtgcccaagagcttccccttcaacaccagcgtggtg
tacaagaaaaccctgttcgtggagttcaccgtgcacctgttcaacatcgccaagcccaggccc
ccctggatgggcctgctgggccccaccatccaggccgaggtgtacgacaccgtggtgatcac
cctgaagaacatggccagccaccccgtgagcctgcacgccgtgggcgtgagctactggaag
gccagtgagggcgccgagtacgacgaccagaccagccagcgggagaaagaggacgac
aaggttttccctggcggcagccacacctacgtgtggcaggtcctgaaagaaaacggccccat
ggcctccgacccccctgtgcctgacctacagctacctgagccacgtggacctggtcaaggacct
gaacagcggcctgatcggcgcgctgctggtctgccgggagggcagcctggccaaagagaa
aacccagaccctgcacaagttcatcctgctgttcgctgtgttcgacgagggcaagagctggca
cagcgagaccaagaacagcctgatgcaggaccgggacgccgccagcgctcgcgcctggc
ccaagatgcacaccgtgaacggatacgtgaaccggtccctgcccgggctgatcggctgcca
ccggaagagcgtgtactggcacgtgatcggcatgggcaccacgcccgaggtgcacagcatc
ttcctcgagggccacaccttcctcgtgcggaaccaccggcaggccagcctcgagatcagccc
catcaccttcctcaccgcccagacgctgctgatggacctgggccagttcctgctcttctgccaca
tcagctcgcaccagcacgacggcatggaagcctacgtgaaggtggacagttgccccgagga
accccagctgcggatgaagaacaacgaggaagccgaggattacgacgacgacctgaccg
acagcgagatggacgtggtgcggttcgacgacgacaacagccccagcttcatccagatccg
gtccgtggccaagaagcaccccaagacctgggtgcactacatcgccgccgaggaagagga
ctgggactacgccccccctggtgctggcccccgacgaccggtcctacaagagccagtacctga
acaacgggcccccagcggatcggccggaagtacaagaaagtgcggttcatggcctacaccg
acgagaccttcaagacccgggaggccatccagcacgagagcggcatcctgggcccccctgct
gtacggcgaggtcggcgacaccctgctgatcatcttcaagaaccaggccagccggccctac
aacatctacccccacggcatcaccgacgtgcggcccctgtacagcaggcggctgcccaagg
gcgtgaagcacctgaaggacttccccatcctgcccggcgagatcttcaagtacaagtggacc

Figure 23 A gtgaccgtggaggacggccccaccaagagcgacccccgctgcctcacccggtactacagc
agcttcgtgaacatggagcgggacctggcctccggcctcatcgggcccctgctcatctgctaca
aagaaagcgtggaccagcggggcaaccagatcatgagcgacaagcggaacgtgatcctgt
tctcggtgttcgacgagaaccggagttggtatctgacggagaacatccagcggttcctccccaa
ccctgccggcgtgcagctcgaggaccccgagttccaggccagcaacatcatgcactccatca
atggctacgtgttcgacagcctgcagctgtccgtgtgcctccacgaggtggcctactggtacatc
ctgagcatcggcgcccagaccgacttcctgagcgtgttcttcagcggctacaccttcaagcaca
agatggtgtacgaggacaccctgaccctgttcccgttcagcggcgagaccgtgttcatgagcat
ggaaaaccccggcctgtggatcctgggctgccacaacagcgacttccggaaccggggcatg
accgccctgctgaaggtgtccagctgcgacaagaacaccggcgactactacgaggacagct
acgaggacatcagcgcctacctgctgtccaagaacaacgccatcgagccccggtccttcagc
cagaacagccggcaccccagcacccggcagaagcagttcaacgccaccccccctgtgctg
aagcggcaccagcgcgagatcacccggaccaccctgcagtccgaccaggaagagatcga
ctacgacgacaccatcagcgtggagatgaagaaagaggacttcgacatctacgacgagga
cgagaaccagagcccccgcagcttccagaagaaaacccggcactacttcatcgccgcggtg
gagcggctgtgggactacggcatgagcagcagcccccacgtgctgcggaaccgggcccag
agcggcagcgtgccccagttcaagaaagtggtgttccaggaattcaccgacggcagcttcac
ccagcccctgtaccggggcgagctgaacgagcacctggggctgctggggccctacatccgc
gcggaggtggaggacaacatcatggtgaccttccggaaccaggcctcccgcccctactccttc
tacagcagcctgatcagctacgaagaggaccagcggcagggcgcggagccccggaaga
acttcgtgaagcccaacgagaccaagacctacttctggaaggtgcagcaccacatggcccc
caccaaggacgagttcgactgcaaggcctgggcctacttcagcgacgtggacctcgagaag
gacgtgcactccgggctcatcggcccgctcctcgtgtgccacaccaacaccctgaaccccgc
ccacggccggcaggtgaccgtgcaggaattcgccctgttcttcaccatcttcgacgagaccaa
gtcgtggtacttcaccgagaacatggaacgcaactgcagggccccctgcaacatccagatgg
aagatcccaccttcaaagagaactaccggttccacgccatcaacggctacatcatggacacc
ctgcccggcctggtgatggcccaggaccagcgcatccggtggtatctgctgtccatgggcagc

Figure 23B aacgagaacatccacagcatccacttcagcggccacgtgttcaccgtccggaagaaagaag
agtacaagatggccctgtacaacctgtaccccggcgtgttcgagaccgtggagatgctgccca
gcaaggccggcatctggcgggtggagtgcctgatcggggagcacctccacgccggcatgtc
caccctgttcctcgtgtacagcaacaagtgccagacccccctgggcatggccagcggccaca
tccgggacttccagatcaccgcctccggccagtacggccagtgggcccccaagctggcccg
gctgcactacagcggcagcatcaacgcctggtccaccaaagagcccttcagctggatcaag
gtggacctgctcgcccccatgatcatccacgggatcaagacccagggcgccaggcagaagt
tcagcagcctgtacatcagccagttcatcatcatgtacagcctggacggcaagaagtggcag
acctaccggggcaacagcaccggcaccctgatggtgttcttcggcaacgtggacagcagcg
gcatcaagcacaacatcttcaacccccccatcatcgcccggtacatccggctgcaccccacc
cactacagcatccggtccaccctgcggatggaactgatgggctgcgacctgaactcctgcag
catgcccctggggatggaaagcaaggccatcagcgacgcccagatcacggccagcagcta
cttcaccaacatgttcgccacctggtcccccctccaaggcccgcctgcacctgcagggccggtc
caacgcctggcggcctcaggtcaacaaccccaaagagtggctgcaggttgacttccagaaa
accatgaaggtgaccggcgtgaccacccaggggtgaagagcctgctgaccagcatgtac
gtgaaagagttcctcatcagcagcagccaggacggccaccagtggacgctgttcttccagaa
cggcaaggtcaaggtgttccagggcaaccaggacagtttcacgcccgtggtgaactccctgg
acccccccctgctgacccgctacctgcggatccacccccagagctgggtccaccagatcgcc
ctgcgcatggaagtcctcggctgcgaggcgcaggacctgtactga*CTCGAGGGGTG*
*GCCACTGCAGCACCTGCCACTGCCGTCACCTCTCCCTCCTCAG*
*CTCCAGGGCAGTGTCCCTCCCTGGCTTGCCTTCTACCTTTGTG*
*CTAAATCCTAGCAGACACTGCCTTGAAGCCTCCTGAATTAACT*
*ATCATCAGTCCTGCATTTCTTTGGTGGGGGGCCAGGAGGGTGC*
*ATCCAATTTAACTTAACTCTTACCTATTTTCTGCAGGGGATCTC*
*AGTCGACGAGCTC*

Figure 23C

```
Query  1    ATGCAGCGCGTGAACATGATCATGGCAGAATCACCAGGCCTCATCACCATCTGCCTTTTA  60
            |||||||||||||||||||||||||| ||    || ||||| ||||||||||||||  |
Sbjct  1    ATGCAGCGCGTGAACATGATCATGGCCGAGAGCCCTGGCCTGATCACCATCTGCCTGCTG  60

Query  61   GGATATCTACTCAGTGCTGAATGTACAGTTTTTCTTGATCATGAAAACGCCAACAAAATT  120
            || || || || || || || || || || || || || || || |||||||||| ||
Sbjct  61   GGCTACCTGCTGAGCGCCGAGTGCACCGTGTTCCTGGACCACGAGAACGCCAACAAGATC  120

Query  121  CTGAATCGGCCAAAGAGGTATAATTCAGGTAAATTGGAAGAGTTTGTTCAAGGGAACCTT  180
            ||||| ||||| ||||| || ||    || ||  |||| ||||| || || || |||||
Sbjct  121  CTGAACCGGCCCAAGAGATACAACAGCGGCAAGCTGGAGGAGTTCGTGCAGGGCAACCTG  180

Query  181  GAGAGAGAATGTATGGAAGAAAAGTGTAGTTTTGAAGAAGCACGAGAAGTTTTTGAAAAC  240
            ||||| || || ||||| || ||||| || || || || || |  | |||||  || || |||
Sbjct  181  GAGAGGGAGTGCATGGAGGAGAAGTGCAGCTTCGAGGAGGCCAGGGAAGTGTTCGAGAAC  240

Query  241  ACGGAAAGAACAACTGAATTTTGGAAGCAGTATGTTGATGGTGACCAGTGTGAGTCCAAT  300
            || ||  | || || || || ||||||||| || || || || |||||||| |||  |||
Sbjct  241  ACCGAGCGGACCACCGAGTTCTGGAAGCAGTACGTGGACGGCGACCAGTGCGAGAGCAAC  300

Query  301  CCATGTTTAAATGGCGGCAGTTGCAAGGATGACATTAATTCCTATGAATGTTGGTGTCCC  360
            || ||  | || |||||||| |||||||| ||||| ||    ||| || ||  ||||| ||
Sbjct  301  CCTTGCCTGAACGGCGGCAGCTGCAAGGACGACATCAACAGCTACGAGTGCTGGTGCCCT  360
```

Figure 24 A

```
Query  361   TTTGGATTTGAAGGAAAGAACTGTGAGCTCGATGTAACATGTAACATTAAGAATGGCAGA  420
             || || || || || |||||||| ||||| || || || || ||||| ||||| ||| | 
Sbjct  361   TTCGGCTTCGAGGGCAAGAACTGCGAGCTGGACGTGACCTGCAACATCAAGAACGGCCGC  420

Query  421   TGCGAGCAGTTTTGTAAAAATAGTGCTGATAACAAGGTGGTTTGCTCCTGTACTGAGGGA  480
             ||||||||||| || || || || || || ||||| ||||| ||   ||| || ||||| 
Sbjct  421   TGCGAGCAGTTCTGCAAGAACAGCGCCGACAACAAAGTGGTGTGTAGCTGCACCGAGGGC  480

Query  481   TATCGACTTGCAGAAAACCAGAAGTCCTGTGAACCAGCAGTGCCATTTCCATGCGGCCGC  540
             ||  |||| || || |||||||||  ||| || || || ||||| || || |||||| | 
Sbjct  481   TACAGACTGGCCGAGAACCAGAAGAGCTGCGAGCCCGCCGTGCCCTTCCCCTGCGGCAGA  540

Query  541   GTTTCTGTTTCACAAACTTCTAAGCTCACCCGTGCTGAGACTGTTTTTCCTGATGTGGAC  600
             ||    || || || ||    ||||| ||| | || ||||| || || || || ||||||
Sbjct  541   GTGAGCGTGTCCCAGACCAGCAAGCTGACCAGAGCCGAGACCGTGTTCCCCGACGTGGAC  600

Query  601   TATGTAAATTCTACTGAAGCTGAAACCATTTTGGATAACATCACTCAAAGCACCCAATCA  660
             || || |||   || || || || |||||  |||| |||||||| || |||||||| || 
Sbjct  601   TACGTGAATAGCACCGAGGCCGAGACCATCCTGGACAACATCACCCAGAGCACCCAGTCC  660

Query  661   TTTAATGACTTCACTCGGGTTGTTGGTGGAGAAGATGCCAAACCAGGTCAATTCCCTTGG  720
             || || ||||||||  | | ||||| || || || ||||| || || || ||||| |||
Sbjct  661   TTCAACGACTTCACCAGAGTTGTGGGCGGCGAGGACGCCAAGCCCGGCCAGTTCCCCTGG  720
```

Figure 24B

```
Query  721   CAGGTTGTTTTGAATGGTAAAGTTGATGCATTCTGTGGAGGCTCTATCGTTAATGAAAAA  780
             ||||| ||  |||| || ||||| ||||| ||||| || |||   ||||| || || ||
Sbjct  721   CAGGTGGTGCTGAACGGCAAAGTGGATGCCTTCTGCGGCGGCAGCATCGTGAACGAGAAG  780

Query  781   TGGATTGTAACTGCTGCCCACTGTGTTGAAACTGGTGTTAAAATTACAGTTGTCGCAGGT  840
             ||||| || || || |||||||| || || || || || || || || || || || ||
Sbjct  781   TGGATCGTGACAGCCGCCCACTGCGTGGAGACCGGCGTGAAGATCACCGTGGTGGCCGGC  840

Query  841   GAACATAATATTGAGGAGACAGAACATACAGAGCAAAAGCGAAATGTGATTCGAATTATT  900
             ||||| ||||| |||||||| || || || ||||| ||||| || || || || |||||
Sbjct  841   GAACACAATATCGAGGAGACCGAGCACACCGAGCAGAAGCGGAACGTCATCCGGATTATC  900

Query  901   CCTCACCACAACTACAATGCAGCTATTAATAAGTACAACCATGACATTGCCCTTCTGGAA  960
             || |||||||||||||| || || || || ||||||||||| ||||| ||||| |||||
Sbjct  901   CCCCACCACAACTACAACGCCGCCATCAACAAGTACAACCACGACATCGCCCTGCTGGAG  960

Query  961   CTGGACGAACCCTTAGTGCTAAACAGCTACGTTACACCTATTTGCATTGCTGACAAGGAA  1020
             |||||||| ||  | ||||| || |||||||| || || || ||||| || ||||||||
Sbjct  961   CTGGACGAGCCTCTGGTGCTGAATAGCTACGTGACCCCCATCTGCATCGCCGACAAGGAG  1020

Query  1021  TACACGAACATCTTCCTCAAATTTGGATCTGGCTATGTAAGTGGCTGGGGAAGAGTCTTC  1080
             ||||| ||||||||||| || || ||    ||||| ||    |||||||| ||||| |||
Sbjct  1021  TACACCAACATCTTCCTGAAGTTCGGCAGCGGCTACGTGTCCGGCTGGGGCAGAGTGTTC  1080
```

Figure 24 C

```
Query  1081  CACAAAGGGAGATCAGCTTTAGTTCTTCAGTACCTTAGAGTTCCACTTGTTGACCGAGCC  1140
             ||||| || |||   ||  | || || |||||||| ||||| || || || ||| |||||
Sbjct  1081  CACAAGGGCAGAAGCGCCCTGGTGCTGCAGTACCTGAGAGTGCCCCTGGTGGACAGAGCC  1140

Query  1141  ACATGTCTTCGATCTACAAAGTTCACCATCTATAACAACATGTTCTGTGCTGGCTTCCAT  1200
             || || ||  |    || |||||||||||||| |||||||||||||| || ||||||||
Sbjct  1141  ACCTGCCTGAGGAGCACCAAGTTCACCATCTACAACAACATGTTCTGCGCCGGCTTCCAC  1200

Query  1201  GAAGGAGGTAGAGATTCATGTCAAGGAGATAGTGGGGGACCCCATGTTACTGAAGTGGAA  1260
             || || || |||||    || || || || || || |||||||| || || ||||||||
Sbjct  1201  GAGGGCGGCAGAGACAGCTGCCAGGGCGACAGCGGCGGACCCCACGTGACCGAAGTGGAG  1260

Query  1261  GGGACCAGTTTCTTAACTGGAATTATTAGCTGGGGTGAAGAGTGTGCAATGAAAGGCAAA  1320
             || ||||| ||| | || || || || |||||||| || ||||| || ||||| |||||
Sbjct  1261  GGCACCAGCTTCCTGACCGGCATCATCAGCTGGGGCGAGGAGTGCGCCATGAAGGGCAAG  1320

Query  1321  TATGGAATATATACCAAGGTATCCCGGTATGTCAACTGGATTAAGGAAAAAACAAAGCT  1379
             || || || || ||||| ||   |||||| || |||||||| ||||| ||||| |||||
Sbjct  1321  TACGGCATCTACACCAAAGTGAGCCGGTACGTGAACTGGATCAAGGAGAAAACCAAGCT  1379
```

Figure 24D

SEQUENCE LISTING

<160> NUMBER OF SEQ ID NOS: 19

<210> SEQ ID NO 1
<211> LENGTH: 2453
<212> TYPE: DNA
<213> ORGANISM: Artificial Sequence
<220> FEATURE:
<223> OTHER INFORMATION: Synthetic construct

<400> SEQUENCE: 1

```
ctggcgcgct cgctcgctca ctgaggccgc ccgggcaaag cccgggcgtc gggcgacctt     60

tggtcgcccg gcctcagtga gcgagcgagc gcgcagagag ggagtggaat tcgagctcga    120

gcttgggctg caggtcgagg gcactgggag gatgttgagt aagatggaaa actactgatg    180

acccttgcag agacagagta ttaggacatg tttgaacagg ggccgggcga tcagcaggta    240

gctctagagg atccccgtct gtctgcacat ttcgtagagc gagtgttccg atactctaat    300

ctccctaggc aaggttcata tttgtgtagg ttacttattc tcctttttgtt gactaagtca    360

ataatcagaa tcagcaggtt tggagtcagc ttggcaggga tcagcagcct gggttggaag    420

gagggggtat aaaagcccct tcaccaggag aagccgtcac acagatccac aagctcctga    480

caggaagctc taggtgactc tcttaaggta gccttgcaga agttggtcgt gaggcactgg    540

ctagccctaa ggtaagttgg cgccgtttaa gggatggttg gttggtgggg tattaatgtt    600

taattacctt ttttacaggc ctgaagatct ccaccatgca gcgcgtgaac atgatcatgg    660

ccgagagccc tggcctgatc accatctgcc tgctgggcta cctgctgagc gccgagtgca    720

ccgtgttcct ggaccacgag aacgccaaca agatcctgaa ccggcccaag agatacaaca    780

gcggcaagct ggaggagttc gtgcagggca acctggagag ggagtgcatg gaggagaagt    840

gcagcttcga ggaggccagg gaagtgttcg agaacaccga gcggaccacc gagttctgga    900

agcagtacgt ggacggcgac cagtgcgaga gcaaccccttg cctgaacggc ggcagctgca    960

aggacgacat caacagctac gagtgctggt gccctttcgg cttcgagggc aagaactgcg   1020

agctggacgt gacctgcaac atcaagaacg gccgctgcga gcagttctgc aagaacagcg   1080

ccgacaacaa agtggtgtgt agctgcaccg agggctacag actggccgag aaccagaaga   1140

gctgcgagcc cgccgtgccc ttcccctgcg gcagagtgag cgtgtcccag accagcaagc   1200

tgaccagagc cgagaccgtg ttccccgacg tggactacgt gaatagcacc gaggccgaga   1260

ccatcctgga caacatcacc cagagcaccc agtccttcaa cgacttcacc agagttgtgg   1320

gcggcgagga cgccaagccc ggccagttcc cctggcaggt ggtgctgaac ggcaaagtgg   1380

atgccttctg cggcggcagc atcgtgaacg agaagtggat cgtgacagcc gcccactgcg   1440

tggagaccgg cgtgaagatc accgtggtgg ccggcgaaca caatatcgag gagaccgagc   1500

acaccgagca gaagcggaac gtcatccgga ttatccccca ccacaactac aacgccgcca   1560

tcaacaagta caaccacgac atcgccctgc tggagctgga cgagcctctg gtgctgaata   1620

gctacgtgac ccccatctgc atcgccgaca aggagtacac caacatcttc ctgaagttcg   1680

gcagcggcta cgtgtccggc tggggcagag tgttccacaa gggcagaagc gccctggtgc   1740

tgcagtacct gagagtgccc ctggtggaca gagccacctg cctgaggagc accaagttca   1800

ccatctacaa caacatgttc tgcgccggct tccacgaggg cggcagagac agctgccagg   1860

gcgacagcgg cggaccccac gtgaccgaag tggagggcac cagcttcctg accggcatca   1920

tcagctgggg cgaggagtgc gccatgaagg gcaagtacgg catctacacc aaagtgagcc   1980
```

```
ggtacgtgaa ctggatcaag gagaaaacca agctgacctg atgagcatgc ctagagctcg   2040

ctgatcagcc tcgactgtgc cttctagttg ccagccatct gttgtttgcc cctcccccgt   2100

gccttccttg accctggaag gtgccactcc cactgtcctt tcctaataaa atgaggaaat   2160

tgcatcgcat tgtctgagta ggtgtcattc tattctgggg ggtggggtgg ggcaggacag   2220

caagggggag gattgggaag acaatagcag gcatgctggg gaaagcttca gctagagcat   2280

ggctacgtag ataagtagca tggcgggtta atcattaact acaaggaacc cctagtgatg   2340

gagttggcca ctccctctct gcgcgctcgc tcgctcactg aggccgggcg accaaaggtc   2400

gcccgacgcc cgggctttgc ccgggcggcc tcagtgagcg agcgagcgcg cag          2453
```

<210> SEQ ID NO 2
<211> LENGTH: 116
<212> TYPE: DNA
<213> ORGANISM: Artificial Sequence
<220> FEATURE:
<223> OTHER INFORMATION: Synthetic construct

<400> SEQUENCE: 2

```
ctggcgcgct cgctcgctca ctgaggccgc ccgggcaaag cccgggcgtc gggcgacctt     60

tggtcgcccg gcctcagtga gcgagcgagc gcgcagagag ggagtggaat tcgagc        116
```

<210> SEQ ID NO 3
<211> LENGTH: 373
<212> TYPE: DNA
<213> ORGANISM: Artificial Sequence
<220> FEATURE:
<223> OTHER INFORMATION: Synthetic construct

<400> SEQUENCE: 3

```
tcgagcttgg gctgcaggtc gagggcactg ggaggatgtt gagtaagatg gaaaactact     60

gatgaccctt gcagagacag agtattagga catgtttgaa caggggccgg gcgatcagca    120

ggtagctcta gaggatcccc gtctgtctgc acatttcgta gagcgagtgt tccgatactc    180

taatctccct aggcaaggtt catatttgtg taggttactt attctccttt tgttgactaa    240

gtcaataatc agaatcagca ggtttggagt cagcttggca gggatcagca gcctgggttg    300

gaaggagggg gtataaaagc cccttcacca ggagaagccg tcacacagat ccacaagctc    360

ctgacaggaa gct                                                       373
```

<210> SEQ ID NO 4
<211> LENGTH: 51
<212> TYPE: DNA
<213> ORGANISM: Artificial Sequence
<220> FEATURE:
<223> OTHER INFORMATION: Synthetic Construct

<400> SEQUENCE: 4

```
ctaggtgact ctcttaaggt agccttgcag aagttggtcg tgaggcactg g              51
```

<210> SEQ ID NO 5
<211> LENGTH: 86
<212> TYPE: DNA
<213> ORGANISM: Artificial Sequence
<220> FEATURE:
<223> OTHER INFORMATION: Synthetic construct

<400> SEQUENCE: 5

```
ctagccctaa ggtaagttgg cgccgtttaa gggatggttg gttggtgggg tattaatgtt     60

taattacctt ttttacaggc ctgaag                                          86
```

<210> SEQ ID NO 6
<211> LENGTH: 9
<212> TYPE: DNA
<213> ORGANISM: Artificial Sequence
<220> FEATURE:
<223> OTHER INFORMATION: Synthetic Construct

<400> SEQUENCE: 6 atctccacc 9

<210> SEQ ID NO 7
<211> LENGTH: 2024
<212> TYPE: DNA
<213> ORGANISM: Artificial Sequence
<220> FEATURE:
<223> OTHER INFORMATION: Synthetic Construct

<400> SEQUENCE: 7
ctggcgcgct cgctcgctca ctgaggccgc ccgggcaaag cccgggcgtc gggcgacctt 60
tggtcgcccg gcctcagtga gcgagcgagc gcgcagagag ggagtggaat tcgagctcga 120
gcttgggctg caggtcgagg gcactgggag gatgttgagt aagatggaaa actactgatg 180
acccttgcag agacagagta ttaggacatg tttgaacagg ggccgggcga tcagcaggta 240
gctctagagg atccccgtct gtctgcacat ttcgtagagc gagtgttccg atactctaat 300
ctccctaggc aaggttcata tttgtgtagg ttacttattc tccttttgtt gactaagtca 360
ataatcagaa tcagcaggtt tggagtcagc ttggcaggga tcagcagcct gggttggaag 420
gagggggtat aaaagcccct tcaccaggag aagccgtcac acagatccac aagctcctga 480
caggaagctc taggtgactc tcttaaggta gccttgcaga agttggtcgt gaggcactgg 540
ctagccctaa ggtaagttgg cgccgtttaa gggatggttg gttggtgggg tattaatgtt 600
taattacctt ttttacaggc ctgaagatct ccaccatgca gcgcgtgaac atgatcatgg 660
ccgagagccc tggcctgatc accatctgcc tgctgggcta cctgctgagc gccgagtgca 720
ccgtgttcct ggaccacgag aacgccaaca agatcctgaa ccggcccaag agatacaaca 780
gcggcaagct ggaggagttc gtgcagggca acctggagag ggagtgcatg gaggagaagt 840
gcagcttcga ggaggccagg gaagtgttcg agaacaccga gcggaccacc gagttctgga 900
agcagtacgt ggacggcgac cagtgcgaga gcaacccttg cctgaacggc ggcagctgca 960
aggacgacat caacagctac gagtgctggt gccctttcgg cttcgagggc aagaactgcg 1020
agctggacgt gacctgcaac atcaagaacg gccgctgcga gcagttctgc aagaacagcg 1080
ccgacaacaa agtggtgtgt agctgcaccg agggctacag actggccgag aaccagaaga 1140
gctgcgagcc cgccgtgccc ttcccctgcg gcagagtgag cgtgtcccag accagcaagc 1200
tgaccagagc cgagaccgtg ttccccgacg tggactacgt gaatagcacc gaggccgaga 1260
ccatcctgga caacatcacc cagagcaccc agtccttcaa cgacttcacc agagttgtgg 1320
gcggcgagga cgccaagccc ggccagttcc cctggcaggt ggtgctgaac ggcaaagtgg 1380
atgccttctg cggcggcagc atcgtgaacg agaagtggat cgtgacagcc gcccactgcg 1440
tggagaccgg cgtgaagatc accgtggtgg ccggcgaaca caatatcgag gagaccgagc 1500
acaccgagca gaagcggaac gtcatccgga ttatccccca ccacaactac aacgccgcca 1560
tcaacaagta caaccacgac atcgccctgc tggagctgga cgagcctctg gtgctgaata 1620
gctacgtgac ccccatctgc atcgccgaca aggagtacac caacatcttc ctgaagttcg 1680
gcagcggcta cgtgtccggc tggggcagag tgttccacaa gggcagaagc gccctggtgc 1740

```
tgcagtacct gagagtgccc ctggtggaca gagccacctg cctgaggagc accaagttca   1800

ccatctacaa caacatgttc tgcgccggct tccacgaggg cggcagagac agctgccagg   1860

gcgacagcgg cggaccccac gtgaccgaag tggagggcac cagcttcctg accggcatca   1920

tcagctgggg cgaggagtgc gccatgaagg gcaagtacgg catctacacc aaagtgagcc   1980

ggtacgtgaa ctggatcaag gagaaaacca agctgacctg atga                    2024


<210> SEQ ID NO 8
<211> LENGTH: 239
<212> TYPE: DNA
<213> ORGANISM: Artificial Sequence
<220> FEATURE:
<223> OTHER INFORMATION: Synthetic Construct

<400> SEQUENCE: 8

gcatgcctag agctcgctga tcagcctcga ctgtgccttc tagttgccag ccatctgttg     60

tttgcccctc ccccgtgcct tccttgaccc tggaaggtgc cactcccact gtcctttcct    120

aataaaatga ggaaattgca tcgcattgtc tgagtaggtg tcattctatt ctggggggtg    180

gggtggggca ggacagcaag ggggaggatt gggaagacaa tagcaggcat gctggggaa     239


<210> SEQ ID NO 9
<211> LENGTH: 190
<212> TYPE: DNA
<213> ORGANISM: Artificial Sequence
<220> FEATURE:
<223> OTHER INFORMATION: Synthetic Construct

<400> SEQUENCE: 9

agcttcagct agagcatggc tacgtagata agtagcatgg cgggttaatc attaactaca     60

aggaacccct agtgatggag ttggccactc cctctctgcg cgctcgctcg ctcactgagg    120

ccgggcgacc aaaggtcgcc cgacgcccgg gctttgcccg ggcggcctca gtgagcgagc    180

gagcgcgcag                                                           190


<210> SEQ ID NO 10
<211> LENGTH: 4428
<212> TYPE: DNA
<213> ORGANISM: Artificial Sequence
<220> FEATURE:
<223> OTHER INFORMATION: Synthetic Construct

<400> SEQUENCE: 10

ggtaccgcca ccatgcagat cgagctgtcc acatgctttt ttctgtgcct gctgcggttc     60

tgcttcagcg ccacccggcg gtactacctg ggcgccgtgg agctgtcctg ggactacatg    120

cagagcgacc tgggcgagct gcccgtggac gcccggttcc cccccagagt gcccaagagc    180

ttccccttca acaccagcgt ggtgtacaag aaaaccctgt tcgtggagtt caccgtgcac    240

ctgttcaaca tcgccaagcc caggcccccc tggatgggcc tgctgggccc caccatccag    300

gccgaggtgt acgacaccgt ggtgatcacc ctgaagaaca tggccagcca ccccgtgagc    360

ctgcacgccg tgggcgtgag ctactggaag gcctccgagg gcgccgagta cgacgaccag    420

accagccagc gggagaaaga ggacgacaaa gtctttcctg gcggcagcca cacctacgtg    480

tggcaggtcc tgaaagaaaa cggccccatg gcctccgacc ccctgtgcct gacctacagc    540

tacctgagcc acgtggacct ggtgaaggac ctgaacagcg ggctgattgg ggccctgctg    600

gtctgccggg agggcagcct ggccaaagag aaaacccaga ccctgcacaa gttcatcctg    660

ctgttcgccg tgttcgacga gggcaagagc tggcacagcg agaccaagaa cagcctgatg    720
```

-continued

```
caggaccggg acgccgcctc tgccagagcc tggcccaaga tgcacaccgt gaacggctac    780
gtgaacagaa gcctgcccgg cctgattggc tgccaccgga agagcgtgta ctggcacgtg    840
atcggcatgg gcaccacacc cgaggtgcac agcatctttc tggaagggca cacctttctg    900
gtgcggaacc accggcaggc cagcctggaa atcagcccta tcaccttcct gaccgcccag    960
acactgctga tggacctggg ccagttcctg ctgttttgcc acatcagctc tcaccagcac   1020
gacggcatgg aagcctacgt gaaggtggac tcctgccccg aggaacccca gctgcggatg   1080
aagaacaacg aggaagccga ggactacgac gacgacctga ccgacagcga gatggacgtg   1140
gtgcggttcg acgacgacaa cagccccagc ttcatccaga tcagaagcgt ggccaagaag   1200
caccccaaga cctgggtgca ctacatcgcc gccgaggaag aggactggga ctacgccccc   1260
ctggtgctgg cccccgacga cagaagctac aagagccagt acctgaacaa tggcccccag   1320
cggatcggcc ggaagtacaa gaaagtgcgg ttcatggcct acaccgacga gaccttcaag   1380
acccgggagg ccatccagca cgagagcggc atcctgggcc ccctgctgta cggcgaagtg   1440
ggcgacacac tgctgatcat cttcaagaac caggccagcc ggccctacaa catctacccc   1500
cacggcatca ccgacgtgcg gcccctgtac agcaggcggc tgcccaaggg cgtgaagcac   1560
ctgaaggact tccccatcct gcccggcgag atcttcaagt acaagtggac cgtgaccgtg   1620
gaggacggcc ccaccaagag cgaccccaga tgcctgaccc ggtactacag cagcttcgtg   1680
aacatggaac gggacctggc ctccgggctg atcggacctc tgctgatctg ctacaaagaa   1740
agcgtggacc agcggggcaa ccagatcatg agcgacaagc ggaacgtgat cctgttcagc   1800
gtgttcgatg agaaccggtc ctggtatctg accgagaaca tccagcggtt tctgcccaac   1860
cctgccgggg tgcagctgga agatcccgag ttccaggcca gcaacatcat gcactccatc   1920
aatggctacg tgttcgacag cctgcagctg tccgtgtgtc tgcacgaggt ggcctactgg   1980
tacatcctga gcatcggcgc ccagaccgac ttcctgagcg tgttcttcag cggctacacc   2040
ttcaagcaca agatggtgta cgaggacacc ctgaccctgt tccctttcag cggcgagacc   2100
gtgttcatga gcatggaaaa ccccggcctg tggatcctgg gctgccacaa cagcgacttc   2160
cggaaccggg gcatgaccgc cctgctgaag gtgtccagct gcgacaagaa caccggcgac   2220
tactacgagg acagctacga ggatatcagc gcctacctgc tgtccaagaa caacgccatc   2280
gagcccagaa gcttcagcca gaacagccgg caccccagca cccggcagaa gcagttcaac   2340
gccacccccc ctgtgctgaa gcggcaccag agagagatca cccggaccac cctgcagtcc   2400
gaccaggaag agatcgatta cgacgacacc atcagcgtgg agatgaaaaa agaagatttc   2460
gacatctacg acgaggacga gaaccagagc cccccggtcct tccagaagaa aacccggcac   2520
tactttatcg ccgccgtgga gcggctgtgg gactacggca tgagcagcag cccccacgtg   2580
ctgcggaacc gggcccagag cggcagcgtg ccccagttca agaaagtggt gttccaggaa   2640
ttcaccgacg gcagcttcac ccagcccctg taccggggcg agctgaacga gcacctgggg   2700
ctgctggggc cctacatcag ggccgaagtg gaggacaaca tcatggtgac cttccggaat   2760
caggccagca gaccctactc cttctacagc agcctgatca gctacgaaga ggaccagcgg   2820
cagggcgctg aaccccggaa gaacttcgtg aagcccaatg agaccaagac ctacttctgg   2880
aaagtgcagc accacatggc ccccaccaag gacgagttcg actgcaaggc ctgggcctac   2940
ttcagcgacg tggatctgga aaaggacgtg cactctggac tgattggccc tctgctggtg   3000
tgccacacca acaccctgaa ccccgcccac ggccggcagg tgaccgtgca ggaattcgcc   3060
ctgttcttca ccatcttcga cgagaccaag tcctggtact tcaccgagaa tatggaacgg   3120
```

aactgcagag ccccctgcaa catccagatg gaagatccta ccttcaaaga gaactaccgg 3180
ttccacgcca tcaacggcta catcatggac accctgcctg gcctggtgat ggcccaggac 3240
cagaggatcc ggtggtatct gctgtccatg ggcagcaacg agaatatcca cagcatccac 3300
ttcagcggcc acgtgttcac cgtgaggaag aaagaagagt acaagatggc cctgtacaac 3360
ctgtaccccg gcgtgttcga gaccgtggag atgctgccca gcaaggccgg catctggcgg 3420
gtggagtgtc tgatcggcga gcacctgcat gccgggatga gcaccctgtt tctggtgtac 3480
agcaacaagt gccagacccc cctgggcatg gccagcggcc acatccggga cttccagatc 3540
accgcctccg gccagtacgg ccagtgggcc cccaagctgg cccggctgca ctacagcggc 3600
agcatcaacg cctggtccac caaagagccc ttcagctgga tcaaggtgga cctgctggcc 3660
cctatgatca tccacggcat taagacccag ggcgccaggc agaagttcag cagcctgtac 3720
atcagccagt tcatcatcat gtacagcctg gacggcaaga agtggcagac ctaccggggc 3780
aacagcaccg gcaccctgat ggtgttcttc ggcaacgtgg acagcagcgg catcaagcac 3840
aacatcttca acccccccat catcgcccgg tacatccggc tgcaccccac ccactacagc 3900
atcagatcca ccctgcggat ggaactgatg ggctgcgacc tgaactcctg cagcatgcct 3960
ctgggcatgg aaagcaaggc catcagcgac gcccagatca cagccagcag ctacttcacc 4020
aacatgttcg ccacctggtc cccctccaag gccaggctgc acctgcaggg ccggtccaac 4080
gcctggcggc ctcaggtgaa caaccccaaa gaatggctgc aggtggactt tcagaaaacc 4140
atgaaggtga ccggcgtgac cacccagggc gtgaaaagcc tgctgaccag catgtacgtg 4200
aaagagtttc tgatcagcag cagccaggac ggccaccagt ggaccctgtt ctttcagaac 4260
ggcaaggtga aagtgttcca gggcaaccag gactccttca cccccgtggt gaactccctg 4320
gacccccccc tgctgacccg ctacctgcgg atccaccccc agtcttgggt gcaccagatc 4380
gccctgagga tggaagtgct gggatgtgag gcccaggatc tgtactga 4428

<210> SEQ ID NO 11
<211> LENGTH: 12
<212> TYPE: DNA
<213> ORGANISM: Artificial Sequence
<220> FEATURE:
<223> OTHER INFORMATION: Synthetic Construct

<400> SEQUENCE: 11
ggtaccgcca cc 12

<210> SEQ ID NO 12
<211> LENGTH: 4428
<212> TYPE: DNA
<213> ORGANISM: Artificial Sequence
<220> FEATURE:
<223> OTHER INFORMATION: Synthetic construct

<400> SEQUENCE: 12
ggtaccgcca ccatgcagat cgagctgtcc acatgctttt ttctgtgcct gctgcggttc 60
tgcttcagcg ccacccggcg gtactacctg ggcgccgtgg agctgtcctg ggactacatg 120
cagagcgacc tgggcgagct gcccgtggac gcccggttcc cccccagagt gcccaagagc 180
ttccccttca acaccagcgt ggtgtacaag aaaaccctgt tcgtggagtt caccgtgcac 240
ctgttcaaca tcgccaagcc caggcccccc tggatgggcc tgctgggccc caccatccag 300
gccgaggtgt acgacaccgt ggtgatcacc ctgaagaaca tggccagcca ccccgtgagc 360
ctgcacgccg tgggcgtgag ctactggaag gcctccgagg gcgccgagta cgacgaccag 420

```
accagccagc gggagaaaga ggacgacaaa gtctttcctg gcggcagcca cacctacgtg    480
tggcaggtcc tgaaagaaaa cggccccatg gcctccgacc ccctgtgcct gacctacagc    540
tacctgagcc acgtggacct ggtgaaggac ctgaacagcg ggctgattgg ggccctgctg    600
gtctgccggg agggcagcct ggccaaagag aaaacccaga ccctgcacaa gttcatcctg    660
ctgttcgccg tgttcgacga gggcaagagc tggcacagcg agaccaagaa cagcctgatg    720
caggaccggg acgccgcctc tgccagagcc tggcccaaga tgcacaccgt gaacggctac    780
gtgaacagaa gcctgcccgg cctgattggc tgccaccgga agagcgtgta ctggcacgtg    840
atcggcatgg gcaccacacc cgaggtgcac agcatctttc tggaagggca cacctttctg    900
gtgcggaacc accggcaggc cagcctggaa atcagcccta tcaccttcct gaccgcccag    960
acactgctga tggacctggg ccagttcctg ctgttttgcc acatcagctc tcaccagcac   1020
gacggcatgg aagcctacgt gaaggtggac tcctgccccg aggaacccca gctgcggatg   1080
aagaacaacg aggaagccga ggactacgac gacgacctga ccgacagcga gatggacgtg   1140
gtgcggttcg acgacgacaa cagccccagc ttcatccaga tcagaagcgt ggccaagaag   1200
caccccaaga cctgggtgca ctacatcgcc gccgaggaag aggactggga ctacgccccc   1260
ctggtgctgg cccccgacga cagaagctac aagagccagt acctgaacaa tggcccccag   1320
cggatcggcc ggaagtacaa gaaagtgcgg ttcatggcct acaccgacga gaccttcaag   1380
acccgggagg ccatccagca cgagagcggc atcctgggcc ccctgctgta cggcgaagtg   1440
ggcgacacac tgctgatcat cttcaagaac caggccagcc ggccctacaa catctacccc   1500
cacggcatca ccgacgtgcg gcccctgtac agcaggcggc tgcccaaggg cgtgaagcac   1560
ctgaaggact tccccatcct gcccggcgag atcttcaagt acaagtggac cgtgaccgtg   1620
gaggacggcc ccaccaagag cgaccccaga tgcctgaccc ggtactacag cagcttcgtg   1680
aacatggaac gggacctggc ctccgggctg atcggacctc tgctgatctg ctacaaagaa   1740
agcgtggacc agcggggcaa ccagatcatg agcgacaagc ggaacgtgat cctgttcagc   1800
gtgttcgatg agaaccggtc ctggtatctg accgagaaca tccagcggtt tctgcccaac   1860
cctgccgggg tgcagctgga agatcccgag ttccaggcca gcaacatcat gcactccatc   1920
aatggctacg tgttcgacag cctgcagctg tccgtgtgtc tgcacgaggt ggcctactgg   1980
tacatcctga gcatcggcgc ccagaccgac ttcctgagcg tgttcttcag cggctacacc   2040
ttcaagcaca agatggtgta cgaggacacc ctgaccctgt tccctttcag cggcgagacc   2100
gtgttcatga gcatggaaaa ccccggcctg tggatcctgg gctgccacaa cagcgacttc   2160
cggaaccggg gcatgaccgc cctgctgaag gtgtccagct gcgacaagaa caccggcgac   2220
tactacgagg acagctacga ggatatcagc gcctacctgc tgtccaagaa caacgccatc   2280
gagcccagaa gcttcagcca gaacagccgg caccccagca cccggcagaa gcagttcaac   2340
gccacccccc ctgtgctgaa gcggcaccag agagagatca cccggaccac cctgcagtcc   2400
gaccaggaag agatcgatta cgacgacacc atcagcgtgg agatgaaaaa agaagatttc   2460
gacatctacg acgaggacga gaaccagagc ccccggtcct tccagaagaa aacccggcac   2520
tactttatcg ccgccgtgga gcggctgtgg gactacggca tgagcagcag cccccacgtg   2580
ctgcggaacc gggcccagag cggcagcgtg ccccagttca agaaagtggt gttccaggaa   2640
ttcaccgacg gcagcttcac ccagcccctg taccggggcg agctgaacga gcacctgggg   2700
ctgctggggc cctacatcag ggccgaagtg gaggacaaca tcatggtgac cttccggaat   2760
caggccagca gaccctactc cttctacagc agcctgatca gctacgaaga ggaccagcgg   2820
```

```
cagggcgctg aaccccggaa gaacttcgtg aagcccaatg agaccaagac ctacttctgg   2880

aaagtgcagc accacatggc ccccaccaag gacgagttcg actgcaaggc ctgggcctac   2940

ttcagcgacg tggatctgga aaaggacgtg cactctggac tgattggccc tctgctggtg   3000

tgccacacca acaccctgaa ccccgcccac ggccggcagg tgaccgtgca ggaattcgcc   3060

ctgttcttca ccatcttcga cgagaccaag tcctggtact tcaccgagaa tatggaacgg   3120

aactgcagag ccccctgcaa catccagatg gaagatccta ccttcaaaga gaactaccgg   3180

ttccacgcca tcaacggcta catcatggac accctgcctg gcctggtgat ggcccaggac   3240

cagaggatcc ggtggtatct gctgtccatg ggcagcaacg agaatatcca cagcatccac   3300

ttcagcggcc acgtgttcac cgtgaggaag aaagaagagt acaagatggc cctgtacaac   3360

ctgtaccccg gcgtgttcga gaccgtggag atgctgccca gcaaggccgg catctggcgg   3420

gtggagtgtc tgatcggcga gcacctgcat gccgggatga gcaccctgtt tctggtgtac   3480

agcaacaagt gccagacccc cctgggcatg gccagcggcc acatccggga cttccagatc   3540

accgcctccg gccagtacgg ccagtgggcc cccaagctgg cccggctgca ctacagcggc   3600

agcatcaacg cctggtccac caaagagccc ttcagctgga tcaaggtgga cctgctggcc   3660

cctatgatca tccacggcat taagacccag ggcgccaggc agaagttcag cagcctgtac   3720

atcagccagt tcatcatcat gtacagcctg gacggcaaga agtggcagac ctaccggggc   3780

aacagcaccg gcaccctgat ggtgttcttc ggcaacgtgg acagcagcgg catcaagcac   3840

aacatcttca accccccat catcgcccgg tacatccggc tgcaccccac ccactacagc   3900

atcagatcca ccctgcggat ggaactgatg ggctgcgacc tgaactcctg cagcatgcct   3960

ctgggcatgg aaagcaaggc catcagcgac gcccagatca cagccagcag ctacttcacc   4020

aacatgttcg ccacctggtc cccctccaag gccaggctgc acctgcaggg ccggtccaac   4080

gcctggcggc ctcaggtgaa caaccccaaa gaatggctgc aggtggactt tcagaaaacc   4140

atgaaggtga ccggcgtgac cacccagggc gtgaaaagcc tgctgaccag catgtacgtg   4200

aaagagtttc tgatcagcag cagccaggac ggccaccagt ggaccctgtt ctttcagaac   4260

ggcaaggtga aagtgttcca gggcaaccag gactccttca cccccgtggt gaactccctg   4320

gacccccccc tgctgacccg ctacctgcgg atccaccccc agtcttgggt gcaccagatc   4380

gccctgagga tggaagtgct gggatgtgag gcccaggatc tgtactga                4428
```

<210> SEQ ID NO 13
<211> LENGTH: 240
<212> TYPE: DNA
<213> ORGANISM: Artificial Sequence
<220> FEATURE:
<223> OTHER INFORMATION: Synthetic construct

<400> SEQUENCE: 13

```
ctcgaggggt ggccactgca gcacctgcca ctgccgtcac ctctccctcc tcagctccag     60

ggcagtgtcc ctccctggct tgccttctac ctttgtgcta aatcctagca gacactgcct    120

tgaagcctcc tgaattaact atcatcagtc ctgcatttct ttggtggggg gccaggaggg    180

tgcatccaat ttaacttaac tcttacctat tttctgcagg ggatctcagt cgacgagctc    240
```

<210> SEQ ID NO 14
<211> LENGTH: 4656
<212> TYPE: DNA
<213> ORGANISM: Artificial Sequence
<220> FEATURE:
<223> OTHER INFORMATION: Synthetic construct

<400> SEQUENCE: 14

```
atgcagatcg agctgagtac ctgctttttc ctctgcctgc tgcggttctg cttcagcgcc      60
acccggcggt actacctggg cgccgtggag ctgagttggg actacatgca gagcgacctg     120
ggcgagctgc ccgtggacgc ccggttcccc cctcgggtgc ccaagagctt ccccttcaac     180
accagcgtgg tgtacaagaa aaccctgttc gtggagttca ccgtgcacct gttcaacatc     240
gccaagccca ggcccccctg gatgggcctg ctgggcccca ccatccaggc cgaggtgtac     300
gacaccgtgg tgatcaccct gaagaacatg gccagccacc ccgtgagcct gcacgccgtg     360
ggcgtgagct actggaaggc cagtgagggc gccgagtacg acgaccagac cagccagcgg     420
gagaaagagg acgacaaggt tttccctggc ggcagccaca cctacgtgtg gcaggtcctg     480
aaagaaaacg gccccatggc ctccgacccc ctgtgcctga cctacagcta cctgagccac     540
gtggacctgg tcaaggacct gaacagcggc ctgatcggcg cgctgctggt ctgccgggag     600
ggcagcctgg ccaaagagaa aacccagacc ctgcacaagt tcatcctgct gttcgctgtg     660
ttcgacgagg gcaagagctg gcacagcgag accaagaaca gcctgatgca ggaccgggac     720
gccgccagcg ctcgcgcctg gcccaagatg cacaccgtga acggatacgt gaaccggtcc     780
ctgcccgggc tgatcggctg ccaccggaag agcgtgtact ggcacgtgat cggcatgggc     840
accacgcccg aggtgcacag catcttcctc gagggccaca ccttcctcgt gcggaaccac     900
cggcaggcca gcctcgagat cagccccatc accttcctca ccgcccagac gctgctgatg     960
gacctgggcc agttcctgct cttctgccac atcagctcgc accagcacga cggcatggaa    1020
gcctacgtga aggtggacag ttgccccgag gaaccccagc tgcggatgaa gaacaacgag    1080
gaagccgagg attacgacga cgacctgacc gacagcgaga tggacgtggt gcggttcgac    1140
gacgacaaca gccccagctt catccagatc cggtccgtgg ccaagaagca ccccaagacc    1200
tgggtgcact acatcgccgc cgaggaagag gactgggact acgcccccct ggtgctggcc    1260
cccgacgacc ggtcctacaa gagccagtac ctgaacaacg ggccccagcg gatcggccgg    1320
aagtacaaga aagtgcggtt catggcctac accgacgaga ccttcaagac ccgggaggcc    1380
atccagcacg agagcggcat cctgggcccc ctgctgtacg gcgaggtcgg cgacaccctg    1440
ctgatcatct tcaagaacca ggccagccgg ccctacaaca tctaccccca cggcatcacc    1500
gacgtgcggc ccctgtacag caggcggctg cccaagggcg tgaagcacct gaaggacttc    1560
cccatcctgc ccggcgagat cttcaagtac aagtggaccg tgaccgtgga ggacggcccc    1620
accaagagcg acccccgctg cctcacccgg tactacagca gcttcgtgaa catggagcgg    1680
gacctggcct ccggcctcat cgggcccctg ctcatctgct acaaagaaag cgtggaccag    1740
cggggcaacc agatcatgag cgacaagcgg aacgtgatcc tgttctcggt gttcgacgag    1800
aaccggagtt ggtatctgac ggagaacatc cagcggttcc tccccaaccc tgccggcgtg    1860
cagctcgagg accccgagtt ccaggccagc aacatcatgc actccatcaa tggctacgtg    1920
ttcgacagcc tgcagctgtc cgtgtgcctc cacgaggtgg cctactggta catcctgagc    1980
atcggcgccc agaccgactt cctgagcgtg ttcttcagcg gctacacctt caagcacaag    2040
atggtgtacg aggacaccct gaccctgttc ccgttcagcg gcgagaccgt gttcatgagc    2100
atggaaaacc ccggcctgtg gatcctgggc tgccacaaca gcgacttccg gaaccggggc    2160
atgaccgccc tgctgaaggt gtccagctgc gacaagaaca ccggcgacta ctacgaggac    2220
agctacgagg acatcagcgc ctacctgctg tccaagaaca acgccatcga gccccggtcc    2280
ttcagccaga acagccggca ccccagcacc cggcagaagc agttcaacgc cacccccccct   2340
```

```
gtgctgaagc ggcaccagcg cgagatcacc cggaccaccc tgcagtccga ccaggaagag   2400

atcgactacg acgacaccat cagcgtggag atgaagaaag aggacttcga catctacgac   2460

gaggacgaga accagagccc ccgcagcttc cagaagaaaa cccggcacta cttcatcgcc   2520

gcggtggagc ggctgtggga ctacggcatg agcagcagcc cccacgtgct gcggaaccgg   2580

gcccagagcg gcagcgtgcc ccagttcaag aaagtggtgt tccaggaatt caccgacggc   2640

agcttcaccc agcccctgta ccggggcgag ctgaacgagc acctggggct gctggggccc   2700

tacatccgcg cggaggtgga ggacaacatc atggtgacct tccggaacca ggcctcccgc   2760

ccctactcct tctacagcag cctgatcagc tacgaagagg accagcggca gggcgcggag   2820

ccccggaaga acttcgtgaa gcccaacgag accaagacct acttctggaa ggtgcagcac   2880

cacatggccc ccaccaagga cgagttcgac tgcaaggcct gggcctactt cagcgacgtg   2940

gacctcgaga aggacgtgca ctccgggctc atcggcccgc tcctcgtgtg ccacaccaac   3000

accctgaacc ccgcccacgg ccggcaggtg accgtgcagg aattcgccct gttcttcacc   3060

atcttcgacg agaccaagtc gtggtacttc accgagaaca tggaacgcaa ctgcagggcc   3120

ccctgcaaca tccagatgga agatcccacc ttcaaagaga actaccggtt ccacgccatc   3180

aacggctaca tcatggacac cctgcccggc ctggtgatgg cccaggacca gcgcatccgg   3240

tggtatctgc tgtccatggg cagcaacgag aacatccaca gcatccactt cagcggccac   3300

gtgttcaccg tccggaagaa agaagagtac aagatggccc tgtacaacct gtaccccggc   3360

gtgttcgaga ccgtggagat gctgcccagc aaggccggca tctggcgggt ggagtgcctg   3420

atcggggagc acctccacgc cggcatgtcc accctgttcc tcgtgtacag caacaagtgc   3480

cagacccccc tgggcatggc cagcggccac atccgggact tccagatcac cgcctccggc   3540

cagtacggcc agtgggcccc caagctggcc cggctgcact acagcggcag catcaacgcc   3600

tggtccacca aagagccctt cagctggatc aaggtggacc tgctcgcccc catgatcatc   3660

cacgggatca agacccaggg cgccaggcag aagttcagca gcctgtacat cagccagttc   3720

atcatcatgt acagcctgga cggcaagaag tggcagacct accggggcaa cagcaccggc   3780

accctgatgg tgttcttcgg caacgtggac agcagcggca tcaagcacaa catcttcaac   3840

ccccccatca tcgcccggta catccggctg caccccaccc actacagcat ccggtccacc   3900

ctgcggatgg aactgatggg ctgcgacctg aactcctgca gcatgcccct ggggatggaa   3960

agcaaggcca tcagcgacgc ccagatcacg gccagcagct acttcaccaa catgttcgcc   4020

acctggtccc cctccaaggc ccgcctgcac ctgcagggcc ggtccaacgc ctggcggcct   4080

caggtcaaca accccaaaga gtggctgcag gttgacttcc agaaaaccat gaaggtgacc   4140

ggcgtgacca cccagggggt gaagagcctg ctgaccagca tgtacgtgaa agagttcctc   4200

atcagcagca gccaggacgg ccaccagtgg acgctgttct tccagaacgg caaggtcaag   4260

gtgttccagg gcaaccagga cagtttcacg cccgtggtga actccctgga cccccccctg   4320

ctgacccgct acctgcggat ccacccccag agctgggtcc accagatcgc cctgcgcatg   4380

gaagtcctcg gctgcgaggc gcaggacctg tactgactcg aggggtggcc actgcagcac   4440

ctgccactgc cgtcacctct ccctcctcag ctccagggca gtgtccctcc ctggcttgcc   4500

ttctaccttt gtgctaaatc ctagcagaca ctgccttgaa gcctcctgaa ttaactatca   4560

tcagtcctgc atttctttgg tggggggcca ggagggtgca tccaatttaa cttaactctt   4620

acctattttc tgcaggggat ctcagtcgac gagctc                              4656
```

<210> SEQ ID NO 15

<211> LENGTH: 4416
<212> TYPE: DNA
<213> ORGANISM: Artificial Sequence
<220> FEATURE:
<223> OTHER INFORMATION: Synthetic construct

<400> SEQUENCE: 15
atgcagatcg agctgagtac ctgctttttc ctctgcctgc tgcggttctg cttcagcgcc 60
acccggcggt actacctggg cgccgtggag ctgagttggg actacatgca gagcgacctg 120
ggcgagctgc ccgtggacgc ccggttcccc cctcgggtgc ccaagagctt ccccttcaac 180
accagcgtgg tgtacaagaa aaccctgttc gtggagttca ccgtgcacct gttcaacatc 240
gccaagccca ggccccccctg gatgggcctg ctgggcccca ccatccaggc cgaggtgtac 300
gacaccgtgg tgatcaccct gaagaacatg gccagccacc ccgtgagcct gcacgccgtg 360
ggcgtgagct actggaaggc cagtgagggc gccgagtacg acgaccagac cagccagcgg 420
gagaaagagg acgacaaggt tttccctggc ggcagccaca cctacgtgtg gcaggtcctg 480
aaagaaaacg gccccatggc ctccgacccc ctgtgcctga cctacagcta cctgagccac 540
gtggacctgg tcaaggacct gaacagcggc ctgatcggcg cgctgctggt ctgccgggag 600
ggcagcctgg ccaaagagaa aacccagacc ctgcacaagt tcatcctgct gttcgctgtg 660
ttcgacgagg gcaagagctg gcacagcgag accaagaaca gcctgatgca ggaccgggac 720
gccgccagcg ctcgcgcctg gcccaagatg cacaccgtga acggatacgt gaaccggtcc 780
ctgcccgggc tgatcggctg ccaccggaag agcgtgtact ggcacgtgat cggcatgggc 840
accacgcccg aggtgcacag catcttcctc gagggccaca ccttcctcgt gcggaaccac 900
cggcaggcca gcctcgagat cagccccatc accttcctca ccgcccagac gctgctgatg 960
gacctgggcc agttcctgct cttctgccac atcagctcgc accagcacga cggcatggaa 1020
gcctacgtga aggtggacag ttgccccgag gaaccccagc tgcggatgaa gaacaacgag 1080
gaagccgagg attacgacga cgacctgacc gacagcgaga tggacgtggt gcggttcgac 1140
gacgacaaca gccccagctt catccagatc cggtccgtgg ccaagaagca ccccaagacc 1200
tgggtgcact acatcgccgc cgaggaagag gactgggact acgccccccct ggtgctggcc 1260 cccgacgacc ggtcctacaa gagccagtac ctgaacaacg ggccccagcg gatcggccgg 1320
aagtacaaga aagtgcggtt catggcctac accgacgaga ccttcaagac ccgggaggcc 1380
atccagcacg agagcggcat cctgggcccc ctgctgtacg gcgaggtcgg cgacaccctg 1440
ctgatcatct tcaagaacca ggccagccgg ccctacaaca tctaccccca cggcatcacc 1500
gacgtgcggc ccctgtacag caggcggctg cccaagggcg tgaagcacct gaaggacttc 1560
cccatcctgc ccggcgagat cttcaagtac aagtggaccg tgaccgtgga ggacggcccc 1620
accaagagcg acccccgctg cctcacccgg tactacagca gcttcgtgaa catggagcgg 1680
gacctggcct ccggcctcat cggccccctg ctcatctgct acaaagaaag cgtggaccag 1740
cggggcaacc agatcatgag cgacaagcgg aacgtgatcc tgttctcggt gttcgacgag 1800
aaccggagtt ggtatctgac ggagaacatc cagcggttcc tccccaaccc tgccggcgtg 1860
cagctcgagg accccgagtt ccaggccagc aacatcatgc actccatcaa tggctacgtg 1920
ttcgacagcc tgcagctgtc cgtgtgcctc cacgaggtgg cctactggta catcctgagc 1980
atcggcgccc agaccgactt cctgagcgtg ttcttcagcg gctacacctt caagcacaag 2040
atggtgtacg aggacaccct gaccctgttc ccgttcagcg gcgagaccgt gttcatgagc 2100
atggaaaacc ccggcctgtg gatcctgggc tgccacaaca gcgacttccg gaaccggggc 2160

```
atgaccgccc tgctgaaggt gtccagctgc gacaagaaca ccggcgacta ctacgaggac   2220
agctacgagg acatcagcgc ctacctgctg tccaagaaca acgccatcga gccccggtcc   2280
ttcagccaga acagccggca ccccagcacc cggcagaagc agttcaacgc cacccccccct  2340
gtgctgaagc ggcaccagcg cgagatcacc cggaccaccc tgcagtccga ccaggaagag   2400
atcgactacg acgacaccat cagcgtggag atgaagaaag aggacttcga catctacgac   2460
gaggacgaga accagagccc ccgcagcttc cagaagaaaa cccggcacta cttcatcgcc   2520
gcggtggagc ggctgtggga ctacggcatg agcagcagcc cccacgtgct gcggaaccgg   2580
gcccagagcg gcagcgtgcc ccagttcaag aaagtggtgt tccaggaatt caccgacggc   2640
agcttcaccc agcccctgta ccggggcgag ctgaacgagc acctggggct gctggggccc   2700
tacatccgcg cggaggtgga ggacaacatc atggtgacct tccggaacca ggcctcccgc   2760
ccctactcct tctacagcag cctgatcagc tacgaagagg accagcggca gggcgcggag   2820
ccccggaaga acttcgtgaa gcccaacgag accaagacct acttctggaa ggtgcagcac   2880
cacatggccc ccaccaagga cgagttcgac tgcaaggcct gggcctactt cagcgacgtg   2940
gacctcgaga aggacgtgca ctccgggctc atcggcccgc tcctcgtgtg ccacaccaac   3000
accctgaacc ccgcccacgg ccggcaggtg accgtgcagg aattcgccct gttcttcacc   3060
atcttcgacg agaccaagtc gtggtacttc accgagaaca tggaacgcaa ctgcagggcc   3120
ccctgcaaca tccagatgga agatcccacc ttcaaagaga actaccggtt ccacgccatc   3180
aacggctaca tcatggacac cctgcccggc ctggtgatgg cccaggacca gcgcatccgg   3240
tggtatctgc tgtccatggg cagcaacgag aacatccaca gcatccactt cagcggccac   3300
gtgttcaccg tccggaagaa agaagagtac aagatggccc tgtacaacct gtaccccggc   3360
gtgttcgaga ccgtggagat gctgcccagc aaggccggca tctggcgggt ggagtgcctg   3420
atcggggagc acctccacgc cggcatgtcc accctgttcc tcgtgtacag caacaagtgc   3480
cagacccccc tgggcatggc cagcggccac atccgggact tccagatcac cgcctccggc   3540
cagtacggcc agtgggcccc caagctggcc cggctgcact acagcggcag catcaacgcc   3600
tggtccacca aagagccctt cagctggatc aaggtggacc tgctcgcccc catgatcatc   3660
cacgggatca agacccaggg cgccaggcag aagttcagca gcctgtacat cagccagttc   3720
atcatcatgt acagcctgga cggcaagaag tggcagacct accggggcaa cagcaccggc   3780
accctgatgg tgttcttcgg caacgtggac agcagcggca tcaagcacaa catcttcaac   3840
ccccccatca tcgcccggta catccggctg caccccaccc actacagcat ccggtccacc   3900
ctgcggatgg aactgatggg ctgcgacctg aactcctgca gcatgcccct ggggatggaa   3960
agcaaggcca tcagcgacgc ccagatcacg gccagcagct acttcaccaa catgttcgcc   4020
acctggtccc cctccaaggc ccgcctgcac ctgcagggcc ggtccaacgc ctggcggcct   4080
caggtcaaca accccaaaga gtggctgcag gttgacttcc agaaaaccat gaaggtgacc   4140
ggcgtgacca cccagggggt gaagagcctg ctgaccagca tgtacgtgaa agagttcctc   4200
atcagcagca gccaggacgg ccaccagtgg acgctgttct tccagaacgg caaggtcaag   4260
gtgttccagg gcaaccagga cagtttcacg cccgtggtga actccctgga cccccccctg   4320
ctgacccgct acctgcggat ccacccccag agctgggtcc accagatcgc cctgcgcatg   4380
gaagtcctcg gctgcgaggc gcaggacctg tactga                             4416
```

<210> SEQ ID NO 16
<211> LENGTH: 240
<212> TYPE: DNA

```
<213> ORGANISM: Artificial Sequence
<220> FEATURE:
<223> OTHER INFORMATION: Synthetic construct

<400> SEQUENCE: 16

ctcgaggggt ggccactgca gcacctgcca ctgccgtcac ctctccctcc tcagctccag     60

ggcagtgtcc ctccctggct tgccttctac ctttgtgcta aatcctagca gacactgcct    120

tgaagcctcc tgaattaact atcatcagtc ctgcatttct ttggtggggg gccaggaggg    180

tgcatccaat ttaacttaac tcttacctat tttctgcagg ggatctcagt cgacgagctc    240


<210> SEQ ID NO 17
<211> LENGTH: 2211
<212> TYPE: DNA
<213> ORGANISM: Artificial Sequence
<220> FEATURE:
<223> OTHER INFORMATION: Synthetic sequence

<400> SEQUENCE: 17

atggctgccg atggttatct tccagattgg ctcgaggaca ctctctctga aggaataaga     60

cagtggtgga agctcaaacc tggcccacca ccaccaaagc ccgcagagcg gcataaggac    120

gacagcaggg gtcttgtgct tcctgggtac aagtacctcg gacccttcaa cggactcgac    180

aagggagagc cggtcaacga ggcagacgcc gcggccctcg agcacgacaa agcctacgac    240

cggcagctcg acagcggaga caacccgtac ctcaagtaca accacgccga cgcggagttt    300

caggagcgcc ttaaagaaga tacgtctttt gggggcaacc tcggacgagc agtcttccag    360

gcgaaaaaga gggttcttga acctctgggc ctggttgagg aacctgttaa gacggctccg    420

ggaaaaaaga ggccggtaga gcactctcct gtggagccag actcctcctc gggaaccgga    480

aaggcgggcc agcagcctgc aagaaaaaga ttgaattttg gtcagactgg agacgcagac    540

tcagtacctg acccccagcc tctcggacag ccaccagcag ccccctctgg tctgggaact    600

aatacgatgg ctacaggcag tggcgcacca atggcagaca ataacgaggg cgccgacgga    660

gtgggtaatt cctcgggaaa ttggcattgc gattccacat ggatgggcga cagagtcatc    720

accaccagca cccgaacctg ggccctgccc acctacaaca accacctcta caaacaaatt    780

tccagcgctt caacgggagc ctcgaacgac aatcactact ttggctacag caccccttgg    840

gggtattttg acttcaacag attccactgc cacttttcac cacgtgactg gcaaagactc    900

atcaacaaca actggggatt ccgacccaag agactcaact tcaagctctt taacattcaa    960

gtcaaagagg tcacgcagaa tgacggtacg acgacgattg ccaataacct taccagcacg   1020

gttcaggtgt ttactgactc ggagtaccag ctcccgtacg tcctcggctc ggcgcatcaa   1080

ggatgcctcc cgccgttccc agcagacgtc ttcatggtgc cacagtatgg atacctcacc   1140

ctgaacaacg ggagtcaggc agtaggacgc tcttcatttt actgcctgga gtactttcct   1200

tctcagatgc tgcgtaccgg aaacaacttt accttcagct acacttttga ggacgttcct   1260

ttccacagca gctacgctca cagccagagt ctggaccgtc tcatgaatcc tctcatcgac   1320

cagtacctgt attacttgag cagaacaaac actccaagtg gaaccaccac gcagtcaagg   1380

cttcagtttt ctcaggccgg agcgagtgac attcgggacc agtctaggaa ctggcttcct   1440

ggaccctgtt accgccagca gcgagtatca aagacatctg cggataacaa caacagtgaa   1500

tactcgtgga ctggagctac caagtaccac ctcaatggca gagactctct ggtgaatccg   1560

ggcccggcca tggcaagcca caaggacgat gaagaaaagt tttttcctca gagcggggtt   1620

ctcatctttg ggaagcaagg ctcagagaaa acaaatgtgg acattgaaaa ggtcatgatt   1680
```

```
acagacgaag aggaaatcag gacaaccaat cccgtggcta cggagcagta tggttctgta   1740

tctaccaacc tccagagagg caacagacaa gcagctaccg cagatgtcaa cacacaaggc   1800

gttcttccag gcatggtctg gcaggacaga gatgtgtacc ttcaggggcc catctgggca   1860

aagattccac acacggacgg acattttcac ccctctcccc tcatgggtgg attcggactt   1920

aaacaccctc ctccacagat tctcatcaag aacaccccgg tacctgcgaa tccttcgacc   1980

accttcagtg cggcaaagtt tgcttccttc atcacacagt actccacggg acaggtcagc   2040

gtggagatcg agtgggagct gcagaaggaa aacagcaaac gctggaatcc cgaaattcag   2100

tacacttcca actacgccaa gtctgtcaat gtggacttta ctgtggacaa taatggcgtg   2160

tattcagagc ctcgccccat tggcaccaga tacctgactc gtaatctgta a            2211
```

```
<210> SEQ ID NO 18
<211> LENGTH: 1395
<212> TYPE: DNA
<213> ORGANISM: Artificial Sequence
<220> FEATURE:
<223> OTHER INFORMATION: Synthetic Construct

<400> SEQUENCE: 18

atgcagcgcg tgaacatgat catggcagaa tcaccaggcc tcatcaccat ctgcctttta     60

ggatatctac tcagtgctga atgtacagtt tttcttgatc atgaaaacgc caacaaaatt    120

ctgaatcggc caaagaggta taattcaggt aaattggaag agtttgttca agggaacctt    180

gagagagaat gtatggaaga aaagtgtagt tttgaagaag cacgagaagt ttttgaaaac    240

acggaaagaa caactgaatt ttggaagcag tatgttgatg gtgaccagtg tgagtccaat    300

ccatgtttaa atggcggcag ttgcaaggat gacattaatt cctatgaatg ttggtgtccc    360

tttggatttg aaggaaagaa ctgtgagctc gatgtaacat gtaacattaa gaatggcaga    420

tgcgagcagt tttgtaaaaa tagtgctgat aacaaggtgg tttgctcctg tactgaggga    480

tatcgacttg cagaaaacca gaagtcctgt gaaccagcag tgccatttcc atgcggccgc    540

gtttctgttt cacaaacttc taagctcacc cgtgctgaga ctgtttttcc tgatgtggac    600

tatgtaaatt ctactgaagc tgaaaccatt ttggataaca tcactcaaag cacccaatca    660

tttaatgact tcactcgggt tgttggtgga gaagatgcca aaccaggtca attcccttgg    720

caggttgttt tgaatggtaa agttgatgca ttctgtggag gctctatcgt taatgaaaaa    780

tggattgtaa ctgctgccca ctgtgttgaa actggtgtta aaattacagt tgtcgcaggt    840

gaacataata ttgaggagac agaacataca gagcaaaagc gaaatgtgat tcgaattatt    900

cctcaccaca actacaatgc agctattaat aagtacaacc atgacattgc ccttctggaa    960

ctggacgaac ccttagtgct aaacagctac gttacaccta tttgcattgc tgacaaggaa   1020

tacacgaaca tcttcctcaa atttggatct ggctatgtaa gtggctgggg aagagtcttc   1080

cacaaaggga gatcagcttt agttcttcag taccttagag ttccacttgt tgaccgagcc   1140

acatgtcttc gatctacaaa gttcaccatc tataacaaca tgttctgtgc tggcttccat   1200

gaaggaggta gagattcatg tcaaggagat agtgggggac cccatgttac tgaagtggaa   1260

gggaccagtt tcttaactgg aattattagc tggggtgaag agtgtgcaat gaaaggcaaa   1320

tatggaatat ataccaaggt atcccggtat gtcaactgga ttaaggaaaa aacaaagctc   1380

acttaatgag catgc                                                    1395

<210> SEQ ID NO 19
<211> LENGTH: 4650
<212> TYPE: DNA
```

<213> ORGANISM: Artificial Sequence
<220> FEATURE:
<223> OTHER INFORMATION: Synthetic Construct

<400> SEQUENCE: 19

```
atgcaaatag agctctccac ctgcttcttt ctgtgccttt tgcgattctg ctttagtgcc     60

accagaagat actacctggg tgcagtggaa ctgtcatggg actatatgca aagtgatctc    120

ggtgagctgc ctgtggacgc aagatttcct cctagagtgc caaaatcttt tccattcaac    180

acctcagtcg tgtacaaaaa gactctgttt gtagaattca cggttcacct tttcaacatc    240

gctaagccaa ggccaccctg gatgggtctg ctaggtccta ccatccaggc tgaggtttat    300

gatacagtgg tcattacact taagaacatg gcttcccatc ctgtcagtct tcatgctgtt    360

ggtgtatcct actggaaagc ttctgaggga gctgaatatg atgatcagac cagtcaaagg    420

gagaaagaag atgataaagt cttccctggt ggaagccata catatgtctg gcaggtcctg    480

aaagagaatg gtccaatggc ctctgaccca ctgtgcctta cctactcata tctttctcat    540

gtggacctgg taaaagactt gaattcaggc ctcattggag ccctactagt atgtagagaa    600

gggagtctgg ccaaggaaaa gacacagacc ttgcacaaat ttatactact ttttgctgta    660

tttgatgaag ggaaaagttg gcactcagaa acaaagaact ccttgatgca ggatagggat    720

gctgcatctg ctcgggcctg gcctaaaatg cacacagtca atggttatgt aaacaggtct    780

ctgccaggtc tgattggatg ccacaggaaa tcagtctatt ggcatgtgat tggaatgggc    840

accactcctg aagtgcactc aatattcctc gaaggtcaca catttcttgt gaggaaccat    900

cgccaggcgt ccttggaaat ctcgccaata actttcctta ctgctcaaac actcttgatg    960

gaccttggac agtttctact gttttgtcat atctcttccc accaacatga tggcatggaa   1020

gcttatgtca aagtagacag ctgtccagag gaaccccaac tacgaatgaa aaataatgaa   1080

gaagcggaag actatgatga tgatcttact gattctgaaa tggatgtggt caggtttgat   1140

gatgacaact ctccttcctt tatccaaatt cgctcagttg ccaagaagca tcctaaaact   1200

tgggtacatt acattgctgc tgaagaggag gactgggact atgctccctt agtcctcgcc   1260

cccgatgaca gaagttataa aagtcaatat ttgaacaatg gccctcagcg gattggtagg   1320

aagtacaaaa aagtccgatt tatggcatac acagatgaaa cctttaagac tcgtgaagct   1380

attcagcatg aatcaggaat cttgggacct ttactttatg gggaagttgg agacacactg   1440

ttgattatat ttaagaatca agcaagcaga ccatataaca tctaccctca cggaatcact   1500

gatgtccgtc ctttgtattc aaggagatta ccaaaaggtg taaaacattt gaaggatttt   1560

ccaattctgc caggagaaat attcaaatat aaatggacag tgactgtaga agatgggcca   1620

actaaatcag atcctcggtg cctgacccgc tattactcta gtttcgttaa tatggagaga   1680

gatctagctt caggactcat tggccctctc ctcatctgct acaaagaatc tgtagatcaa   1740

agaggaaacc agataatgtc agacaagagg aatgtcatcc tgttttctgt atttgatgag   1800

aaccgaagct ggtacctcac agagaatata caacgctttc tccccaatcc agctggagtg   1860

cagcttgagg atccagagtt ccaagcctcc aacatcatgc acagcatcaa tggctatgtt   1920

tttgatagtt tgcagttgtc agtttgtttg catgaggtgg catactggta cattctaagc   1980

attggagcac agactgactt cctttctgtc ttcttctctg gatatacctt caaacacaaa   2040

atggtctatg aagacacact caccctattc ccattctcag gagaaactgt cttcatgtcg   2100

atggaaaacc caggtctatg gattctgggg tgccacaact cagactttcg gaacagaggc   2160

atgaccgcct tactgaaggt ttctagttgt gacaagaaca ctggtgatta ttacgaggac   2220
```

```
agttatgaag atatttcagc atacttgctg agtaaaaaca atgccattga accaagaagc   2280
ttctcccaga attcaagaca ccctagcact aggcaaaagc aatttaatgc caccccacca   2340
gtcttgaaac gccatcaacg ggaaataact cgtactactc ttcagtcaga tcaagaggaa   2400
attgactatg atgataccat atcagttgaa atgaagaagg aagattttga catttatgat   2460
gaggatgaaa atcagagccc ccgcagcttt caaaagaaaa cacgacacta ttttattgct   2520
gcagtggaga ggctctggga ttatgggatg agtagctccc cacatgttct aagaaacagg   2580
gctcagagtg gcagtgtccc tcagttcaag aaagttgttt tccaggaatt tactgatggc   2640
tcctttactc agcccttata ccgtggagaa ctaaatgaac atttgggact cctggggcca   2700
tatataagag cagaagttga agataatatc atggtaactt tcagaaatca ggcctctcgt   2760
ccctattcct tctattctag ccttatttct tatgaggaag atcagaggca aggagcagaa   2820
cctagaaaaa actttgtcaa gcctaatgaa accaaaactt acttttggaa agtgcaacat   2880
catatggcac ccactaaaga tgagtttgac tgcaaagcct gggcttattt ctctgatgtt   2940
gacctggaaa aagatgtgca ctcaggcctg attggacccc ttctggtctg ccacactaac   3000
acactgaacc ctgctcatgg gagacaagtg acagtacagg aatttgctct gtttttcacc   3060
atctttgatg agaccaaaag ctggtacttc actgaaaata tggaaagaaa ctgcagggct   3120
ccctgcaata tccagatgga agatcccact tttaaagaga attatcgctt ccatgcaatc   3180
aatggctaca taatggatac actacctggc ttagtaatgg ctcaggatca aaggattcga   3240
tggtatctgc tcagcatggg cagcaatgaa aacatccatt ctattcattt cagtggacat   3300
gtgttcactg tacgaaaaaa agaggagtat aaaatggcac tgtacaatct ctatccaggt   3360
gtttttgaga cagtggaaat gttaccatcc aaagctggaa tttggcgggt ggaatgcctt   3420
attggcgagc atctacatgc tgggatgagc acactttttc tggtgtacag caataagtgt   3480
cagactcccc tgggaatggc ttctggacac attagagatt ttcagattac agcttcagga   3540
caatatggac agtgggcccc aaagctggcc agacttcatt attccggatc aatcaatgcc   3600
tggagcacca aggagccctt ttcttggatc aaggtggatc tgttggcacc aatgattatt   3660
cacggcatca agacccaggg tgcccgtcag aagttctcca gcctctacat ctctcagttt   3720
atcatcatgt atagtcttga tgggaagaag tggcagactt atcgaggaaa ttccactgga   3780
accttaatgg tcttctttgg caatgtggat tcatctggga taaaacacaa tatttttaac   3840
cctccaatta ttgctcgata catccgtttg cacccaactc attatagcat tcgcagcact   3900
cttcgcatgg agttgatggg ctgtgattta aatagttgca gcatgccatt gggaatggag   3960
agtaaagcaa tatcagatgc acagattact gcttcatcct actttaccaa tatgtttgcc   4020
acctggtctc cttcaaaagc tcgacttcac ctccaaggga ggagtaatgc ctggagacct   4080
caggtgaata atccaaaaga gtggctgcaa gtggacttcc agaagacaat gaaagtcaca   4140
ggagtaacta ctcagggagt aaaatctctg cttaccagca tgtatgtgaa ggagttcctc   4200
atctccagca gtcaagatgg ccatcagtgg actctctttt ttcagaatgg caaagtaaag   4260
gtttttcagg gaaatcaaga ctccttcaca cctgtggtga actctctaga cccaccgtta   4320
ctgactcgct accttcgaat tcacccccag agttgggtgc accagattgc cctgaggatg   4380
gaggttctgg gctgcgaggc acaggacctc tactgactcg aggggtggcc actgcagcac   4440
ctgccactgc cgtcacctct ccctcctcag ctccagggca gtgtccctcc ctggcttgcc   4500
```

-continued

```
ttctaccttt gtgctaaatc ctagcagaca ctgccttgaa gcctcctgaa ttaactatca   4560

tcagtcctgc atttctttgg tggggggcca ggagggtgca tccaatttaa cttaactctt   4620

acctattttc tgcaggggat ctcagtcgac                                     4650
```

MODIFIED FACTOR VIII AND FACTOR IX GENES AND VECTORS FOR GENE THERAPY

CROSS REFERENCE TO RELATED APPLICATIONS

The present application is filed under 35 U.S.C. §371 and claims priority to PCT Application No. PCT/US2007/071553 filed in the U.S. Patent and Trademark Office, PCT Division, on Jun. 19, 2007, which in turn claims priority from U.S. Provisional Patent Application Ser. No. 60/805,171, filed on Jun. 19, 2006, U.S. Provisional Patent Application Ser. No. 60/824,338, filed on Sep. 1, 2006, and U.S. Provisional Patent Application Ser. No. 60/847,337 was filed on Sep. 26, 2006; the contents of which are incorporated herein by reference in their entirety.

BACKGROUND OF THE INVENTION

1. Field of the Invention

The invention relates to modified Factor VIII (FVIII) and Factor XI (FIX) genes, nucleic acid vectors including the modified genes, optimized viral capsids including the modified genes, methods of using the modified genes in the treatment of FVIII and FIX deficiencies, such as hemophilia A and hemophilia B.

2. Discussion of Related Art

Hemophilia is a blood disorder in which the blood does not clot properly. Inadequate clotting causes excessive bleeding when the hemophiliac is injured. Hemophilia is a genetic coagulation disorder characterized by inadequate clotting and excessive bleeding. Several types of hereditary hemophilia are differentiated by the clotting factor affected. Hemophilia A is caused by a deficiency in blood coagulation Factor VIII (FVIII). Hemophilia B is caused by a deficiency in blood coagulation Factor IX (FIX).

Hemophilia B is an X-linked disorder and the condition affects ~1 in 30 000 males. In its severe form (about 60% of the Hemophilia B population) Hemophilia B can be fatal. Spontaneous hemorrhage into joints and muscles can lead to permanent disability.

Gene therapy has been proposed as treatment modality for supplementing deficiencies in clotting factors in hemophiliacs. However, as in many areas of gene therapy, theory is much more straightforward than successful, effective application. Many difficulties have been encountered in prior attempts to engineer FVIII or FIX constructs that are suitable for treatment of humans.

For example, Manno et al. reported AAV2 mediated delivery of FIX to the liver of human subjects in a Phase I study resulted in expression of biologically active FIX levels (Manno et al., Blood, (2006), pp.). Connelly et al. reported that treatment of FVIII-deficient mice with human FVIII-encoding adenoviral vectors resulted in expression of biologically active human FVIII (Connelly et al., Blood, Vol. 91, No. 9 (1998), pp. 3273-3281). Sarker et al. reported that use of AAV8 serotype in combination with FVIII corrected plasma FVIII activity in mouse models (Sarkar et al., Blood, Vol. 103, No. 4 (2004), pp. 1253-1260).

However, as in many areas of gene therapy, theory is much more straightforward than successful, effective implementation. Difficulties in implementation of gene therapy techniques include problems encountered in the use of viruses as gene vectors. While viruses are effective as gene vectors because they can be used to transduce cells leading to protein expression in vivo, the proteins coating the virus particle may activate the body's immune system.

Thus, there is therefore a need for systems which efficiently express the target protein in sufficient quantity to reduce the required dose of viral vector to tolerable levels.

SUMMARY OF THE INVENTION

The present invention provides for modified Factor VIII (FVIII) and Factor XI (FIX) genes, nucleic acid vectors including the modified genes, optimized viral capsids including the modified genes, and methods of using the modified genes in the treatment of FVIII and FIX deficiencies, such as hemophilia A and hemophilia B.

In one aspect, the present invention provides for optimized FVIII or FIX genes for treating hemophilia in a human subject wherein the optimized genes have been modified to increase CG sequences and reduce cis motifs. Preferably the optimized genes comprise sequences SEQ ID NO: 7, 12 or 15.

In another aspect, the present invention provides for a chimeric virus vector comprising optimized FVIII or FIX genes for treating hemophilia in a human subject wherein the optimized genes have been modified to increase CG sequences and reduce cis motifs. Preferably, the chimeric virus vector includes SEQ ID NO. 7 or its complement flanked by AAV TRs, such as SEQ ID NO. 2 and SEQ ID NO. 9, wherein the sequence of SEQ ID NO. 2 is at a 5' terminus and the SEQ ID NO. 9 at a 3' terminus thereof. The chimeric virus vector may comprise the nucleotide sequence of SEQ ID NO. 1.

In yet another aspect, the present invention provides for a method of treating hemophilia in a subject, the method comprising:

a. providing at least one recombinant virus vector comprising a nucleotide sequences for comprising a modified FVIII or FIX gene; and
b. administering the recombinant virus vector to the subject under conditions such that said FVIII or FIX nucleotide sequences are expressed at a level which produces a therapeutically effective amount of FVIII or FIX in the subject.

In a still further aspect, the present invention provides for a method of transducing a muscle cell or liver cell with a modified FVIII or FIX gene, the method comprising contacting the liver cell with a recombinant Biological Nano Particle (BNP) virus vector comprising an optimized FIX gene comprising the sequence of SEQ ID NO. 7 or an optimized FVIII gene comprising the sequence of SEQ ID NO: 12 or 15.

Gene transfer has substantial potential use in understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance that causes the disease or makes it more severe.

Thus, another aspect of the present invention provides for therapies to treat hemophilia, including: gene therapy based on administration of nucleotide sequence encoding for optimized FVIII or FIX genes.

In an alternative aspect, the present invention provides an expression vector comprising a polynucleotide that encodes an optimized FVIII or FIX gene or fragment thereof. In one embodiment the expression vector is an AVV virus vector including the sequence of AAV2 Capsid 2.5 (SEQ ID NO. 17)

In yet another aspect, the present invention provides a recombinant host cell transfected with a polynucleotide that encodes an optimized FVIII or FIX peptide of the present invention.

In a still further aspect, the present invention contemplates a process of preparing an optimized FVIII or FIX peptide or fragment thereof comprising;

a. transfecting a cell with polynucleotide that encodes the FVIII or FIX peptide or fragment thereof to produce a transformed host cell; and
b. maintaining the transformed host cell under biological conditions sufficient for expression of the peptide.

In another aspect, the present invention relates to the use of an optimized FVIII or FIX peptide or fragment thereof of the present invention in the use of a medicament for the treatment of hemophilia.

The present invention also provides for a pharmaceutical compositions comprising optimized FVIII or FIX genes for treating hemophilia in a human subject wherein the optimized genes have been modified to increase CG sequences and reduce cis motifs and in combination with a pharmaceutically acceptable carrier. The optimized genes may comprise sequences SEQ ID NOs: 7, 12 or 15.

Other features and advantages of the invention will be apparent from the following detailed description, drawings and claims.

BRIEF DESCRIPTION OF THE FIGURES

FIG. 15 shows the sequence of the vector (SEQ ID NO 1) of FIG. 14 and showing Bold Italic upper case: Left mutant ITR (SEQ ID NO: 2); Bold lower case: TTR promoter (SEQ ID NO: 3); Regular lower case: stuffer sequence (SEQ ID NO: 4); Bold underlined lower case: MVM intron (SEQ ID NO: 5); Regular lower case: stuffer sequence (SEQ ID NO: 6); Bold Italic Underlined upper case: optimized hFIX cDNA (SEQ ID NO: 7); Bold lower case: Bovine hormone polyA ((SEQ ID NO: 8) and Bold Italic upper case: Right ITR (SEQ ID NO: 9)

FIG. 16 shows the percentage of sequence codons falling into a certain quality class relative to SEQ ID NO: 19 (non-optimized) and SEQ ID NO: 12 (optimized).

FIG. 18 shows an increase in GC content from 44% (SEQ ID NO: 19) non-optimized to 60% optimized (SEQ ID NO: 12).

FIG. 22 show nucleotide sequence for modified FVIII gene SEQ ID NO: 10 including SEQ ID NO: 11, SEQ ID NO: 12 (modified FVIII cDNA) and SEQ ID NO: 13.

FIG. 23 shows nucleotide sequence for modified FVIII gene SEQ ID NO: 14 including SEQ ID NO: 15 (modified FVIII cDNA) and SEQ ID NO: 16.

FIG. 24 shows the comparison in CG content between the wild type FIX sequence (SEQ ID NO: 18) (Query line in Blast) and the optimized sequence (SEQ ID NO: 7) (Subject line in Blast) of the present invention.

DETAILED DESCRIPTION OF THE INVENTION

Definitions

Figure 1:
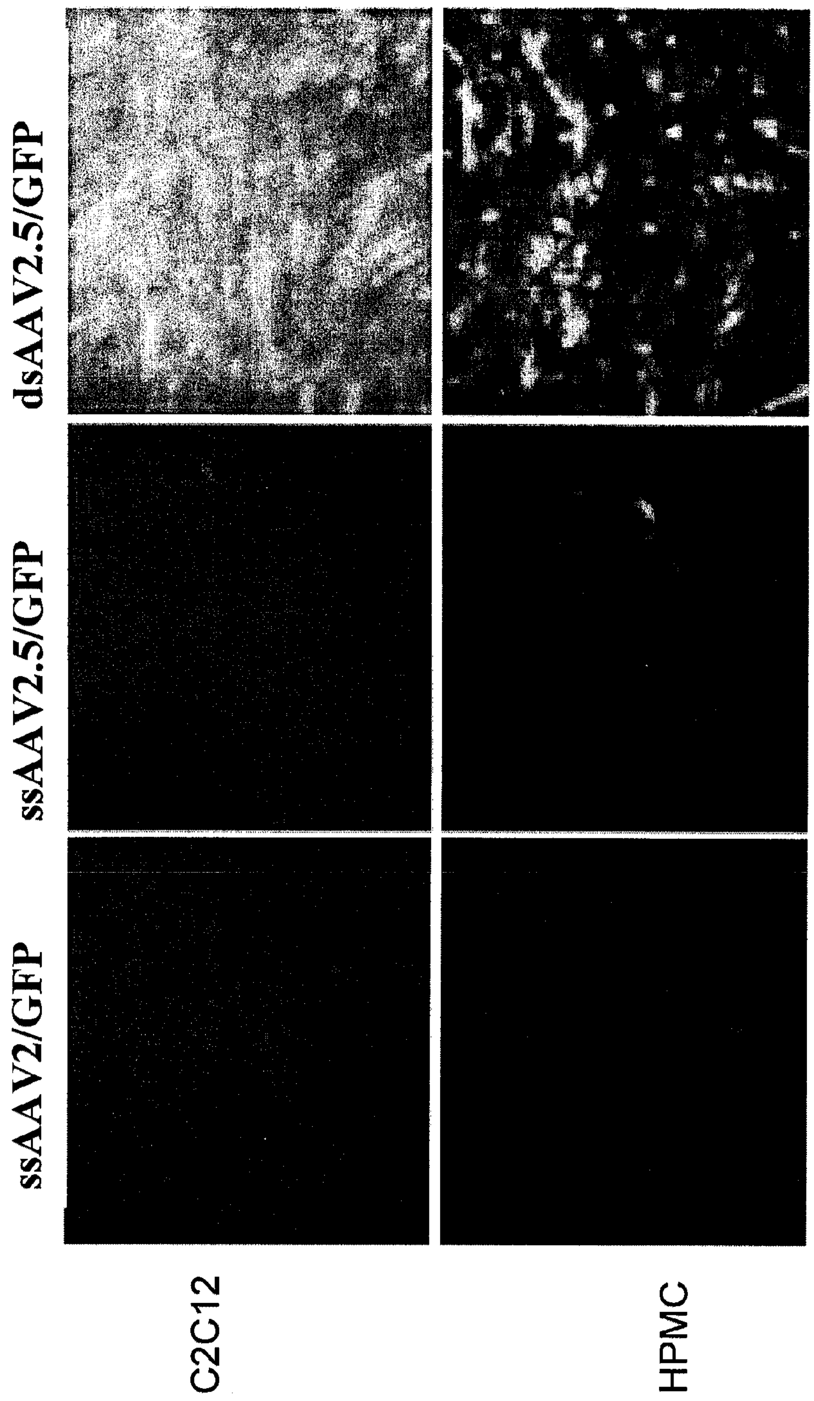
FIG. 1 shows in vitro GFP transduction $1\times10^9$ vg (viral genomes) HPMC 530,000 cells.

Unless otherwise defined, all technical and scientific terms used herein have the meaning commonly understood by one of ordinary skill in the art to which this invention belongs. The terminology used herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. The following terms have the meanings given:

"AAV Cap" means AAV Cap proteins, VP1, VP2 and VP3 and analogs thereof.

"AAV Rep" means AAV Rep proteins and analogs thereof.

"AAV TR" means a palindromic sequence, comprising mostly complementary, symmetrically arranged sequences, and includes analogs of native AAV TRs and analogs thereof.

"Biologically-effective" with respect to an amount of a viral vector is an amount that is sufficient to result in infection (or transduction) and expression of the transgene in a target cell.

"Cis-motifs" includes conserved sequences such as found at or close to the termini of the genomic sequence and recognized for initiation of replication; cryptic promoters or sequences at internal positions likely used for transcription initiation or termination.

"Chimeric" means, with respect to a viral capsid or particle, that the capsid or particle includes sequences from different parvoviruses, preferably different AAV serotypes, as described in Rabinowitz et al., U.S. Pat. No. 6,491,907, entitled "Recombinant parvovirus vectors and method of making," granted on Dec. 10, 2002, the disclosure of which is incorporated in its entirety herein by reference. A particularly preferred chimeric viral capsid is the AAV2.5 capsid, which has the sequence of the AAV2 capsid with the following mutations: 263 Q→A; 265 insertion T; 705 N→A; 708 V→A; and 716 T→N. wherein the nucleotide sequence expressing such capsid is defined as SEQ ID NO: 17. Additional preferred chimeric viral capsids are described in copending PCT Application No. PCT/US07/01668, the disclosure of which is incorporated in its entirety herein by reference.

"Flanked," with respect to a sequence that is flanked by other elements, indicates the presence of one or more the flanking elements upstream and/or downstream, i.e., 5' and/or 3', relative to the sequence. The term "flanked" is not intended to indicate that the sequences are necessarily contiguous. For example, there may be intervening sequences between the nucleic acid encoding the transgene and a flanking element. A sequence (e.g., a transgene) that is "flanked" by two other elements (e.g., TRs), indicates that one element is located 5' to the sequence and the other is located 3' to the sequence; however, there may be intervening sequences therebetween.

"Polynucleotide" means a sequence of nucleotides connected by phosphodiester linkages. Polynucleotides are presented herein in the direction from the 5' to the 3' direction. A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U). A polynucleotide of the present invention can be prepared using standard techniques well known to one of skill in the art.

"Transduction" of a cell by a virus means that there is transfer of DNA or RNA from the virus particle to the cell.

"Transfection" of a cell means that genetic material is introduced into a cell for the purpose of genetically modifying the cell. Transfection can be accomplished by a variety of means known in the art, such as transduction or electroporation.

"Polypeptide" encompasses both peptides and proteins, unless indicated otherwise.

"Transgene" is used in a broad sense to mean any heterologous nucleotide sequence incorporated in a viral vector for expression in a target cell and associated expression control sequences, such as promoters. It is appreciated by those of skill in the art that expression control sequences will be selected based on ability to promote expression of the transgene in the target cell. An example of a transgene is a nucleic acid encoding a therapeutic polypeptide.

"Vector," means a recombinant plasmid or virus that comprises a polynucleotide to be delivered into a host cell, either in vitro or in vivo.

"Recombinant" means a genetic entity distinct from that generally found in nature. As applied to a polynucleotide or gene, this means that the polynucleotide is the product of various combinations of cloning, restriction and/or ligation steps, and other procedures that result in the production of a construct that is distinct from a polynucleotide found in nature.

"Substantial homology" or "substantial similarity," means, when referring to a nucleic acid or fragment thereof, indicates that, when optimally aligned with appropriate nucleotide insertions or deletions with another nucleic acid (or its complementary strand), there is nucleotide sequence identity in at least about 95 to 99% of the sequence.

"Recombinant viral vector" means a recombinant polynucleotide vector comprising one or more heterologous sequences (i.e., polynucleotide sequence not of viral origin). In the case of recombinant parvovirus vectors, the recombinant polynucleotide is flanked by at least one, preferably two, inverted terminal repeat sequences (ITRs).

"Serotype" with respect to vector or virus capsid is defined by a distinct immunological profile based on the capsid protein sequences and capsid structure.

"Peptide", "polypeptide" and "protein" are used interchangeably to denote a sequence polymer of at least two amino acids covalently linked by an amide bond.

"Homologous" used in reference to peptides, refers to amino acid sequence similarity between two peptides. When an amino acid position in both of the peptides is occupied by identical amino acids, they are homologous at that position. Thus by "substantially homologous" means an amino acid sequence that is largely, but not entirely, homologous, and which retains most or all of the activity as the sequence to which it is homologous. As used herein, "substantially homologous" as used herein means that a sequence is at least 50% identical, and preferably at least 75% and more preferably 95% homology to the reference peptide. Additional peptide sequence modification are included, such as minor variations, deletions, substitutions or derivitizations of the amino acid sequence of the sequences disclosed herein, so long as the peptide has substantially the same activity or function as the unmodified peptides. Derivatives of an amino acid may include but not limited to trifluoroleucine, hexafluoroleucine, 5,5,5-trifluoroisoleucine, 4,4,4-trifluorovaline, p-fluorophenylaline, o-fluorotyrosine, m-fluorotyrosine, 2,3-difluorotyrosine, 4-fluorohistidine, 2-fluorohistidine, 2,4-difluorohistidine, fluoroproline, difluoroproline, 4-hydroxyproline, selenomethionine, telluromethionine, selenocysteine, selenatryptophans, 4-aminotryptophan, 5-aminotryptophan, 5-hydroxytryptophan, 7-azatryptophan, 4-fluorotryptophan, 5-fluorotryptophan, 6-fluorotryptophan, homoallylglycine, homopropargylglycine, 2-butynylglycine, cis-crotylglycine, allylglycine, dehydroleucine, dehydroproline, 2-amino-3-methyl-4-pentenoic acid, azidohomoalanine, asidoalanine, azidonorleucine, p-ethynylphenylalanine, p-azidophenylalanine, p-bromophenylalanine, p-acetylphenylalanine and benzofuranylalanine. Notably, a modified peptide will retain activity or function associated with the unmodified peptide, the modified peptide will generally have an amino acid sequence "substantially homologous" with the amino acid sequence of the unmodified sequence.

The invention provides modified nucleic acids encoding FVIII or FIX. The invention also provides nucleic acid constructs which include as part of their sequence the modified nucleic acid encoding FVIII or FIX. For example, the invention includes plasmids and/or other vectors that include the modified FVIII or FIX sequence along with other elements, such as regulatory elements. Further, the invention provides packaged gene delivery vehicle, such as a viral capsid, including the modified FVIII or FIX sequence. The invention also includes methods of expressing FVIII or FIX by delivering the modified sequence into a cell along with elements required to promote expression in the cell. The invention also provides gene therapy methods in which the modified FVIII or FIX sequence is administered to a subject, e.g., as a component of a vector and/or packaged as a component of a viral gene delivery vehicle. Treatment may, for example, be effected to enhance clotting in a subject and/or to treat a FVIII or FIX deficiency in the subject. Each of these aspects of the invention is discussed further in the ensuing sections.

Modified Nucleic Acid for Expression of FVIII or FIX

The invention provides a modified sequence encoding FVIII or FIX. The modified sequence includes the native FVIII or FIX sequence including one or more optimizing modifications. Examples of optimizing modifications include elimination of one or more cis-acting motifs and introduction of one or more Kozak sequences. In one embodiment, one or more cis-acting motifs are eliminated and one or more Kozak sequences are introduced.

Examples of cis acting motifs that may be eliminated include internal TATA-boxes; chi-sites; ribosomal entry sites; AT-rich and/or GC-rich sequence stretches; ARE, INS, and/or CRS sequence elements; repeat sequences and/or RNA secondary structures; (cryptic) splice donor and/or acceptor sites, branch points; and SalI. Preferably, GC content is enhanced relative to wild-type Factor FVIII or FIX and one or more cis-acting motifs are removed. The GC content is preferably at least 30 to 90% greater than the wild type gene. Additionally, the codon adaptation index is preferably >75, >80, >85, >90, or >95.

The modified FVIII or FIX sequence may also include flanking restriction sites to facilitate subcloning into expression vector.

The invention also includes fragments of the sequence of SEQ ID NO 7 which encode a functionally active fragment FIX. Further, the invention includes modified versions of SEQ ID NO: 7, which encode an analogue of FIX having FIX clotting activity. Additionally, the present application includes modified sequences for FVIII including SEQ ID NOs: 12 and 15.

The invention includes a nucleic acid vector including the modified FVIII or FIX sequence and various regulatory elements. The precise nature of regulatory elements useful for gene expression will vary from organism to organism. In general, they include a promoter which directs the initiation of RNA transcription in the cell of interest. The promoter may be constitutive or regulated. Constitutive promoters are those which cause an operably linked gene to be expressed essentially at all times. Regulated promoters are those which can be activated or deactivated. Regulated promoters include inducible promoters, which are usually "off" but which may be induced to turn "on," and "repressible" promoters, which are usually "on" but may be turned "off." Many different regulators are known, including temperature, hormones, cytokines, heavy metals and regulatory proteins. The distinctions are not absolute; a constitutive promoter may often be regulated to some degree. In some cases an endogenous pathway may be utilized to provide regulation of the transgene expression, e.g., using a promoter that is naturally downregulated when the pathological condition improves.

Examples of suitable promoters include adenoviral promoters, such as the adenoviral major late promoter; heterologous promoters, such as the cytomegalovirus (CMV) promoter; the respiratory syncytial virus promoter; the Rous Sarcoma Virus (RSV) promoter; the albumin promoter; inducible promoters, such as the Mouse Mammary Tumor Virus (MMTV) promoter; the metallothionein promoter; heat shock promoters; the α-1-antitrypsin promoter; the hepatitis B surface antigen promoter; the transferrin promoter; the apolipoprotein A-1 promoter; human FVIII promoters; and human FIX promoters. The promoter may be a tissue-specific promoter, such as the mouse albumin promoter, which is active in liver cells as well as the transthyretin promoter (TTR).

Packaged Modified FVIII or FIX Sequence

The modified FVIII or FIX sequence may also be provided as a component of a packaged viral vector. In general, packaged viral vectors include a viral vector packaged in a capsid. Viral vectors and viral capsids are discussed in the ensuing sections.

Viral Vector

The viral vector component of the packaged viral vectors produced according to the methods of the invention includes at least one modified FVIII or FIX sequence and associated expression control sequences for controlling expression of the modified FVIII or FIX sequence. The viral vector may include cis-acting functions sufficient to enable persistence as episomal forms or by mechanisms including integration of the modified FVIII or FIX sequence into the genome of a target cell.

In a preferred embodiment, the viral vector includes a portion of a parvovirus genome, such as an AAV genome with rep and cap deleted and replaced by the modified hFVIII or hFIX sequence and its associated expression control sequences. The modified FVIII or FIX sequence is typically inserted adjacent to one or two (i.e., flanked by) AAV TRs or TR elements adequate for viral replication; Xiao et al., J Virol 71; 2: 941-948 (1997), in place of the viral rep and cap ORFs. Other regulatory sequences suitable for use in facilitating tissue-specific expression of the modified hFVIII or hFIX sequence in the target cell may also be included.

The viral vector may be any suitable nucleic acid construct, such as a DNA or RNA construct and may be single stranded, double stranded, or duplexed.

Viral Capsid

The viral capsid component of the packaged viral vectors may be a parvovirus capsid. AAV Cap and chimeric capsids are preferred. Examples of suitable parvovirus viral capsid components are capsid components from the family Parvoviridae, such as an autonomous parvovirus or a Dependovirus. For example, the viral capsid may be an AAV capsid (e.g., AAV1, AAV2, AAV3, AAV4, AAV5, AAV6, AAV7, AAV8 AAV 9, AAV10, AAV 11 or AAV12 capsid; one skilled in the art would know there are likely other variants not yet identified that perform the same or similar function), or may include components from two or more AAV capsids. A full complement of AAV Cap proteins includes VP1, VP2, and VP3. The ORF comprising nucleotide sequences encoding AAV VP capsid proteins may comprise less than a full complement AAV Cap proteins or the full complement of AAV Cap proteins may be provided.

One or more of the AAV Cap proteins may be a chimeric protein, including amino acid sequences AAV Caps from two or more viruses, preferably two or more AAVs, as described in Rabinowitz et al., U.S. Pat. No. 6,491,907, entitled "Recombinant parvovirus vectors and method of making," granted on Dec. 10, 2002, the entire disclosure of which is incorporated herein by reference. For example, the chimeric virus capsid can include an AAV1 Cap protein or subunit and at least one AAV2 Cap or subunit. The chimeric capsid can, for example, include an AAV capsid with one or more B19 Cap subunits, e.g., an AAV Cap protein or subunit can be replaced by a B19 Cap protein or subunit. For example, in a preferred embodiment, the Vp3 subunit of the AAV capsid can be replaced by the Vp2 subunit of B19.

Production of Packaged Viral Vector

The invention includes packaging cells which may be cultured to produce packaged viral vectors of the invention. The packaging cells of the invention generally include cells with heterologous (1) viral vector function(s), (2) packaging function(s), and (3) helper function(s). Each of these component functions is discussed in the ensuing sections.

Viral Vector Functions

The packaging cells of the invention include viral vector functions, along with packaging and vector functions. The viral vector functions typically include a portion of a parvovirus genome, such as an AAV genome, with rep and cap deleted and replaced by the modified FVIII or FIX sequence and its associated expression control sequences. The viral vector functions include sufficient expression control sequences to result in replication of the viral vector for packaging. Typically, the viral vector includes a portion of a parvovirus genome, such as an AAV genome with rep and cap deleted and replaced by the transgene and its associated expression control sequences. The transgene is typically flanked by two AAV TRs, in place of the deleted viral rep and cap ORFs. Appropriate expression control sequences are included, such as a tissue-specific promoter and other regulatory sequences suitable for use in facilitating tissue-specific expression of the transgene in the target cell. The transgene is typically a nucleic acid sequence that can be expressed to produce a therapeutic polypeptide or a marker polypeptide. The viral vector may be any suitable nucleic acid construct, such as a DNA or RNA construct and may be single stranded, double stranded, or duplexed.

The viral vector functions may suitably be provided as duplexed vector templates, as described in U.S. Patent Publication No. 2004/0029106 to Samulski et al. (the entire disclosure of which is incorporated herein by reference for its teaching regarding duplexed vectors). Duplexed vectors are dimeric self-complementary (sc) polynucleotides (typically, DNA). For example, the DNA of the duplexed vectors can be selected so as to form a double-stranded hairpin structure due to intrastrand base pairing. Both strands of the duplexed DNA vectors may be packaged within a viral capsid. The duplexed vector provides a function comparable to double-stranded DNA virus vectors and can alleviate the need of the target cell to synthesize complementary DNA to the single-stranded genome normally encapsidated by the virus.

The TR(s) (resolvable and non-resolvable) selected for use in the viral vectors are preferably AAV sequences, with serotypes 1, 2, 3, 4, 5 and 6 being preferred. Resolvable AAV TRs need not have a wild-type TR sequence (e.g., a wild-type sequence may be altered by insertion, deletion, truncation or missense mutations), as long as the TR mediates the desired functions, e.g., virus packaging, integration, and/or provirus rescue, and the like. The TRs may be synthetic sequences that function as AAV inverted terminal repeats, such as the "double-D sequence" as described in U.S. Pat. No. 5,478,745 to Samulski et al., the entire disclosure of which is incorporated in its entirety herein by reference. Typically, but not necessarily, the TRs are from the same parvovirus, e.g., both TR sequences are from AAV2

The packaging functions include capsid components. The capsid components are preferably from a parvoviral capsid, such as an AAV capsid or a chimeric AAV capsid function. Examples of suitable parvovirus viral capsid components are capsid components from the family Parvoviridae, such as an autonomous parvovirus or a Dependovirus. For example, the capsid components may be selected from AAV capsids, e.g., AAV1-AAV12 and other novel capsids as yet unidentified or from non human primate sources. Capsid components may include components from two or more AAV capsids.

In a more preferred embodiment, one or more of the VP capsid proteins is a chimeric protein, comprising amino acid sequences from two or more viruses, preferably two or more AAVs, as described in Rabinowitz et al., U.S. Pat. No. 6,491,907, entitled "Recombinant parvovirus vectors and method of making," granted on Dec. 10, 2002, the entire disclosure of which is incorporated in its entirety herein by reference.

For example, the chimeric virus capsid can include a capsid region from an adeno-associated virus (AAV) and at least one capsid region from a B19 virus. The chimeric capsid can, for example, include an AAV capsid with one or more B19 capsid subunits, e.g., an AAV capsid subunit can be replaced by a B19 capsid subunit. For example, in a preferred embodiment, the VP1, VP2 or VP3 subunit of the AAV capsid can be replaced by the VP1, VP2 or VP3 subunit of B19. As another example, the chimeric capsid may include an AAV type 2 capsid in which the type 2 VP1 subunit has been replaced by the VP1 subunit from an AAV type 1, 3, 4, 5, or 6 capsid, preferably a type 3, 4, or 5 capsid. Alternatively, the chimeric parvovirus has an AAV type 2 capsid in which the type 2 VP2 subunit has been replaced by the VP2 subunit from an AAV type 1, 3, 4, 5, or 6 capsid, preferably a type 3, 4, or 5 capsid Likewise, chimeric parvoviruses in which the VP3 subunit from an AAV type 1, 3, 4, 5 or 6 (more preferably, type 3, 4 or 5) is substituted for the VP3 subunit of an AAV type 2 capsid are preferred. As a further alternative, chimeric parvoviruses in which two of the AAV type 2 subunits are replaced by the subunits from an AAV of a different serotype (e.g., AAV type 1, 3, 4, 5 or 6) are preferred. In exemplary chimeric parvoviruses according to this embodiment, the VP1 and VP2, or VP1 and VP3, or VP2 and VP3 subunits of an AAV type 2 capsid are replaced by the corresponding subunits of an AAV of a different serotype (e.g., AAV type 1, 3, 4, 5 or 6). Likewise, in other preferred embodiments, the chimeric parvovirus has an AAV type 1, 3, 4, 5 or 6 capsid (preferably the type 2, 3 or 5 capsid) in which one or two subunits have been replaced with those from an AAV of a different serotype, as described above for AAV type 2.

The packaged viral vector generally includes the modified FVIII or FIX sequence and expression control sequences flanked by TR elements sufficient to result in packaging of the vector DNA and subsequent expression of the modified FVIII or FIX sequence in the transduced cell. The viral vector functions may, for example, be supplied to the cell as a component of a plasmid or an amplicon. The viral vector functions may exist extrachromosomally within the cell line and/or may be integrated into the cells' chromosomal DNA.

Any method of introducing the nucleotide sequence carrying the viral vector functions into a cellular host for replication and packaging may be employed, including but not limited to, electroporation, calcium phosphate precipitation, microinjection, cationic or anionic liposomes, and liposomes in combination with a nuclear localization signal. In embodiments wherein the viral vector functions are provided by transfection using a virus vector; standard methods for producing viral infection may be used.

Packaging Functions

The packaging functions include genes for viral vector replication and packaging. Thus, for example, the packaging functions may include, as needed, functions necessary for viral gene expression, viral vector replication, rescue of the viral vector from the integrated state, viral gene expression, and packaging of the viral vector into a viral particle. The packaging functions may be supplied together or separately to the packaging cell using a genetic construct such as a plasmid or an amplicon. The packaging functions may exist extrachromosomally within the packaging cell, but are preferably integrated into the cell's chromosomal DNA. Examples include genes encoding AAV Rep and Cap proteins.

Helper Functions

The helper functions include helper virus elements needed for establishing active infection of the packaging cell, which is required to initiate packaging of the viral vector. Examples include functions derived from adenovirus, baculovirus and/or herpes virus sufficient to result in packaging of the viral vector. For example, adenovirus helper functions will typically include adenovirus components E1a, E1b, E2a, E4, and VA RNA. The packaging functions may be supplied by infection of the packaging cell with the required virus. The packaging functions may be supplied together or separately to the packaging cell using a genetic construct such as a plasmid or an amplicon. The packaging functions may exist extrachromosomally within the packaging cell, but are preferably integrated into the cell's chromosomal DNA.

Any suitable helper virus functions may be employed. For example, where the packaging cells are insect cells, baculovirus may serve as a helper virus. Herpes virus may also be used as a helper virus in AAV packaging methods. Hybrid herpes viruses encoding the AAV Rep protein(s) may advantageously facilitate for more scalable AAV vector production schemes.

Any method of introducing the nucleotide sequence carrying the helper functions into a cellular host for replication and packaging may be employed, including but not limited to, electroporation, calcium phosphate precipitation, microinjection, cationic or anionic liposomes, and liposomes in combination with a nuclear localization signal. In embodiments wherein the helper functions are provided by transfection using a virus vector or infection using a helper virus; standard methods for producing viral infection may be used.

Packaging Cell

Any suitable permissive or packaging cell known in the art may be employed in the production of the packaged viral vector. Mammalian cells or insect cells are preferred. Examples of cells useful for the production of packaging cells in the practice of the invention include, for example, human cell lines, such as VERO, WI38, MRC5, A549, 293 cells, B-50 or any other HeLa cells, HepG2, Saos-2, HuH7, and HT1080 cell lines.

Preferred cell lines for use as packaging cells are insect cell lines. Any insect cell which allows for replication of AAV and which can be maintained in culture can be used in accordance with the present invention. Examples include *Spodoptera frugiperda*, such as the Sf9 or Sf21 cell lines, *Drosophila* spp. cell lines, or mosquito cell lines, e.g., *Aedes albopictus* derived cell lines. A preferred cell line is the *Spodoptera frugiperda* Sf9 cell line. The following references are incorporated herein for their teachings concerning use of insect cells for expression of heterologous polypeptides, methods of introducing nucleic acids into such cells, and methods of maintaining such cells in culture: Methods in Molecular Biology, ed. Richard, Humana Press, NJ (1995); O'Reilly et al., Baculovirus Expression Vectors: A Laboratory Manual, Oxford Univ. Press (1994); Samulski et al., *J. Vir.* 63:3822-8 (1989); Kajigaya et al., *Proc. Nat'l. Acad. Sci. USA* 88: 4646-50 (1991); Ruffing et al., *J. Vir.* 66:6922-30 (1992); Kimbauer et al., *Vir.* 219:37-44 (1996); Zhao et al., *Vir.* 272:382-93 (2000); and Samulski et al., U.S. Pat. No. 6,204,059.

During production, the packaging cells generally include one or more viral vector functions along with helper functions and packaging functions sufficient to result in replication and packaging of the viral vector. These various functions may be supplied together or separately to the packaging cell using a genetic construct such as a plasmid or an amplicon, and they may exist extrachromosomally within the cell line or integrated into the cell's chromosomes.

The cells may be supplied with any one or more of the stated functions already incorporated, e.g., a cell line with one or more vector functions incorporated extrachromosomally or integrated into the cell's chromosomal DNA, a cell line with one or more packaging functions incorporated extrachromosomally or integrated into the cell's chromosomal DNA, or a cell line with helper functions incorporated extrachromosomally or integrated into the cell's chromosomal DNA.

Treatment Methods

The modified FVIII or FIX gene may be used for gene therapy of FVIII or FIX associated disorders, such as hemophilia A or B. An individual may be in need of gene therapy because, as a result of one or more mutations in the regulatory region and/or the coding sequence of the FVIII or FIX gene, FVIII or FIX is expressed inappropriately, e.g., has an incorrect amino acid sequence, or is expressed in the wrong tissues or at the wrong times, is underexpressed or overexpressed. The modified FVIII or FIX gene may be used as gene therapy to enhance clotting in a subject in need of enhanced clotting.

The target cells of the vectors of the instant invention are cells capable of expressing polypeptides with FVIII or FIX activity, such as those of the hepatic system of a mammal, endothelial cells and other cells with the proper cellular machinery to process the precursor to yield protein with FVIII or FIX activity. In one embodiment, the cells are normal cells cultured in vitro. The target cells may, for example, be human cells, or cells of other mammals, especially non-human primates and mammals of the orders Rodenta (mice, rats, rabbit and hamsters), Carnivora (cats and dogs) and Arteriodactyla (cows, pigs, sheep, goats and horses). Any cell type may be targeted. In some cases any cell type except muscle cells may be targeted.

In particular embodiments, the present invention provides a pharmaceutical composition comprising a vector of the present invention including a modified gene of FVIII or FIX in a pharmaceutically-acceptable carrier and/or other medicinal agents, pharmaceutical agents, carriers, adjuvants, diluents, etc. For injection, the carrier will typically be a liquid. For other methods of administration, the carrier may be either solid or liquid. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

Exemplary pharmaceutically acceptable carriers include sterile, pyrogen-free water and sterile, pyrogen-free, phosphate buffered saline. Physiologically-acceptable carriers include pharmaceutically-acceptable carriers. Pharmaceutically acceptable carriers are those which are that is not biologically or otherwise undesirable, i.e., the material may be administered to a subject without causing undesirable biological effects which outweigh the advantageous biological effects of the material.

A pharmaceutical composition may be used, for example, in transfection of a cell ex vivo or in administering a viral vector or cell directly to a subject.

Recombinant virus vectors comprising the modified gene of FVIII or FIX are preferably administered to the cell in a biologically-effective amount. If the virus vector is administered to a cell in vivo (e.g., the virus is administered to a subject as described below), a biologically-effective amount of the virus vector is an amount that is sufficient to result in transduction and expression of the transgene in a target cell.

The cells transduced with a viral vector are preferably administered to the subject in a "therapeutically-effective amount" in combination with a pharmaceutical carrier. Those skilled in the art will appreciate that the therapeutic effects need not be complete or curative, as long as some benefit is provided to the subject.

Dosages of the cells to administer to a subject will vary upon the age, condition and species of the subject, the type of cell, the nucleic acid being expressed by the cell, the mode of administration, and the like. Typically, at least about $10^2$ to about $10^8$, preferably about $10^3$ to about $10^8$ cells, will be administered per dose. Preferably, the cells will be administered in a therapeutically-effective amount.

A further aspect of the invention is a method of treating subjects in vivo with the vector containing modified genes. Administration of the vector to a human subject or an animal in need thereof can be by any means known in the art for administering virus vectors.

Exemplary modes of administration include rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspension in liquid prior to injection, or as emulsions. Alternatively, one may administer the virus in a local rather than systemic manner, for example, in a depot or sustained-release formulation.

In other preferred embodiments, the inventive vector comprising the modified FVIII or FIX gene is administered intramuscularly, more preferably by intramuscular injection or by local administration. The vectors disclosed herein may be administered to the lungs of a subject by any suitable means, but are preferably administered by administering an aerosol suspension of respirable particles comprised of the inventive parvovirus vectors, which the subject inhales. The respirable particles may be liquid or solid. Aerosols of liquid particles comprising the inventive parvovirus vectors may be produced by any suitable means, such as with a pressure-driven aerosol nebulizer or an ultrasonic nebulizer, as is known to those of skill in the art. See, e.g., U.S. Pat. No. 4,501,729.

Dosages of the inventive virus vector with the modified FVIII or FIX gene will depend upon the mode of administration, the disease or condition to be treated, the individual subject's condition, the particular viral vector, and the gene to be delivered, and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$ transducing units or more, preferably about $10^8$-$10^{13}$ transducing units, yet more preferably $10^{12}$ transducing units.

The modified FVIII or FIX genes may be administered as components of a DNA molecule having regulatory elements appropriate for expression in the target cells. The modified FVIII or FIX genes may be administered as components of viral plasmids, such as rAAV vectors. Viral particles may be administered as viral particles alone, whether as an in vivo direct delivery to the portal vasculature or as an ex vivo treatment comprising administering the vector viral particles in vitro to cells from the animal receiving treatment followed by introduction of the transduced cells back into the donor.

EXAMPLES

The results of this rodent feasibility study confirm the superiority of both double stranded vectors and liver mediated FIX gene therapy at doses 10 to 100 fold below those established to be safe in human clinical trial using AAV2.

AAV2 and BNP2.5 Infect Primary Human Skeletal Muscle

FIG. 1 shows in vitro GFP transduction $1\times10^9$ vg HPMC 530,000 cells using the different vectors including the AAV2 and chimeric virus vector BNP2.5 having the sequence set forth in SEQ ID NO. 17. Primary human skeletal muscle cell were tested by immunofluorescence for vWF/Factor IX, smooth muscle alpha-actin, and sarcomeric myosin to ensure purity (i.e. neg., neg., & positive respectively). Only cells that were negative for bacteria, fungi, mycoplasm, HIV DNA, and Hepatitis B & C DNA were considered for vector transduction. These cells were established in trans-well tissue culture conditions after second passage isolation to promote well-differentiated striated muscle. 60 to 80% confluent monolayers were infected using dose escalation from MOI of 1 to 100/cell (total $1\times10^4$) and GFP reporter transgene (FIG. 1).

Figure 2:
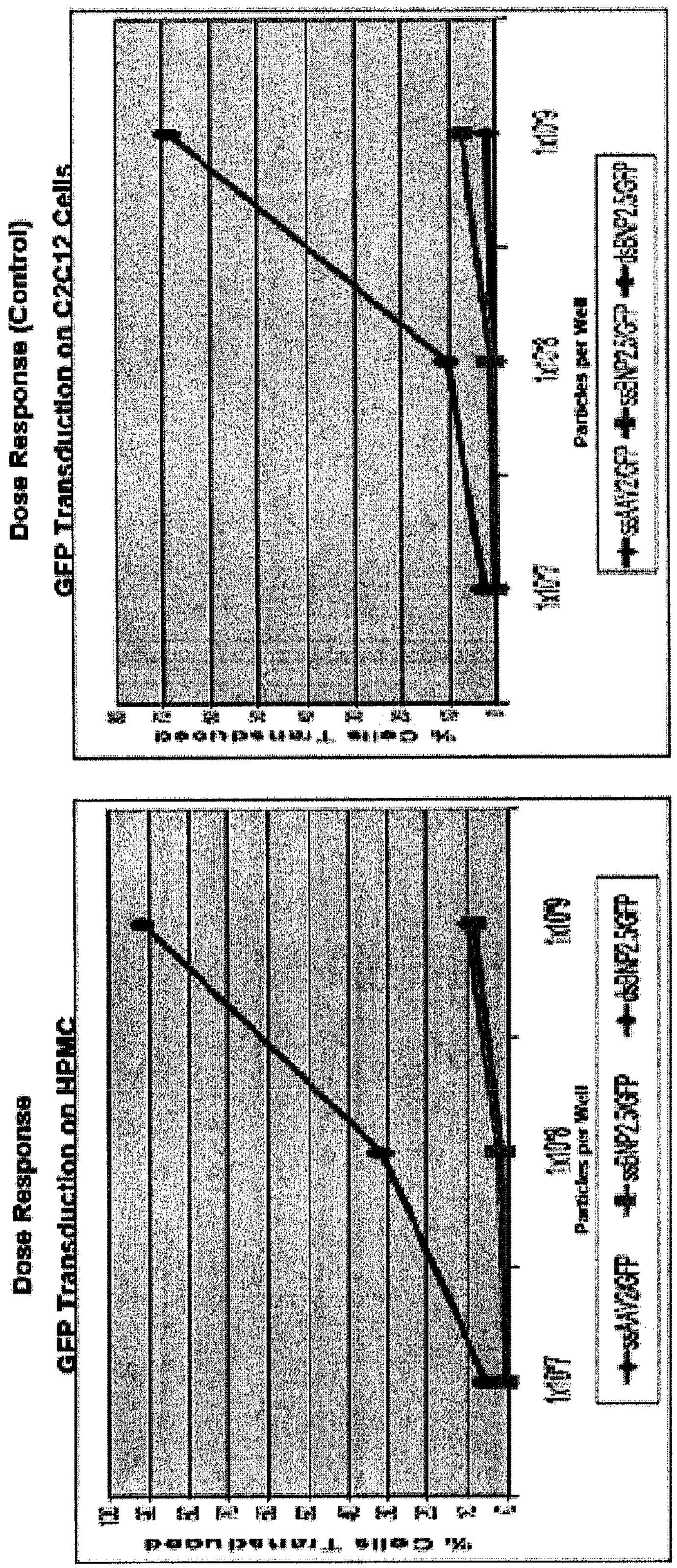
FIG. 2 shows in vitro GFP does response of single and double stranded genome.

FIG. 2 shows in vitro GFP dose response single vs. double stranded genome. Cells were monitored over time and percent positive tabulated compared to control. These GFP results are compared to primary mouse skeletal cells transduced under identical conditions as a positive control. Positive transduction indicated here (FIG. 2) shows that human skeletal muscle cells are permissive to vector infection.

Vector Expressed Transgene Secretes from Primary Human Skeletal Muscle

Key to these studies is the ability to determine if human FIX transgene can be secreted from primary human skeletal muscle. Two methods have been employed to determine if human FIX transgene is successfully secreted from target cells after vector administration. ELISA was used to determine the total amount of FIX antigen, and activated partial thromboplastin time (APTT) to determine functional activity. In transformed tissue culture cells, peak FIX expression was determined to occur 24 hours after vector transduction. Cell media was removed and analyzed for FIX every 24 hours until transgene expression plateau.

Figure 3:
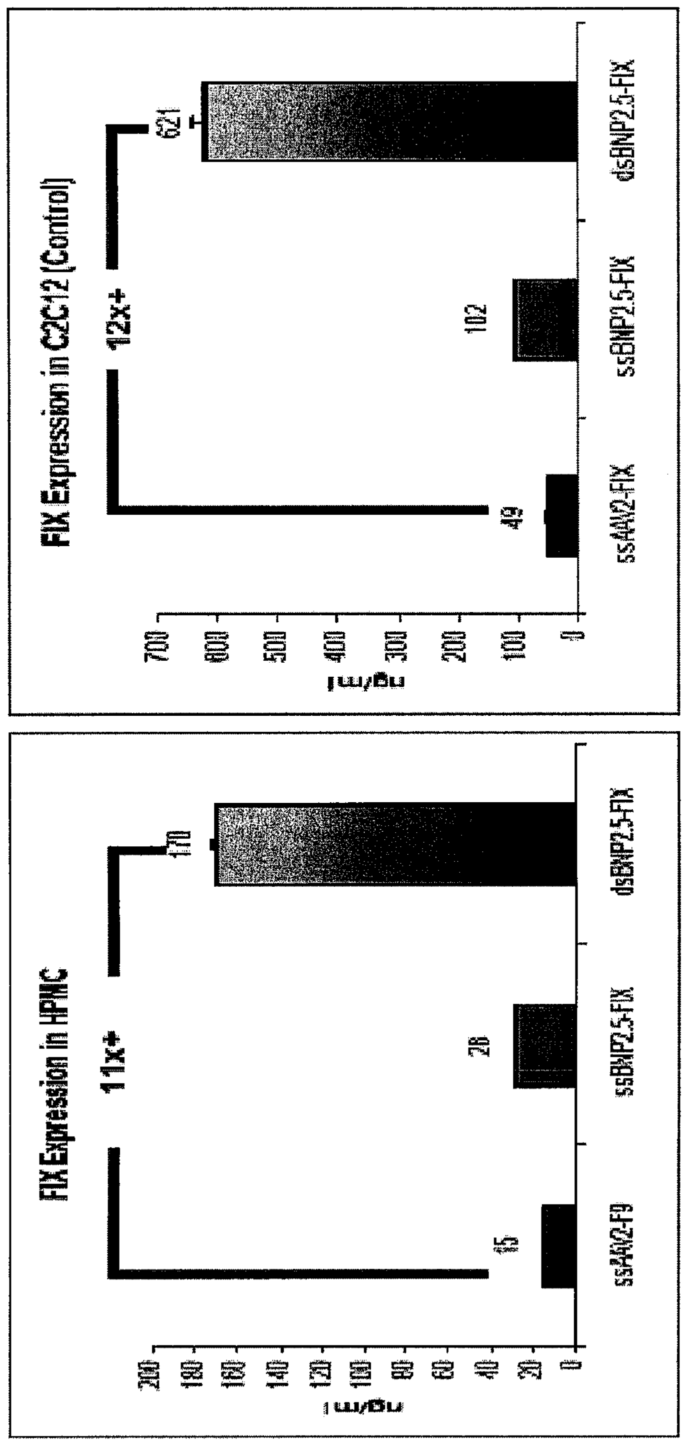
FIG. 3 shows the level of expression from primary and human primary skeletal muscle cell line.
Figure 4:
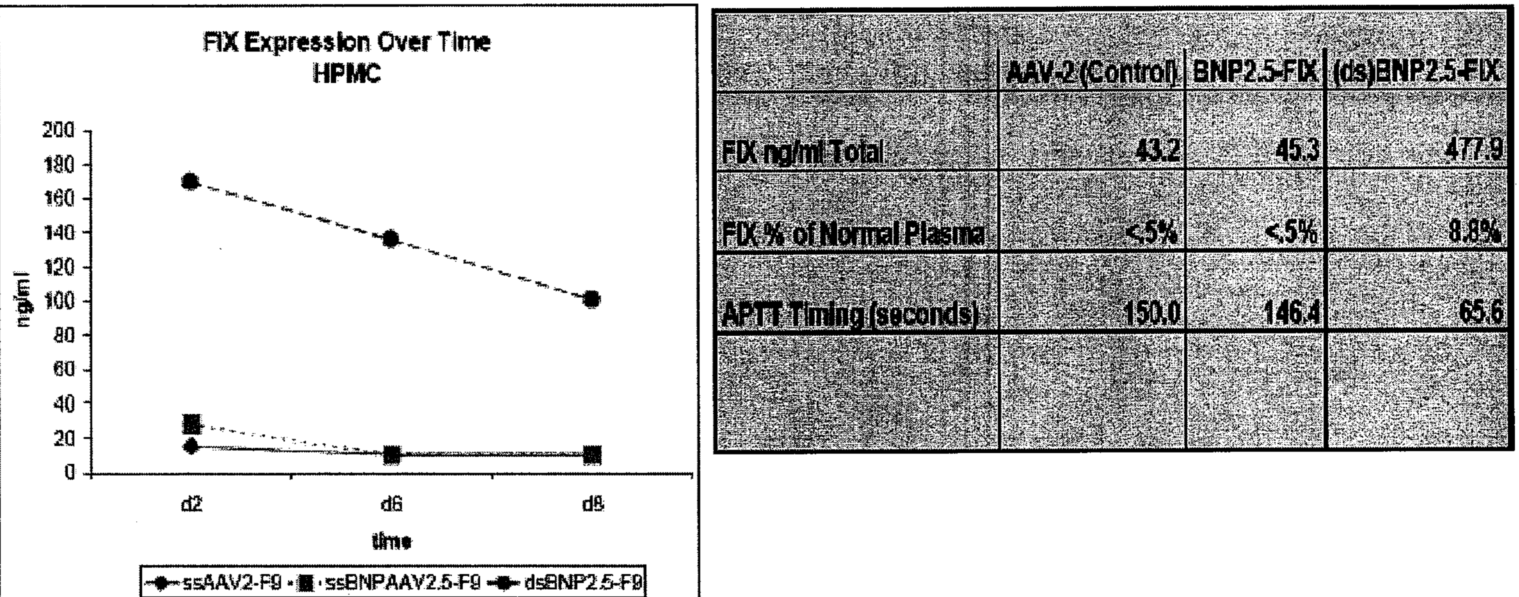
FIG. 4 shows APTT HPMC in vitro lysate from $1\times10^9$ vg/titer infection 24 hours post infection.

The levels of expression from primary mouse and human primary skeletal muscle cell line supernatant were compared (FIG. 3) and the functional activity of the transgene was measured. (FIG. 4). These positive results support a conclusion that human skeletal muscle can secrete vector derived FIX transgene.

FIG. 4 shows APTT HPMC in vitro lysate from $1\times10^9$ vg/titer infection 24 hours post infection. BNP2.5 expresses 2 fold higher levels of secreted FIX from primary human skeletal muscle.

Figure 5:
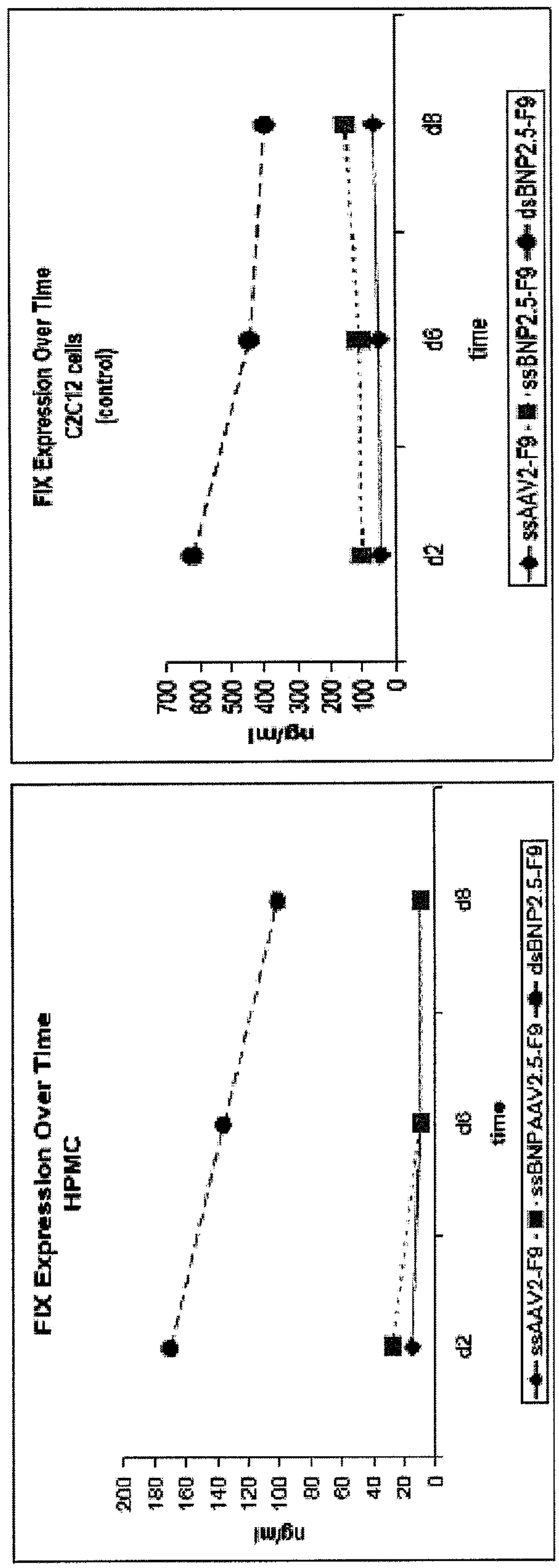
FIG. 5 shows hFIX in vitro HPMC cell lysate expression.

FIG. 5 shows hFIX in vitro HPMC cell lysate expression. BNP2.5 was evaluated with ELISA every 24 hours tested for increased expression of human FIX transgene from human skeletal muscle after vector transduction (FIG. 5) as described above. These positive results show that human skeletal muscle can secrete vector derived FIX transgene and that BNP2.5 is more efficient than AAV2 in both human and mouse primary cells.

AAV2 vs. BNPdsFIX in Hemophilic Mouse Model R333Q for Level and Duration of Transgene Expression Recent development of hemophilia B knockout mouse models (FIXKO mouse) has reproduced the bleeding phenotype of human hemophilia B, but because these models produce no FIX, they fail to reproduce the dominant human phenotype. In addition, treatment of these models with vectors expressing FIX transgene typically results in development of antibodies making long-term efficacy studies impossible. Recent development of human FIX mouse model R333Q-hFIX at the University of North Carolina at Chapel Hill has resulted in a model that mimics mutation observed in humans (mis-sense mutation). These animals express mRNA transcripts and circulating human FIX detectable throughout development, but with FIX activity less than 1%. R333Q mutation was chosen because data has been reported on several patients with severe hemophilia B who exhibit this mutation. Moreover, these CRM+ patients have nearly normal levels of FIX antigen and their clotting activity is usually less than 1%. The R333Q-hFIX mice are not morphologically different from wild-type mice. They survive well if no injury occurs and have litters of 4-8 pups with a sex ratio of approximately 1:1. These animals display identical bleeding phenotype to that observed in humans, making them ideal models for studying gene therapy approaches for hemophilia B deficiency. In addition human FIX R333Q gene was expressed as the alanine form of the Ala 148 Thr dimorphism. Because A-1 antibody binds well to the FIX with the threonine at residue 148 and weakly to the alanine isoform, vectors expressing the threonine isoform can readily be detected.

Animals 8-10 weeks of age have been used for this study (FIG. 6), in which three vector doses have been tested. R333Q mice (n=5/cohort) and normal parent animals C57BL6 have been injected 1M with AAV2 and BNP2.5ds expressing hFIX (FIG. 6). A cohort of BNP2.5(ss)-FIX-CMV has been added to the design to evaluate vector capsid tropism significance. Levels of FIX protein expression and transgene activity were measured over time as described by Jin et. al., Blood 2004. Measurements of time points every two weeks after vector administration were carried out past six weeks. APTT assay has been utilized to determine activity of vector delivered transgene and compared to control. Lack of antibody formation as indicated by Bethesda inhibition assay has been carried out on a sub-set of animals.

Figure 6A:
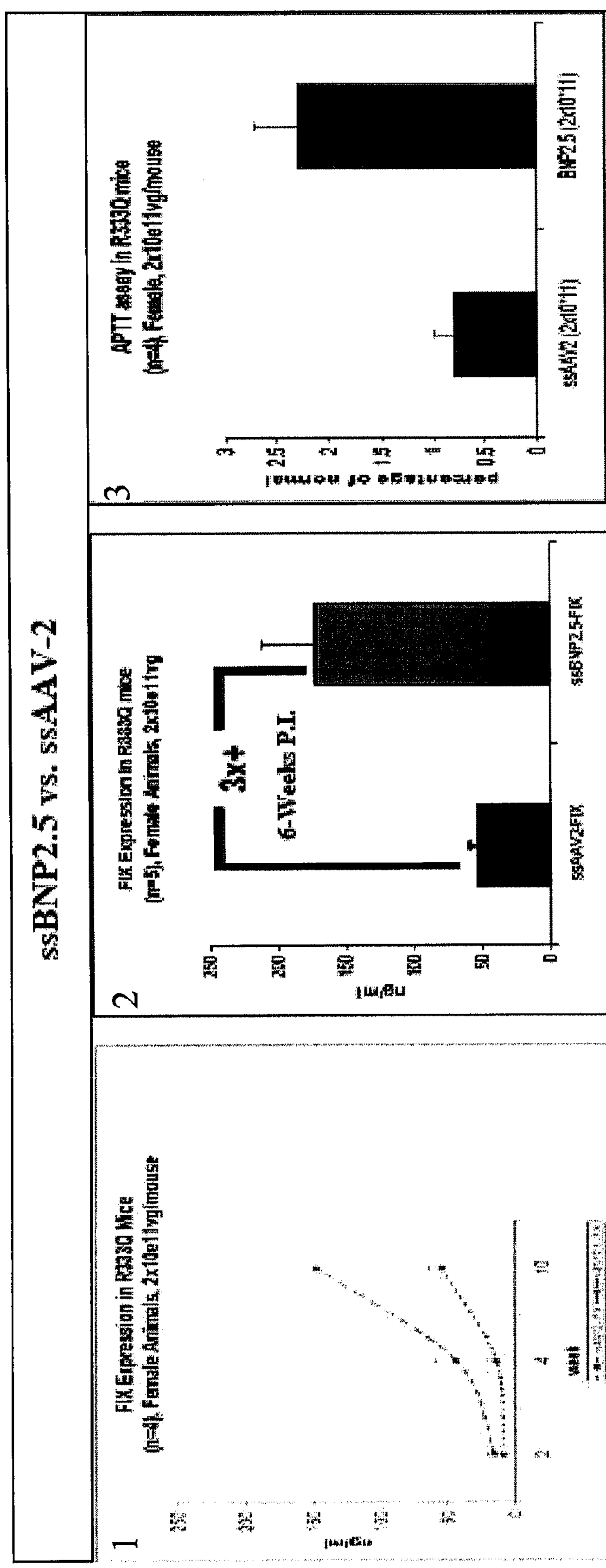
FIG. 6 shows FIX in vivo data from R333Q model 6 weeks post injection for ssBNP2.5 vs. ssAAV2 (6A (1, 2, and 3)) and dsBNP2.5 vs. ssAAV2 (6B (1, 2 and 3)).
Figure 6B:
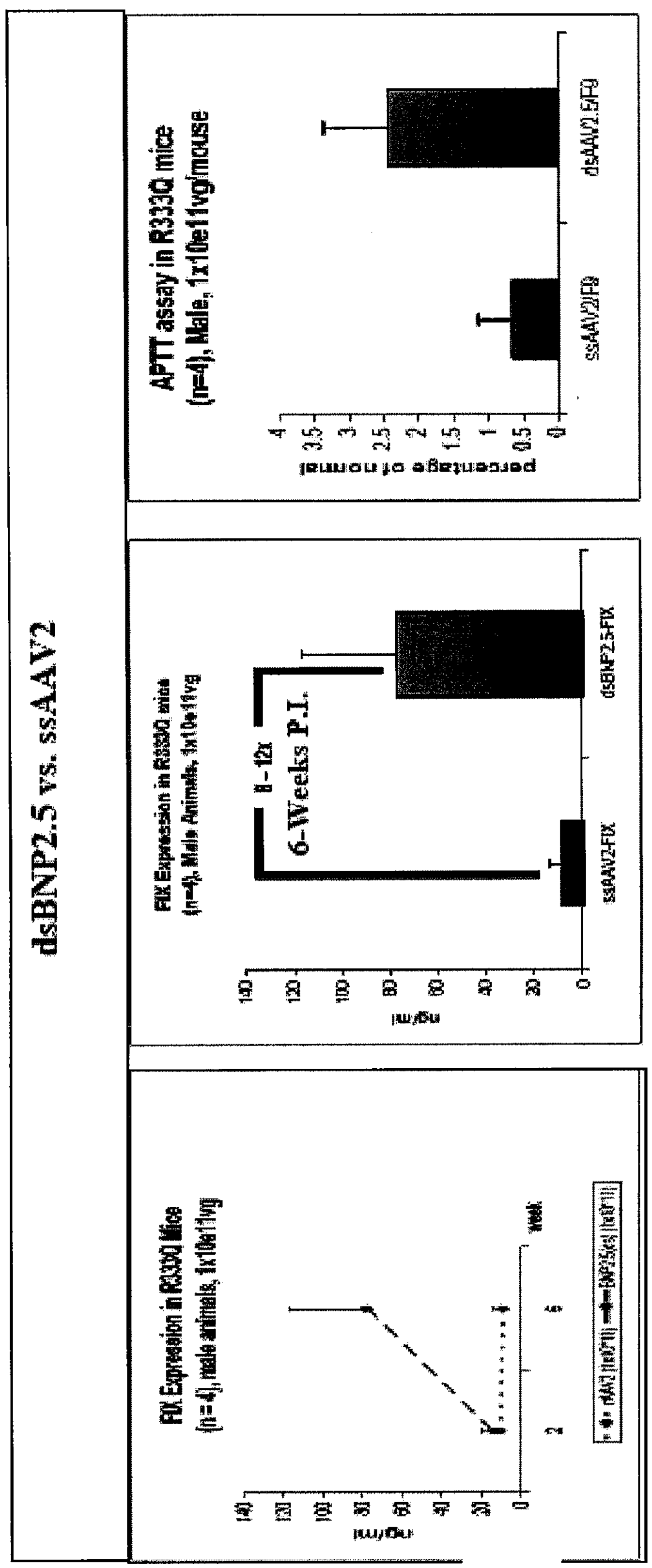

FIG. 6 shows FIX expression in vivo data from R333Q model 6 weeks post injection for ssBNP2.5 vs. ssAAV2 (FIG. 6A (1, 2, and 3)) and dsBNP2.5 vs. ssAAV2 (FIG. 6B (1, 2, and 3)).

Determining BNP FIX Performance after Liver Transduction

Figure 7:
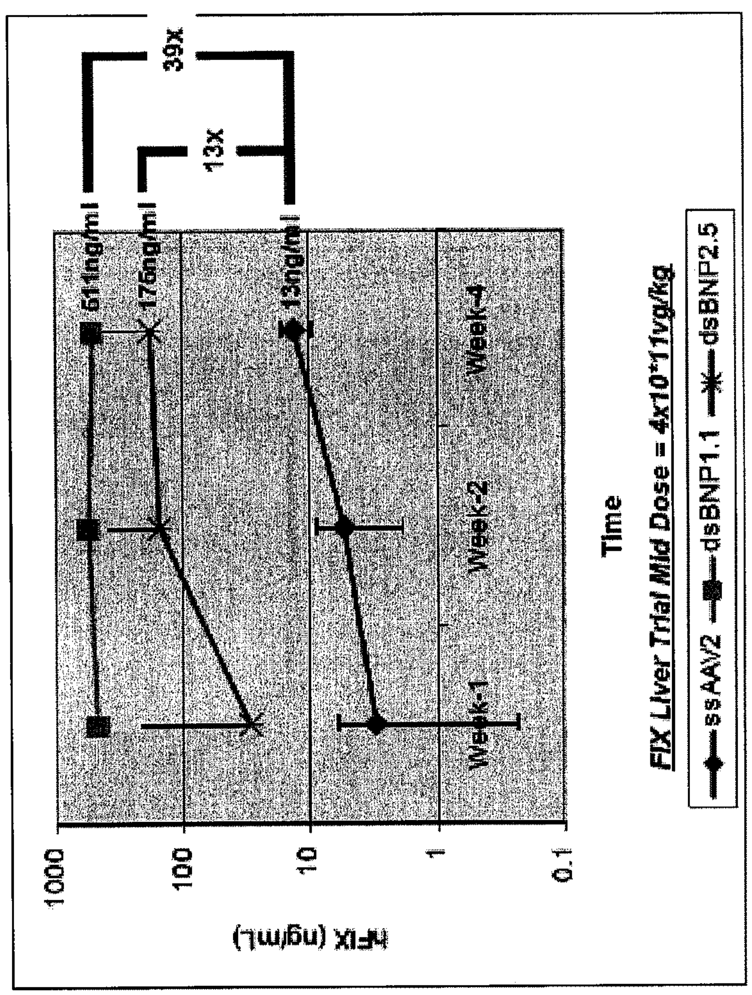
FIG. 7 shows the results of Portal vein administration in C57B1k6 using ssAAV2, dsBNP-1.1 and ds BNP 2.5 carrying the FIX transgene.

Although the original primary focus of this feasibility study was to determine BNP transduction in skeletal muscle for FIX expression, similar Phase I clinical studies showing AAV2 transduction in liver have yielded provocative results. AAV2 vector is safe at doses ranging from $8\times10^{11}$° to $4\times10^{11}$/kg but without therapeutic levels of transgene expression. Therapeutic levels of FIX can be obtained at $2\times10^{12}$/kg, but FIX transgene expression is transient (4 wk). While no formal understanding was obtained for the transient levels of FIX protein in transduce liver, speculation implicates that high vector dose may provoke immune response to transduce liver cells, supporting a conclusion that the invention provides a safe dose of FIX gene transfer ($10^{10}$ or $10^{11}$ dose) that is also efficacious (10-15% levels of FIX) by using AAV vectors using double stranded vector templates (FIG. 7). Mouse studies were carried out using BNP in vivo w/C57B16 mice. These experiments employed 3 cohorts with 4 animals/cohort; testing (ss)AAV2, (ds)BNP-1.1 and (ds)BNP-2.5 carrying FIX transgene, administered to the liver via portal vein administration and monitored for FIX levels to beyond four weeks. The data derived from these experiments points to a conclusion that (i) (ds)BNP is significantly more efficient compared to traditional ssAAV2 vector, (ii) hepatic efficiency in vector transduction and FIX expression is significantly improved over muscle (both primary human myoblasts in culture and R333Q in vivo results), (iii) and these novel reagents are ideally suited for allowing for an even lower dose than muscle mediated gene transfer of FIX to reach similar protein expression levels.

Additional Liver Data (Optimized Transgene)

Figure 8:
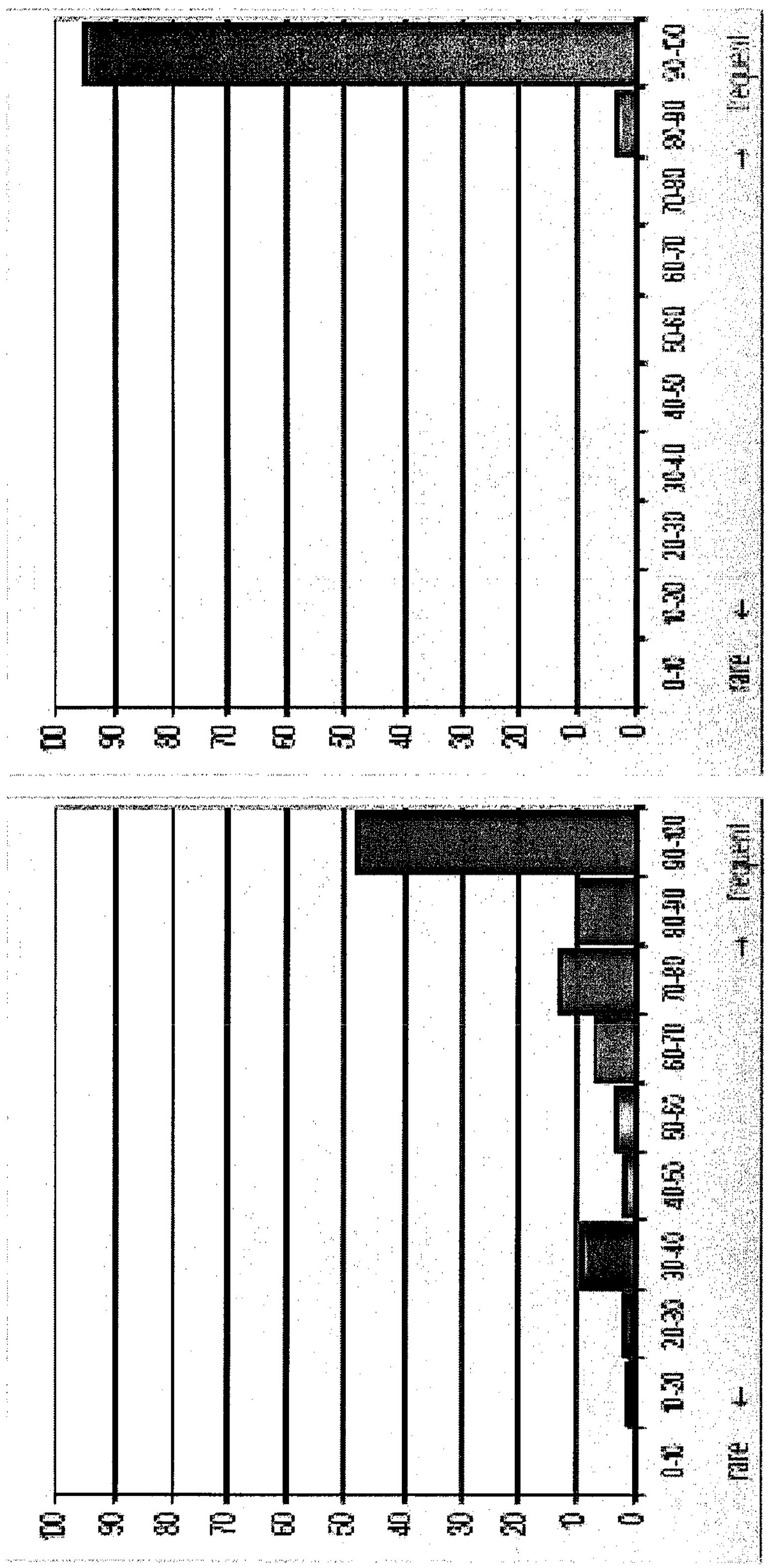
FIG. 8 shows the codon sequence of an optimized hFIX.

The FIX feasibility liver data in C57B16 mice suggests that safe and efficacious doses of double stranded gene transfer administered into the liver may be therapeutic at vector levels previously shown in patients as safe but not expressing sufficient hFIX. To elaborate further upon this point we have completed an additional study, in which we developed and used a transgene codon optimized hFIX. When computer program for optimum codon usage was applied to the "wild type" hFIX gene, we observed a large number of rare codons in the coding sequence (FIG. 8). In addition, hFIX gene contains low GC content (FIG. 9), a feature known to facilitate mRNA turnover. Moreover, several negatively cis-acting motifs were found, which may hamper expression in mammals. As such, a hFIX gene was synthesized in which the codon usage has been revised to more nearly approximate optimum codon bias of mammals (FIG. 8).

Figure 9:
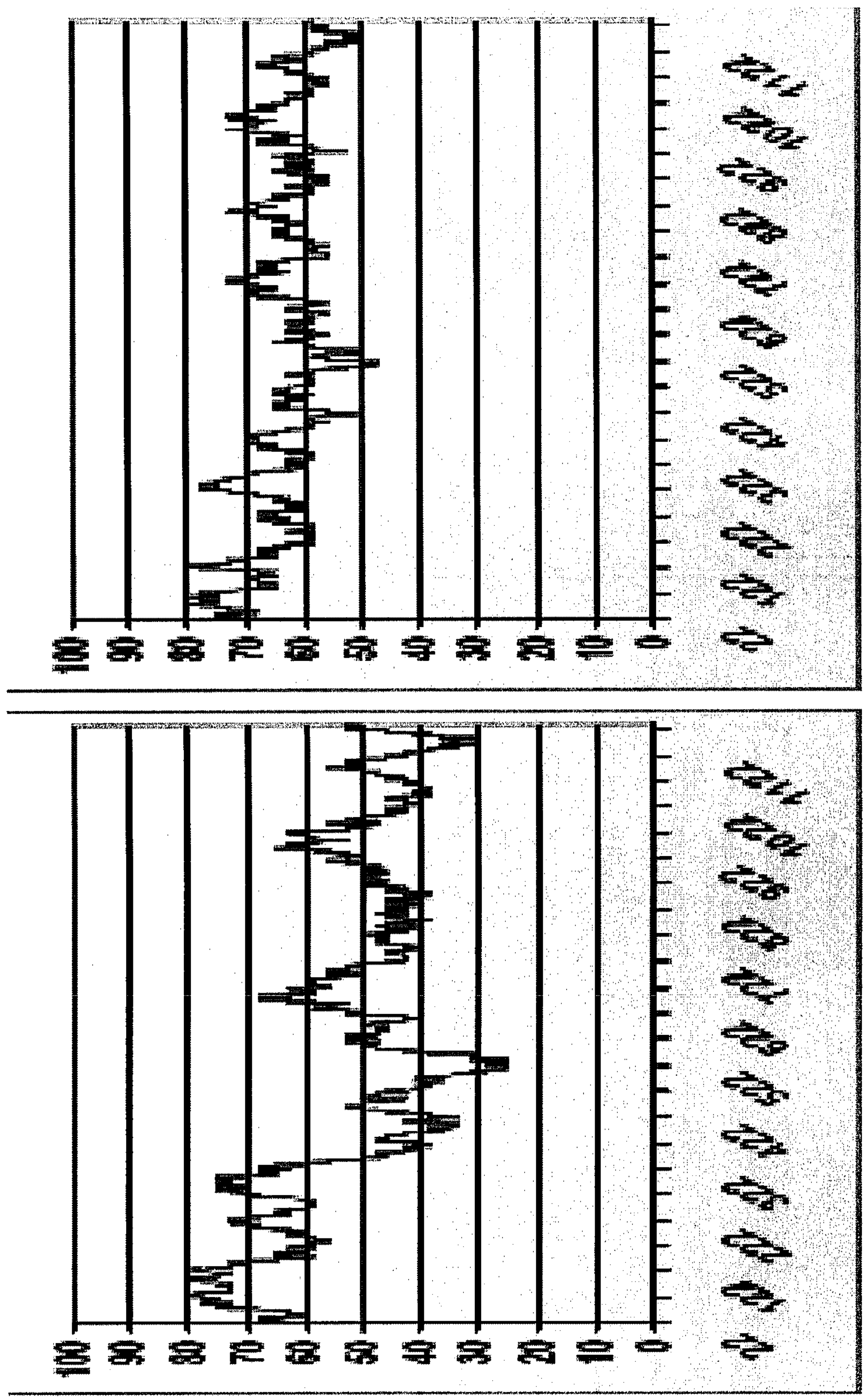
FIG. 9 shows the in vitro expression of wild-type vs optimized hFIX coding sequence.

Based on computer analysis, we removed negative cis-acting elements (such as splice sites, unwanted poly(A) signals, etc), which may negatively influence protein expression. In addition, the GC-content was increased to prolong mRNA half-life (FIG. 8). Codon usage was adapted to the bias of Homo sapiens resulting in a high Codon Adaptation Index (CAI) value. Based on these modifications, we predicted that the optimized gene would allow higher and more stable expression rates in mammalian cells. Using AAV2 carrying optimized vs. wild type hFIX coding sequence, we carried out side-by-side expression analysis in vitro (FIG. 9). Based on these studies it is clear that the optimized FIX gene expresses significantly more protein product/cell when compared to wild type coding sequence when delivered at the same dose.

Figure 10:
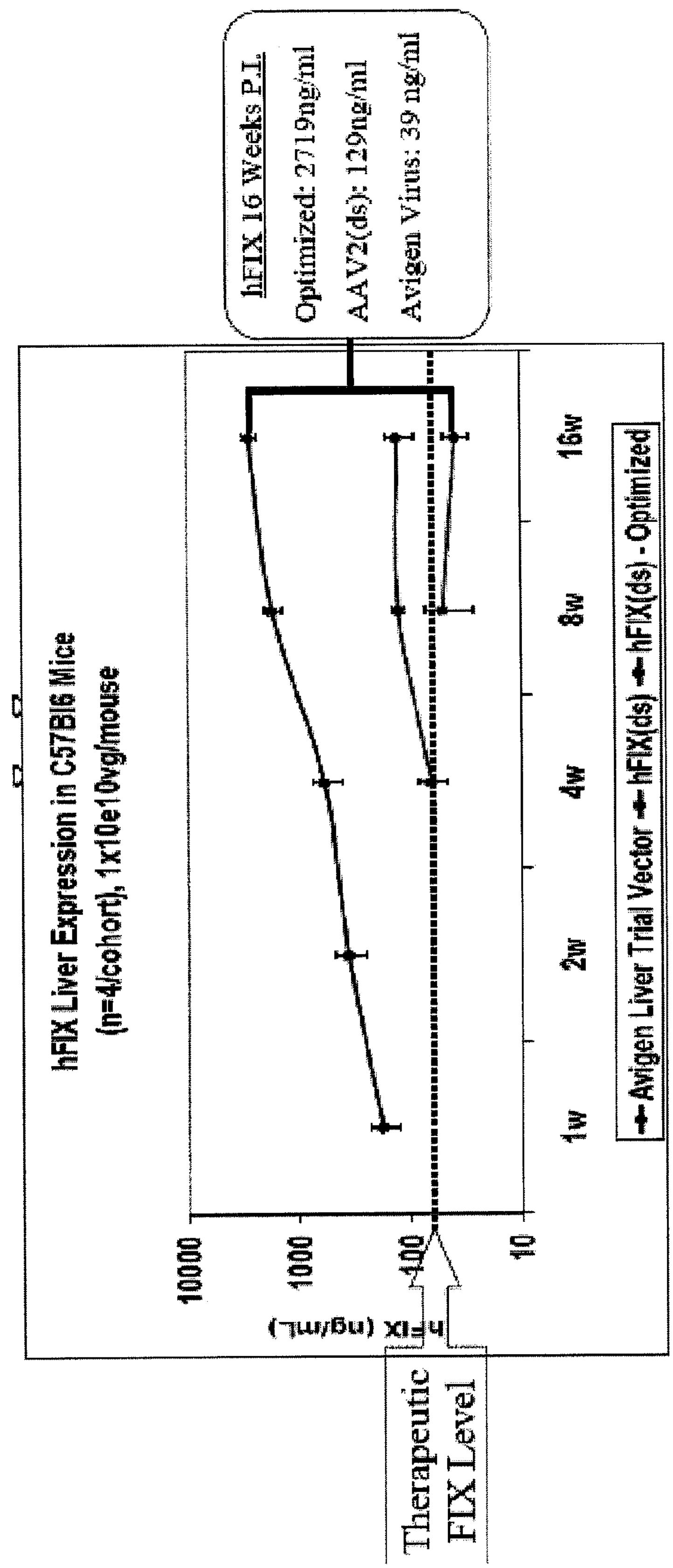
FIG. 10 shows expression of hFIX and comparison of Avigen virus ($4\times10^{11}$ vg/kg) vs AAV2 dshFIX and optimized hFIX.
Figure 11:
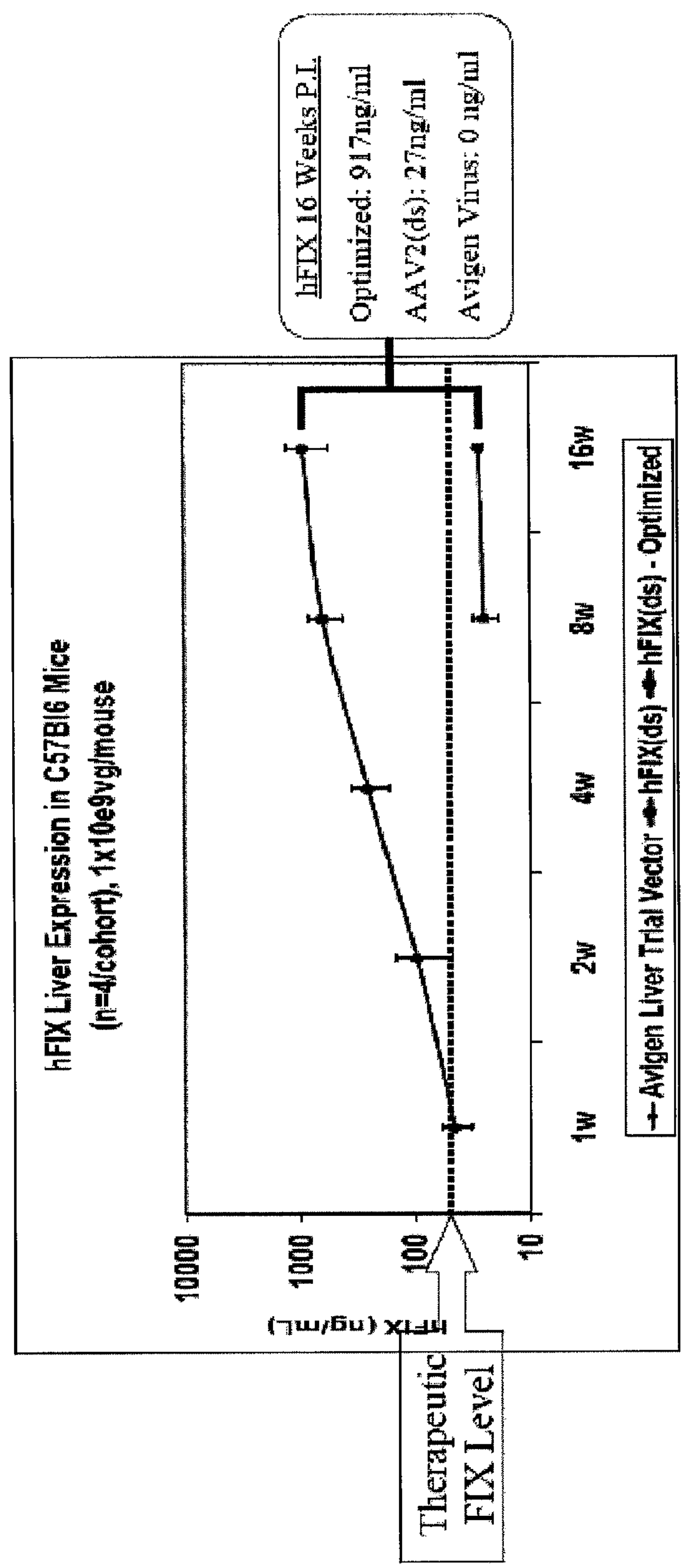
FIG. 11 shows expression of hFIX comparing Avigen virus ($8\times10^{10}$ vg/kg) vs AAV2 dshFIX and optimized hFIX.

Upon codon optimization a side by side comparison of in vivo vector expression of the liver mediated AAV2 clinical trial vector vs. double stranded and double stranded +codon optimized transgene cassette in C57BL6 mice. The dose chosen was shown in the clinical trial earlier to be sub-therapeutic but safe ($4\times10^{11}$ vg/kg). The animals at 8-10 weeks old received a single portal vein injection (n=4/serotype/dose). When using the clinical trial vector the results mirrored the clinical trial, with the AAV2 vector being sub therapeutic in vivo in all animals. At the same vector dose, AAV2 with a double stranded cassette after 4 weeks post injection expressed therapeutic levels of hFIX and sustained these levels out past 16 weeks, and AAV2 with a double stranded optimized transgene cassette, expressed therapeutic levels from week one through 16 weeks at up to 70 times the hFIX ng/ml compared to the clinical trial vector (FIG. 10, 11).

Immune Response to BNP2.5 in Animals Pre-Exposed to AAV

Since BNP2.5 carries a majority capsid backbone of AAV2 and minority amino acids from AAV 1, it was studied to determine whether the immune profile of this chimeric vector is identical to parental donor AAV2, shared between AAV 1 & AAV2, or distinct. If the chimeric vector displays a different immune profile than parent vectors, this may suggest that vector administration in patients pre-exposed to AAV1 or AAV2 is not rate-limiting to BNP vector transduction. If the data suggest that the BNP has an immune profile identical to parent vector, then there is a possibility that pre-exposure to wild type AAV would have an impact on BNP identical to studies established in the literature.

Figure 12:
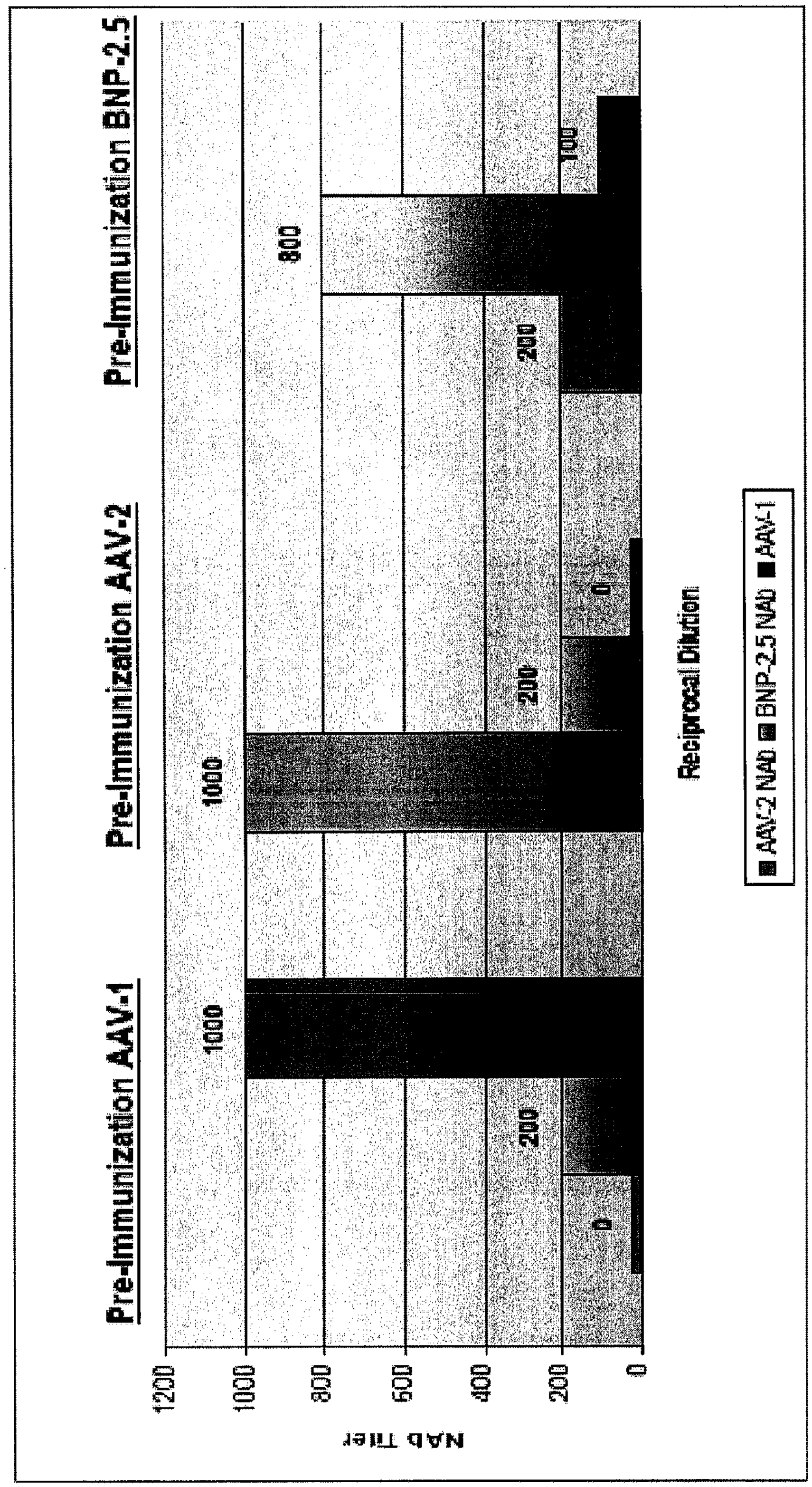
FIG. 12 shows the level of in vitro neutralizing antibody titer using AAV1, AAV2 and BNP-2.5.

These experiments were carried out in vitro and in vivo. In the in vitro experiments, C57B16 animals were pre-exposed to AAV1, AAV2, or BNP2.5 vector. Four weeks post 1M injection, sera was collected, and 293 cells at a density of $1\times10^5$ cells/well in 1 ml DMEM containing 10% FBS were seeded in a 24-well plate. The cells were cultured for 2-3 hrs at 37° C. and allowed to adhere to the well. The medium was removed before $1\times10^6$ particles of adenovirus d1309 were added in a final volume of 200 μl/well. The cells were further incubated at 37° C. for 1 hr and then washed twice. AAV-GFP vectors ($1\times10^8$ particles) were incubated with human sera at serial dilutions with PBS for 2 hrs at 4° C. in a total volume of 25 μl (12.5 ul serial dilution sera samples plus 12.5 μl of AAV/GFP vectors which contain $1\times10^8$ particles). The mixture was added to cells in a final volume of 2000 and incubated overnight at 37° C. GFP expressing cells were counted under a fluorescent microscope. The percent inhibition was calculated without serum sample as a reference. The neutralizing antibody titer was calculated (FIG. 12) using the highest dilution where the percentage of GFP expressed cells is 50% less than control without sera.

Figure 13:
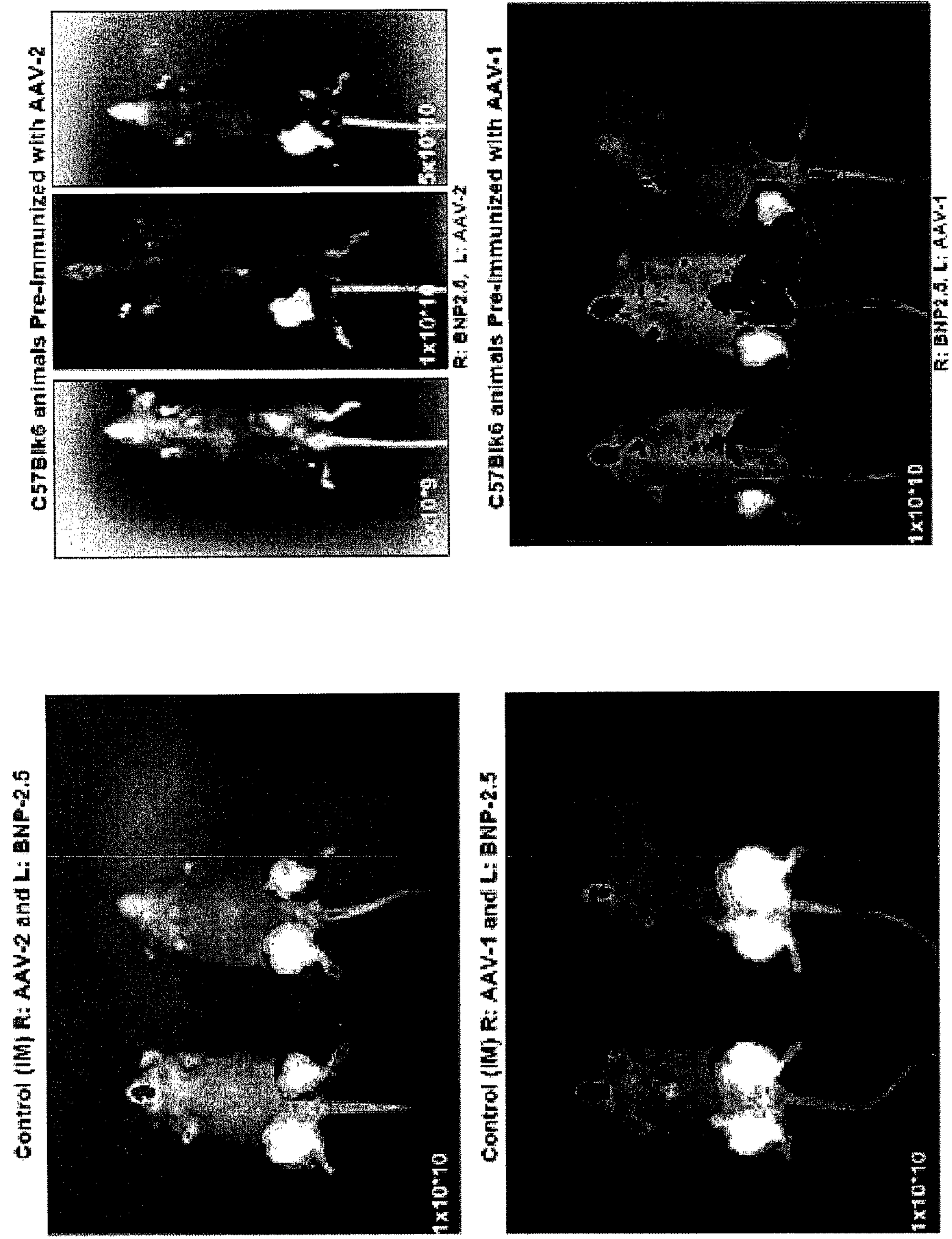
FIG. 13 shows the level of in vivo neutralizing antibody titer using AAV1, AAV2 and BNP-2.5.
Figure 14:
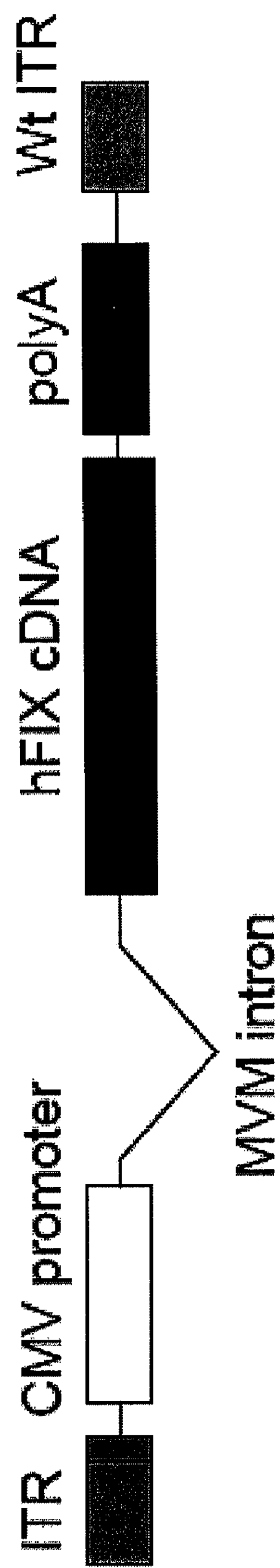
FIG. 14 shows a preferred vector of the present invention.

The in vivo experiments were implemented using the same C57B16 mice which have been primed with AAV1, AAV2, and BNP2.5. After four weeks, the mice were challenged with BNP vector 1M carrying Luc reporter and carrying the vector as shown in FIG. 14 with the sequence set forth in FIG. 15, and analyzed using real time imaging (FIG. 13). Control experiments of BNP with identical dose in naive animals were used.

Results

After six weeks post administration of an optimized vector dose of $1\times10^{11}$ vg/kg, the expression levels indicate a relative translation of FIX expression from tissue culture to in vivo. The rAAV2 provided the baseline and measured the lowest FIX expression. BNP2.5 (ss) and BNP2.5 (ds) both showed improvement over rAAV2, with single stranded measuring a 3-6 fold improvement in FIX and double stranded BNP2.5 deriving an 8-12 fold improvement in circulating FIX (FIG. 6). The work described here shows that the BNP double stranded "BNP(ds)" vector containing a FIX gene can transduce murine and canine striated muscle and hepatic cells resulting in FIX gene expression and protein secretion into the peripheral blood.

Modified codon FVIII (hFVIII) sequences and flanking sequences were developed (SEQ ID NOs: 12 and 15, FIGS. 22 and 23, respectively) using a computer program to synthesize an hFVIII gene in which the codon usage has been revised to more nearly approximate optimum codon bias of mammals, including optimization of GC content and cis-acting motifs.

Based on computer analysis, negative cis-acting elements (such as splice sites, unwanted poly(A) signals, etc) were removed that may negatively influence protein expression. In addition, the GC-content was increased to prolong mRNA half-life. Codon usage was adapted to the bias of *Homo sapiens* resulting in a high Codon Adaptation Index (CAI) value. Based on these modifications, the modified gene would likely allow higher and more stable expression rates in mammalian cells, specifically human cells or human derived cells.

Figure 17:
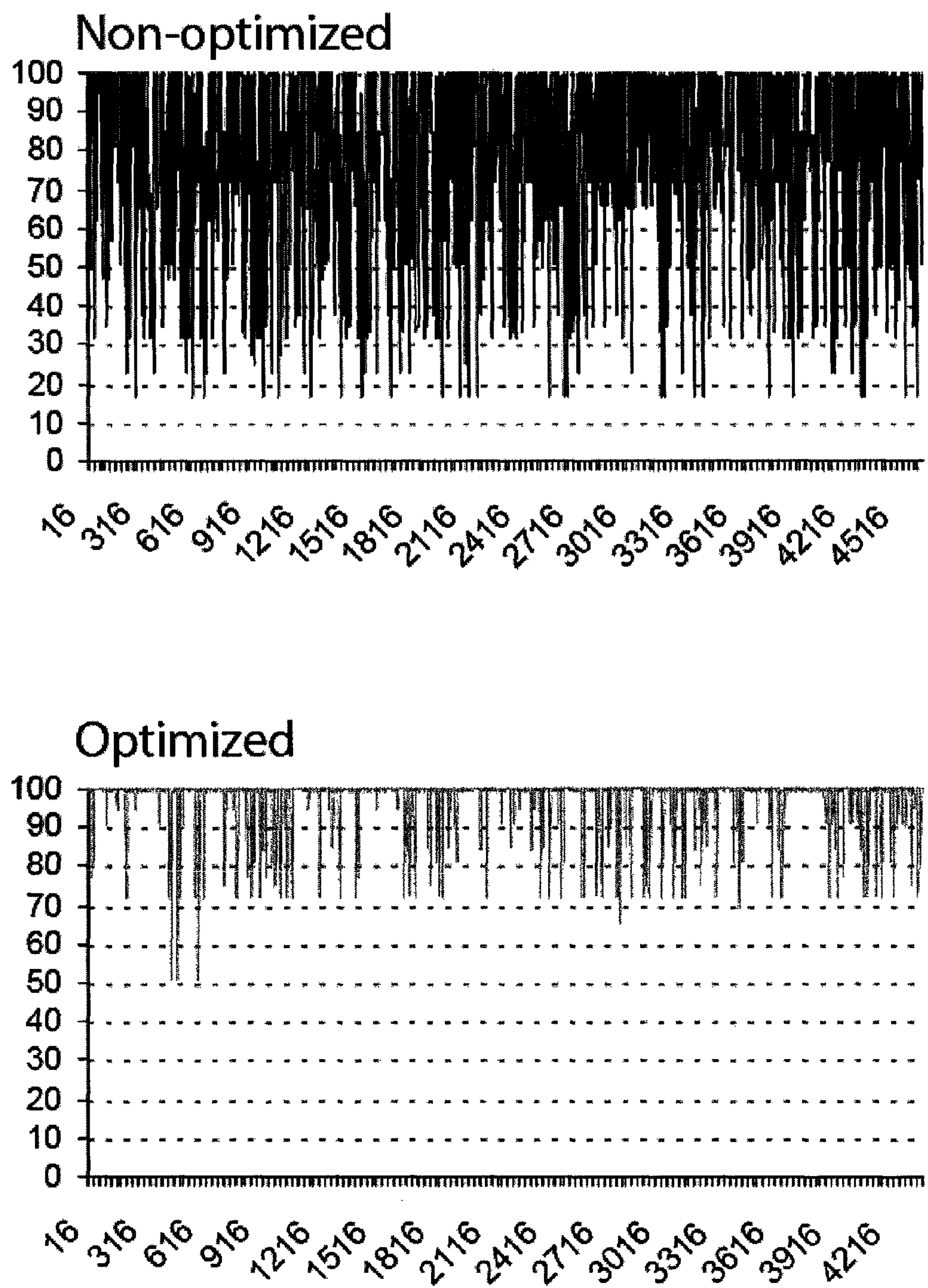
FIG. 17 shows the enhanced codon quality of SEQ ID NO: 12 relative to the non-optimized (SEQ ID NO: 19).

With respect to SEQ ID NO: 10, the histograms of FIG. 16 show the percentage of sequence codons, which fall into a certain quality class. The quality value of the most often used codon for a given amino acid in the desired expression system is set to 100, the remaining codons are scaled accordingly (See also Sharp, P. M., Li, W. H., Nucleic Acids Res. 15 (3), 1987). FIG. 17 shows a dramatically enhanced codon quality. FIG. 18 shows an increase in GC content from 44% (Wild type gene SEQ ID NO: 19) to 66% for optimized (SEQ ID NO. 12).

Modified motifs include the following:

| | | |
|---|---|---|
| Prokaryotic inhibitory motifs | 16 | 0 |
| polyA site | 3 | 0 |
| consensus (cryptic) splice donor site | 2 (9) | 0 |
| RNA instability motif (ARE) | 11 | 0 |

Figure 19:
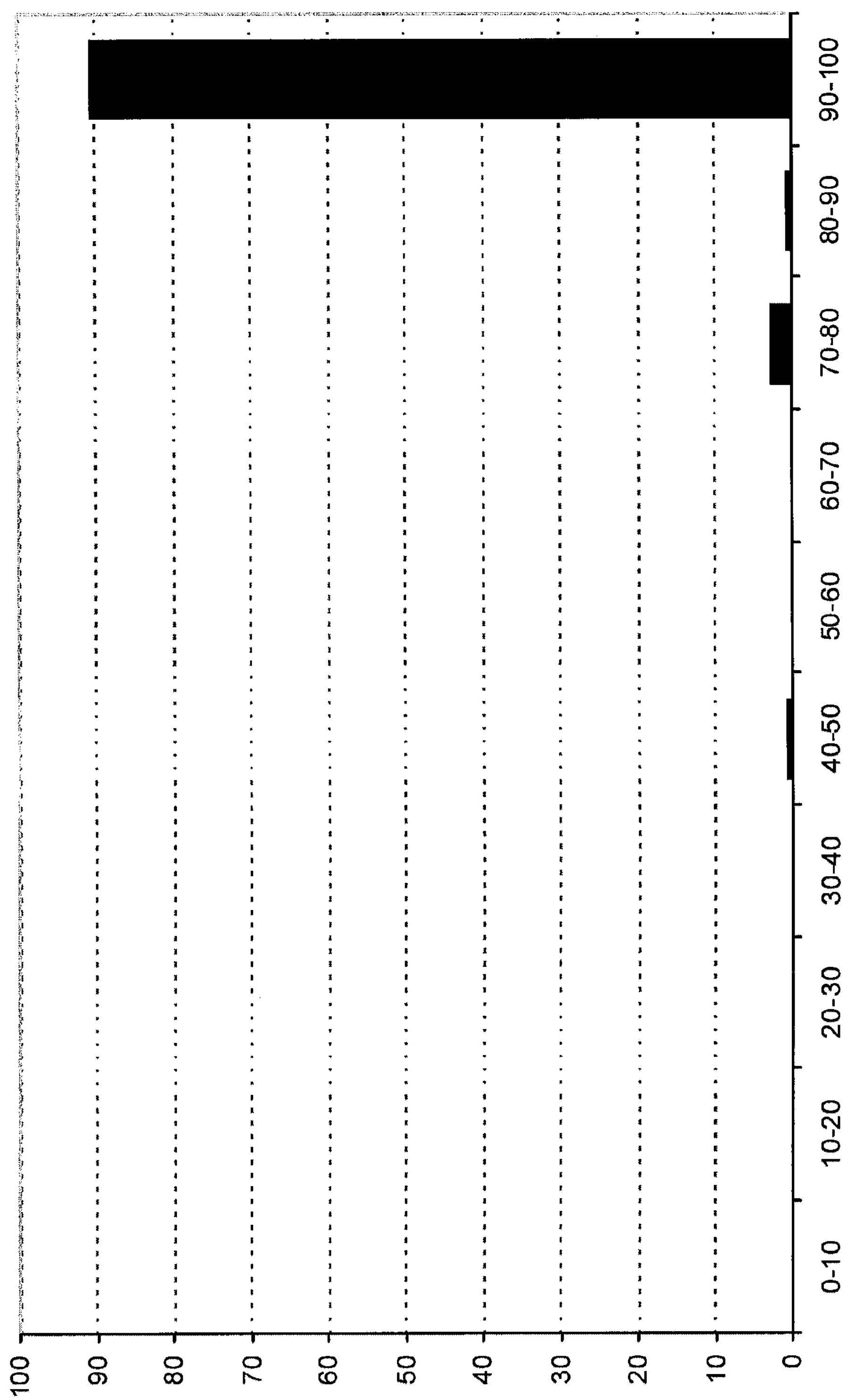
FIG. 19 shows codon quality relative to SEQ ID NO: 15.
Figure 20:
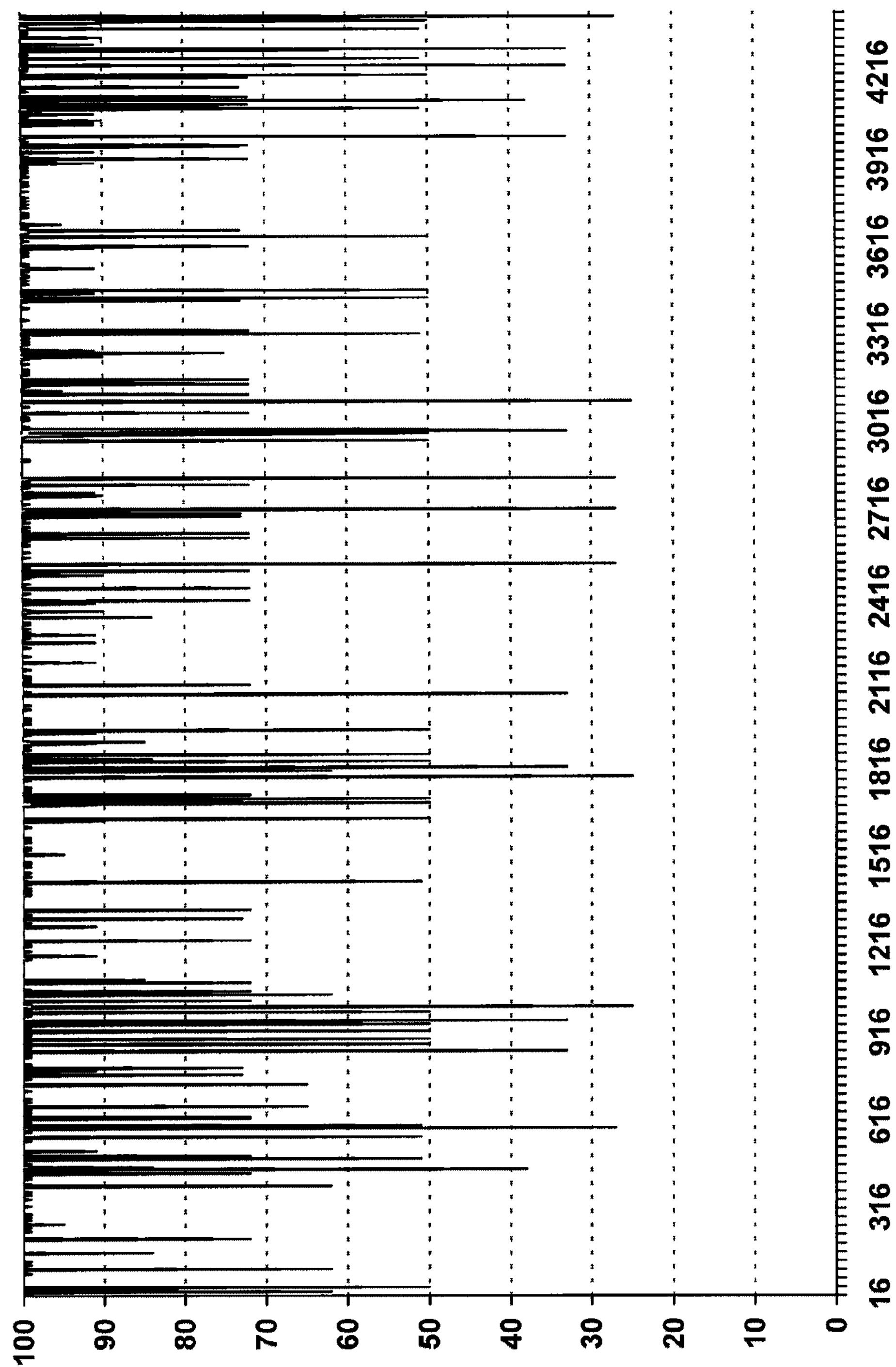
FIG. 20 shows a codon quality plot for SEQ ID NO: 19.
Figure 21:
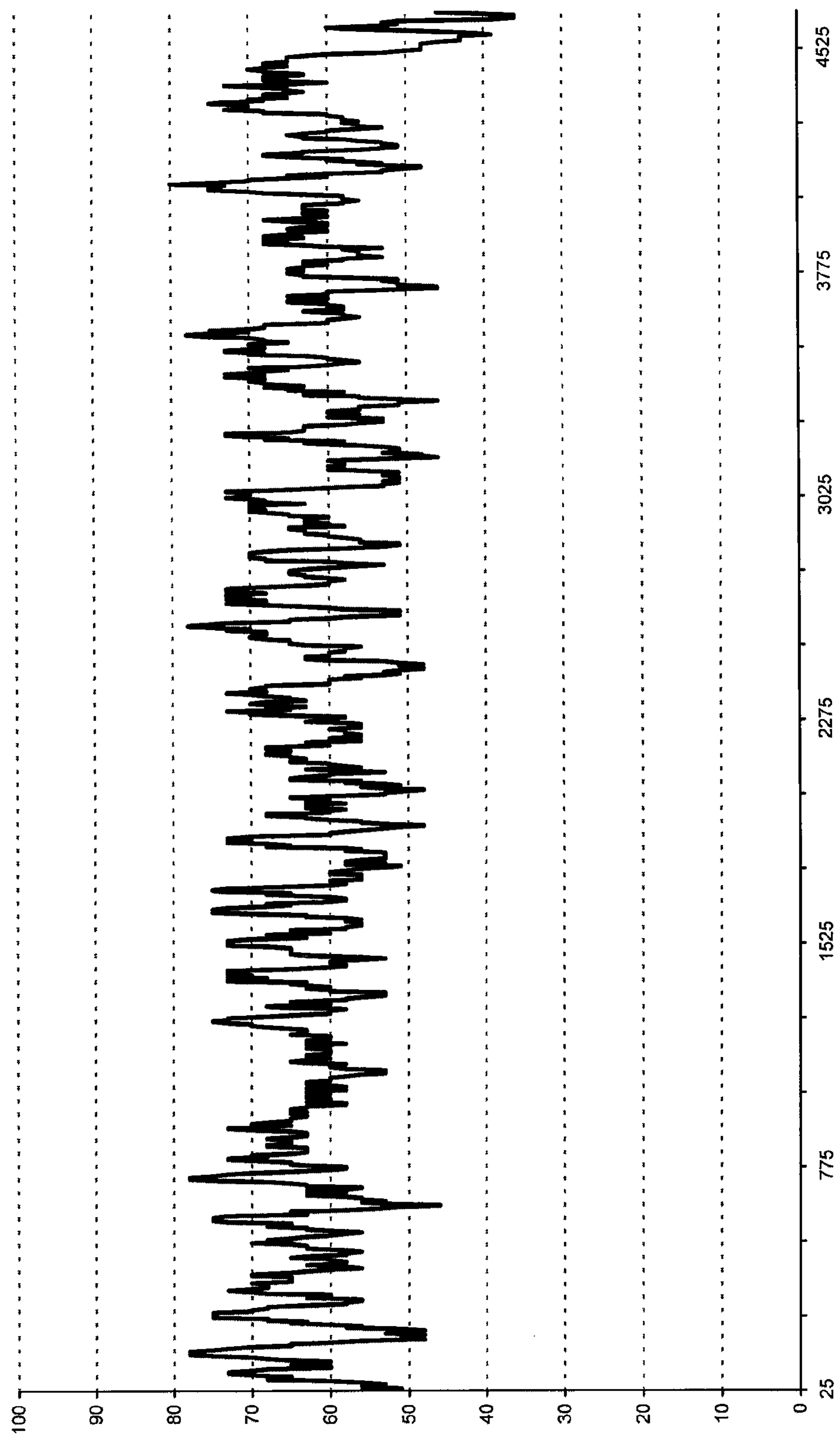
FIG. 21 shows the GC content plot for modified SEQ ID NO: 15 which is 62%.

With respect to SEQ ID NO: 14, FIG. 19 shows the percentage of sequence codons, which fall into a certain quality class. The Codon Adaptation Index is 0.96. FIG. 20 shows a codon quality plot. FIG. 21 shows a GC content plot; GC content is 62%.

The wildtype gene uses rare codons with a high frequency and the GC content is quite low which facilitates quick mRNA turnover. The optimization was successful: no negative cis-acting sites (such as splice sites, poly(A) signals, etc) which may negatively influence expression are present. GC-content was increased to prolong mRNA half-life and to improve the efficiency of vector packaging. Codon usage was adapted to the bias of *Homo sapiens* resulting in a high CAI* value (0.98). The optimized gene should therefore allow high and stable expression rates in *Homo sapiens* or other mammalian cells.

To confirm such increase expression rate, a side by side comparison of the vector expression of the liver mediated AAV2 clinical trial vector vs. double stranded and double stranded +codon modified transgene cassette (including SEQ ID NO: 12 or 15) is conducted in C57BL6 mice. The dose chosen will be one that has been shown to be sub-therapeutic but safe ($4\times10^{11}$ vg/kg). The animals at 8-10 weeks old will receive a single portal vein injection (n=4/serotype/dose).

These experiments are carried out in vitro and in vivo. In the in vitro experiments, C57B16 animals are pre-exposed to AAV1, AAV2, BNP2.5 vector, or any other suitable parvovirus vector. Four weeks post 1M injection, sera is collected, and 293 cells at a density of $1\times10^5$ cells/well in 1 ml DMEM containing 10% FBS are seeded in a 24-well plate. The cells are cultured for 2-3 hrs at 37° C. and allowed to adhere to the well. The medium is removed before $1\times10^6$ particles of adenovirus d1309 are added in a final volume of 200 μl/well. The cells are further incubated at 37° C. for 1 hr and then washed twice. AAV-GFP vectors ($1\times10^8$ particles) are incubated with human sera at serial dilutions with PBS for 2 hrs at 4° C. in a total volume of 25 μl (12.5 μl serial dilution sera samples plus 12.5 μl of AAV/GFP vectors which contain 1×108 particles). The mixture is added to cells in a final volume of 200 μl and incubated overnight at 37° C. GFP expressing cells are counted under a fluorescent microscope. The percent inhibition will be calculated without serum sample as a reference. The neutralizing antibody titer is calculated using the highest dilution where the percentage of GFP expressed cells is 50% less than control without sera.

The in vivo experiments is implemented using the same C57B16 mice which have been primed with AAV1, AAV2, BNP2.5, or any other parvovirus suitable vector. After four weeks, the mice are challenged with BNP vector 1M carrying Luc reporter and analyzed using real time imaging. Control experiments of BNP with identical dose in naive animals are used.

All publications, patent applications, patents, and other references mentioned herein are incorporated by reference in their entirety.

That which is claimed is:

1. An isolated optimized gene modified to increase CG sequences and reduce cis motifs relative to a wild type FVIII or wild type FIX gene, wherein the optimized gene is selected from the group consisting of FVIII and FIX, wherein when the optimized gene is FVIII the gene has the nucleotide sequence of SEQ ID NO: 12 or 15 or a nucleotide sequence having 95% identity thereto, and wherein when the optimized gene is FIX the gene has the nucleotide sequence of SEQ ID NO 7 or a nucleotide sequence having 95% identity thereto.

2. The optimized gene of claim 1, where the CG sequences are increased at least 40% relative to the wild type gene.

3. The optimized gene of claim 1, included in a virus vector or a chimeric virus vector.

4. The optimized gene of claim 3, wherein the chimeric virus vector comprises capsid components selected from AAV1, AAV2, AAV3, AAV4, AAV5, AAV6, AAV7 AAV8, AAV9, AAV10, AAV11 and AAV12 capsids.

5. The optimized gene of claim 4, wherein the chimeric virus vector comprises SEQ ID NO: 17 or its complement.

6. The optimized gene of claim 1, wherein the optimized gene is flanked by AAV TRs.

7. The optimized gene of claim 3, wherein the virus vector comprises the nucleotide sequence of SEQ ID NO. 1.

8. A method of increasing expression of FVIII or FIX genes in a subject, the method comprising:

providing at least one recombinant virus vector comprising a nucleotide sequences encoding an optimized FVIII or FIX gene according to claim 1, wherein the optimized genes have been modified to increase CG sequences and reduce cis motifs relative to a wild type FVIII gene or wild type FIX gene, respectively; and administering the recombinant virus vector to the subject under conditions such that the optimized FVIII or FIX nucleotide sequences are expressed at a level which produces an increased amount of FVIII or FIX in the subject.

9. The method of claim 8, where the CG sequences are increased at least 40% relative to the wild type gene.

10. The method of claim 8, wherein the recombinant virus vector is a chimeric virus vector.

11. The method of claim 10, wherein the chimeric virus vector comprises capsid components selected from AAV1, AAV2, AAV3, AAV4, AAV5, AAV6, AAV7 AAV8, AAV9, AAV10, AAV11 and AAV12 capsids.

12. The method of claim 11, wherein the chimeric virus vector comprises SEQ ID NO: 17 or its complement.

13. The method of claim 8, wherein the optimized gene is flanked by AAV TRs.

14. The method of claim 10, wherein the recombinant virus vector comprises the nucleotide sequence of SEQ ID NO. 1.

15. An in vitro process of expressing an optimized FVIII or FIX peptide comprising; transfecting a cell with polynucleotide that encodes the optimized FVIII or FIX peptide according to claim 1, to produce a transformed host cell, wherein the polynucleotide encoding the optimized FVIII or FIX genes have been modified to increase CG sequences and reduce cis motifs relative to a wild type FVIII gene or wild type FIX gene; and maintaining the transformed host cell under biological conditions sufficient for expression of the peptide.

16. A composition comprising an admixture of:

an isolated or purified nucleic acid according to claim 1, and a carrier.

* * * * *